United States Patent [19]

Woodward et al.

[11] 4,147,864
[45] Apr. 3, 1979

[54] PROCESS FOR THE MANUFACTURE OF 7β-AMINO-3-CEPHEM-3-OL-4 CARBOXYLIC ACID COMPOUNDS

[75] Inventors: Robert B. Woodward, Cambridge, Mass.; Hans Bickel, Binningen, Switzerland

[73] Assignee: Ciba-Geigy Corporation, Ardsley, N.Y.

[21] Appl. No.: 746,927

[22] Filed: Dec. 2, 1976

Related U.S. Application Data

[63] Continuation of Ser. No. 551,483, Feb. 20, 1975, abandoned.

[51] Int. Cl.$^2$ ............................................. C07D 501/02
[52] U.S. Cl. ........................................ 544/16; 544/22; 424/246; 260/239 A
[58] Field of Search ................ 260/243 C; 544/16, 22

[56] References Cited

U.S. PATENT DOCUMENTS

| | | | |
|---|---|---|---|
| 3,840,556 | 10/1974 | Kukulja | 260/243 C |
| 3,860,577 | 1/1975 | Kukulja | 260/243 C |
| 3,989,695 | 11/1976 | Scartazzini et al. | 544/16 |
| 4,007,202 | 2/1977 | Verweij | 260/243 C |
| 4,073,902 | 2/1978 | Scartazzini et al. | 544/16 |

FOREIGN PATENT DOCUMENTS

1368231 9/1974 United Kingdom.
1368234 9/1974 United Kingdom.

Primary Examiner—Nicholas S. Rizzo
Attorney, Agent, or Firm—John J. Maitner

[57] ABSTRACT

7β-amino-3-cephem-3-ol-4-carboxylic acid compounds of the formula

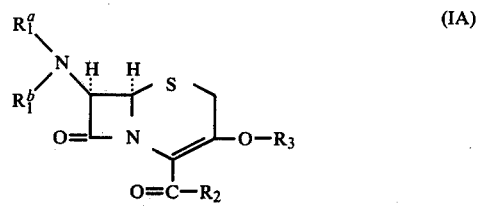

(IA)

wherein $R_1^a$ represents hydrogen or an amino protective group $R_1^A$ and $R_1^B$ represents hydrogen or an acyl group Ac, or $R_1^a$ and $R_1^b$ together represent a bivalent amino protective group, $R_2$ represents hydroxyl or a radical $R_2^A$ which together with the carbonyl grouping —C(=O)— forms a protected carboxyl group and $R_3$ represents hydrogen, lower alkyl or a hydroxyl protective group, and 1-oxides or 3-cephem compounds of the formula IA, and the corresponding 2-cephem compounds are prepared in that a compound of the formula

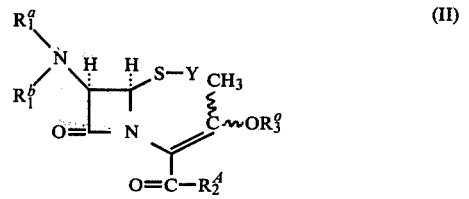

(II)

wherein $R_1^a$, $R_1^b$ and $R_2^A$ have the meanings mentioned under formula IA, $R_3^o$ represents lower alkyl or a hydroxyl protective group and Y represents a group which is removed, is treated with a base; also comprised are intermediate products.

16 Claims, No Drawings

PROCESS FOR THE MANUFACTURE OF 7β-AMINO-3-CEPHEM-3-OL-4 CARBOXYLIC ACID COMPOUNDS

This is a continuation of application Ser. No. 551,483 filed Feb. 20, 1975, now abandoned.

The subject of the present invention is a process for the manufacture of enol derivatives, especially 7β-amino-3-cephem-3-ol-4-carboxylic acid compounds of the formula

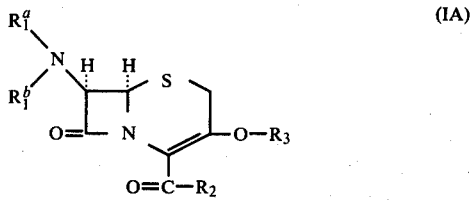

wherein $R_1^a$ represents hydrogen or an amino protective group $R_1^A$ and $R_1^b$ represents hydrogen or an acyl group Ac, or $R_1^a$ and $R_1^b$ together represent a bivalent amino protective group, $R_2$ represents hydroxyl or a radical $R_2^A$ which together with the carbonyl grouping —C(=O)— forms a protected carboxyl group and $R_3$ represents hydrogen, lower alkyl or a hydroxyl protective group, and 1-oxides of 3-cephem compounds of the formula IA and the corresponding 2-cephem compounds of the formula

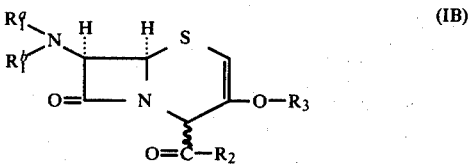

wherein $R_1^a$, $R_1^b$, $R_2$ and $R_3$ have the abovementioned meanings, or salts of such compounds with salt-forming groups.

The enol derivatives of the present invention are ethers of 3-cephem-3-ol or 2-cephem-3-ol compounds.

In 2-cephem compounds of the formula IB having the double bond in the 2,3-position, the optionally protected carboxyl group of the formula —C(=O)—R$_2$ preferably has the α-configuration.

An amino protective group $R_1^A$ is a group which can be replaced by hydrogen, above all an acyl group Ac, also a triarylmethyl group, especially the trityl group, as well as an organic silyl group, or an organic stannyl group. A group Ac, which can also represent a radical $R_1^b$, above all represents the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid) and the acyl radical of a carbonic acid half-derivative.

A bivalent amino protective group formed by the radicals $R_1^a$ and $R_1^b$ together is, in particular, the bivalent acyl radical of an organic dicarboxylic acid, preferably with up to 18 carbon atoms, above all the diacyl radical of an aliphatic or aromatic dicarboxylic acid, and also the acyl radical of an α-aminoacetic acid which is preferably substituted in the α-position and contains, for example, an aromatic or heterocyclic radical, and wherein the amino group is bonded to the nitrogen atom via a methylene radical which is preferably substituted and, for example, contains two lower alkyl groups, such as methyl groups. The radicals $R_1^a$ and $R_1^b$ can together also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—R$_2^A$ is above all an esterified carboxyl group but can also be an anhydride group, usually a mixed anhydride group, or an optionally substituted carbamoyl or hydrazinocarbonyl group.

The group $R_2^A$ can therefore be a hydroxyl group etherified by an organic radical, wherein the organic radical preferably contains up to 18 carbon atoms, which together with the —C(=O)— grouping forms an esterified carboxyl group. Examples of such organic radicals are aliphatic, cycloaliphatic, cycloaliphatic-aliphatic, aromatic or araliphatic radicals, especially optionally substituted hydrocarbon radicals of this nature, as well as heterocyclic or heterocyclic-aliphatic radicals.

The group $R_2^A$ can also represent an organic silyloxy radical as well as a hydroxyl group etherified by an organometallic radical, such as an appropriate organic stannyloxy group, especially a silyloxy or stannyloxy group which is substituted by 1 to 3 optionally substituted hydrocarbon radicals, preferably with up to 18 carbon atoms, such as aliphatic hydrocarbon radicals, and optionally by halogen, such as chlorine.

A radical $R_2^A$ which forms, with a —C(=O)— grouping, an anhydride group, above all a mixed anhydride group, is for example halogen, such as chlorine or an acyloxy radical, wherein acyl represents the corresponding radical of an organic carboxylic acid, preferably with up to 18 carbon atoms, such as of an aliphatic, cycloaliphatic, cycloaliphatic-aliphatic, aromatic or araliphatic carboxylic acid or of a carbonic acid half-derivative, such as of a carbonic acid half-ester.

A radical $R_2^A$ which forms a carbamoyl group with a —C(=O)— grouping is an optionally substituted amino group wherein substituents represent optionally substituted monovalent or bivalent hydrocarbon radicals, preferably with up to 18 carbon atoms, such as optionally substituted monovalent or bivalent aliphatic, cycloaliphatic, cycloaliphatic-aliphatic, aromatic or araliphatic hydrocarbon radicals with up to 18 carbon atoms, also appropriate heterocyclic or heterocyclic-aliphatic radicals with up to 18 carbon atoms and/or functional groups, such as optionally functionally modified, but especially free, hydroxyl and also etherified or esterified hydroxyl, wherein the etherifying or esterifying radicals have, for example, the abovementioned meanings and preferably contain up to 18 carbon atoms, as well as acyl radicals, above all of organic carboxylic acids and of carbonic acid half-derivatives, preferably with up to 18 carbon atoms.

In a substituted hydrazinocarbonyl group of the formula —C(=O)—R$_2^A$, one or both nitrogen atoms can be substituted, possible substituents being above all optionally substituted monovalent or bivalent hydrocarbon radicals, preferably with up to 18 carbon atoms, such as optionally substituted, monovalent or bivalent aliphatic, cycloaliphatic, cycloaliphatic-aliphatic, aromatic or araliphatic hydrocarbon radicals with up to 18 carbon atoms and also appropriate heterocyclic or heterocyclic-aliphatic radicals with up to 18 carbon atoms and/or functional groups, such as acyl radicals, above all of organic carboxylic acids or of carbonic acid half-derivatives, preferably with up to 18 carbon atoms.

A lower alkyl group $R_3$ has up to 7, preferably up to 4, carbon atoms and is, in particular, methyl.

A hydroxyl protective group $R_3$ is, for example, an easily removable 2-oxa-aliphatic or 2-thia-aliphatic or 2-oxa-cycloaliphatic or 2-thia-cycloaliphatic hydrocarbon radical, an easily removable substituted silyl or stannyl group, or an also easily removable, optionally substituted, α-phenyl-lower alkyl group, such as an optionally substituted benzyl or diphenylmethyl group.

The general concepts used in the preceding and following description have, for example, the following meanings:

An aliphatic radical, including the aliphatic radical of an appropriate organic carboxylic acid, as well as an appropriate ylidene radical, is an optionally substituted monovalent or divalent aliphatic hydrocarbon radical, especially lower alkyl, as well as lower alkenyl or lower alkinyl, and also lower alkylidene which can contain, for example, up to 7, preferably up to 4, carbon atoms. Such radicals can optionally be monosubstituted, disubstituted or polysubstituted by functional groups, for example by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio, phenyl-lower alkylthio, heterocyclthio or heterocyclyl-lower alkylthio, optionally substituted lower alkoxycarbonyloxy or lower alkanoyloxy, or halogen, also by oxo, nitro, optionally substituted amino, for example lower alkylamino, di-lower alkylamino, lower alkyleneamino, oxa-lower alkyleneamino or aza-lower alkyleneamino, as well as acylamino, such as lower alkanoylamino, lower alkoxycarbonylamino, halogeno-lower alkoxycarbonylamino, optionally substituted phenyl-lower alkoxycarbonylamino, optionally substituted carbamoylamino, ureidocarbonylamino or guanidinocarbonylamino and also sulphoamino which is optionally present in the form of a salt, such as in the form of an alkali metal salt, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl and also optionally substituted ureidocarbonyl or guanidinocarbonyl, or nitrile, optionally functionally modified sulpho, such as sulphamoyl or sulpho present in the form of a salt, or optionally O-monosubstituted or O,O-disubstituted phosphono, wherein substituents represent, for example, optionally substituted lower alkyl, phenyl or phenyl-lower alkyl, it also being possible for O-unsubstituted or O-monosubstituted phosphono to be in the form of a salt, such as in the form of an alkali metal salt.

A bivalent aliphatic radical, including the appropriate radical of a bivalent aliphatic carboxylic acid, is, for example, lower alkylene or lower alkenylene, which can optionally be monosubstituted, disubstituted or polysubstituted, for example like an aliphatic radical indicated above, and/or be interrupted by heteroatoms, such as oxygen, nitrogen or sulphur.

A cycloaliphatic or cycloaliphatic-aliphatic radical, including the cycloaliphatic or cycloaliphatic-aliphatic radical in an appropriate organic carboxylic acid or an appropriate cycloaliphatic or cycloaliphatic-aliphatic ylidene radical, is an optionally substituted, monovalent or bivalent, cycloaliphatic or cycloaliphatic-aliphatic hydrocarbon radical, for example monocyclic, bicyclic or polycyclic cycloalkyl or cycloalkenyl, and also cycloalkylidene, or cycloalkyl- or cycloalkenyl-lower alkyl or -lower alkenyl, as well as cycloalkyl-lower alkylidene or cycloalkenyl-lower alkylidene, wherein cycloalkyl and cycloalkylidene contains, for example, up to 12, such as 3-8, preferably 3-6, ring carbon atoms, whilst cycloalkenyl contains, for example, up to 12, such as 3-8, for example 5-8, preferably 5 or 6, ring carbon atoms and 1 to 2 double bonds, and the aliphatic part of a cycloaliphatic-aliphatic radical can contain, for example, up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the abovementioned optionally substituted lower alkyl groups or, for example, like the abovementioned aliphatic hydrocarbon radicals, by functional groups.

An aromatic radical, including the aromatic radical of an appropriate carboxylic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

A bivalent aromatic radical, for example of an aromatic carboxylic acid, is above all 1,2-arylene, especially 1,2-phenylene, which can optionally be monosubstituted, disubstituted or polysubstituted, for example like the abovementioned aliphatic and cycloaliphatic hydrocarbon radicals.

An araliphatic radical, including the araliphatic radical in an appropriate carboxylic acid, and also an araliphatic ylidene radical, is, for example, an optionally substituted araliphatic hydrocarbon radical, such as an aliphatic hydrocarbon radical which is optionally substituted and possesses, for example, up to three optionally substituted monocyclic, bicyclic or polycyclic aromatic hydrocarbon radicals, and above all represents phenyl-lower alkyl or phenyl-lower alkenyl as well as phenyl-lower alkinyl and also phenyl-lower alkylidene, it being possible for such radicals to contain, for example, 1–3 phenyl groups and to be optionally monosubstituted, disubstituted or polysubstituted in the aromatic and/or aliphatic part, for example like the abovementioned aliphatic and cycloaliphatic radicals.

Heterocyclic groups, including those in heterocyclic-aliphatic radicals, including heterocyclic or heterocyclic-aliphatic groups in appropriate carboxylic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also appropriate partially or wholly saturated heterocyclic radicals of this nature and such radicals can optionally be monosubstituted, disubstituted or polysubstituted, for example like the abovementioned cycloaliphatic radicals. The aliphatic part in heterocyclic-aliphatic radicals has, for example, the meaning indicated for the corresponding cycloaliphatic-aliphatic or araliphatic radicals.

The acyl radical of a carbonic acid half-derivative is preferably the acyl radical of an appropriate half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester of carbonic acid which is optionally substituted, for example in the α- or β-position, as well as of a lower alkenyl, cycloalkyl, phenyl or phenyl-lower alkyl half-ester of carbonic acid which is optionally substituted in the organic radical. Acyl radicals of a carbonic acid half-ester are furthermore appropriate radicals of lower alkyl half-esters of carbonic acid, in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

An etherified hydroxyl group is above all optionally substituted lower alkoxy, wherein substituents above all represent free or functionally modified, such as etherified or esterified, hydroxyl groups, especially lower alkoxy or halogen, also lower alkenyloxy, cycloalkyloxy or optionally substituted phenyloxy, as well as heterocyclyloxy or heterocyclyl-lower alkoxy especially also optionally substituted phenyl-lower alkoxy.

An optionally substituted amino group is, for example, amino, lower alkylamino, di-lower alkylamino, lower alkyleneamino, oxa-lower alkyleneamino, thia-lower alkyleneamino, aza-lower alkyleneamino, hydroxyamino, lower alkoxyamino, lower alkanoyloxyamino, lower alkoxycarbonylamino or lower alkanoylamino.

An optionally substituted hydrazino group is, for example, hydrazino, 2-lower alkylhydrazino, 2,2-di-lower alkylhydrazino, 2-lower alkoxycarbonylhydrazino or 2-lower alkanoylhydrazino.

Lower alkyl is, for example, methyl, ethyl, n-propyl, isopropyl, n-butyl, isobutyl, sec.-butyl or tert.-butyl, as well as n-pentyl, isopentyl, n-hexyl, isohexyl or n-heptyl, whilst lower alkenyl can, for example, be vinyl, allyl, isopropenyl, 2- or 3-methallyl or 3-butenyl, lower alkinyl can, for example, be propargyl or 2-butinyl and lower alkylidene can, for example, be isopropylidene or isobutylidene.

Lower alkylene is, for example, 1,2-ethylene, 1,2- or 1,3-propylene, 1,4-butylene, 1,5-pentylene or 1,6-hexylene, whilst lower alkenylene is, for example, 1,2-ethenylene or 2-buten-1,4-ylene. Lower alkylene interrupted by hetero-atoms is, for example, oxa-lower alkylene, such as 3-oxa-1,5-pentylene, thia-lower alkylene, such as 3-thia-1,5-pentylene, or aza-lower alkylene, such as 3-lower alkyl-3-aza-1,5-pentylene, for example 3-methyl-3-aza-1,5-pentylene.

Cycloalkyl is, for example, cyclopropyl, cyclobutyl, cyclopentyl, cyclohexyl or cycloheptyl as well as adamantyl, cycloalkenyl is, for example, cyclopropenyl, 1-, 2- or 3-cyclopentenyl, 1-, 2- or 3-cyclohexenyl, 3-cycloheptenyl or 1,4-cyclohexadienyl and cycloalkylidene is, for example, cyclopentylidene or cyclohexylidene. Cycloalkyl-lower alkyl or -lower alkenyl is, for example, cyclopropyl-, cyclopentyl-, cyclohexyl- or cycloheptyl-methyl, -1,1- or -1,2-ethyl, -1,1-, -1,2- or -1,3-propyl, -vinyl or -allyl, whilst cycloalkenyl-lower alkyl or -lower alkenyl represents, for example, 1-, 2- or 3-cyclopentenyl-, 1-, 2- or 3-cyclohexenyl- or 1-, 2- or 3-cycloheptenyl-methyl, -1,1- or -1,2-ethyl, -1,1-, -1,2- or -1,3-propyl, -vinyl or -allyl. Cycloalkyl-lower alkylidene is, for example, 3-cyclohexenylmethylene.

Naphthyl is 1- or 2-naphthyl, whilst biphenylyl represents, for example, 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, styryl or cinnamyl, naphthyl-lower alkyl is, for example, 1- or 2-naphthylmethyl and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacyclic radicals, such as pyrryl, for example 2-pyrryl or 3-pyrryl, pyridyl, for example 2-, 3- or 4-pyridyl and also pyridinium, thienyl, for example 2- or 3-thienyl, or furyl, for example 2-furyl, bicyclic monoazacyclic, monooxacyclic or monothiacyclic radicals, such as indolyl, for example 2- or 3-indolyl, quinolyl, for example 2- or 4- quinolyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, oxazacyclic, thiazacyclic or thiadiazacyclic radicals, such as imidazolyl, for example 2-imidazolyl, pyrimidinyl, for example 2- or 4-pyrimidinyl, traizolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 4-isothiazolyl, or 1,2,4- or 1,3,4-thiadiazolyl, for example 1,2,4-thiadiazol-3-yl or 1,3,4-thiadiazol-2-yl, or bicyclic diazacyclic, oxazacyclic or thiazacyclic radicals, such as benzimidazolyl, for example 2-benzimidazolyl, benzoxazolyl, for example 2-benzoxazolyl, or benzthiazolyl, for example 2-benzthiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are lower alkyl or lower alkenyl containing heterocyclic groups, especially those mentioned above. The abovementioned heterocyclyl radicals can be substituted, for example by optionally substituted aliphatic or aromatic hydrocarbon radicals, especially lower alkyl, such as methyl, or phenyl which is optionally substituted, for example by halogen such as chlorine, for example phenyl or 4-chlorophenyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentoxy or tert.-pentoxy. These groups can be substituted, for example as in halogeno-lower alkoxy, especially 2-halogeno-lower alkoxy, for example 2,2,2-trichloroethoxy, 2-chloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentyloxy, cyclohexyloxy or adamantyloxy, phenyl-lower alkoxy is, for example, benzyloxy, 1- or 2-phenylethoxy, diphenylmethoxy or 4,4'-dimethoxy-diphenylmethoxy and heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio, and phenyl-lower alkylthio is, for example, benzylthio, whilst mercapto groups etherified by heterocyclyl radicals or heterocyclyl-aliphatic radicals are especially pyridylthio, for example 4-pyridylthio, imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkoxycarbonyloxy, for example methoxycarbonyloxy, ethoxycarbonyloxy or tert.-butoxycarbonyloxy, 2-halogeno-lower alkoxycarbonyloxy, for example 2,2,2-trichloroethoxy-carbonyloxy, 2-bromoethoxycarbonyloxy or 2-iodoethoxycarbonyloxy, or arylcarbonylmethoxycarbonyloxy, for example phenacyloxycarbonyloxy.

Lower alkoxycarbonyl is, for example, methoxycarbonyl, ethoxycarbonyl, n-propoxycarbonyl, isopropoxycarbonyl, tert.-butoxycarbonyl or tert.-pentoxycarbonyl.

N-Lower alkyl- or N,N-di-lower alkyl-carbamoyl is, for example, N-methylcarbamoyl, N-ethylcarbamoyl, N,N-dimethylcarbamoyl or N,N-diethylcarbamoyl, whilst N-lower alkylsulphamoyl represents, for example, N-methylsulphamoyl or N,N-dimethylsulphamoyl.

A carboxyl or sulpho present in the form of an alkali metal salt is, for example, a carboxyl or sulpho present in the form of a sodium or potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, thia-lower alkyleneamino is, for example, thiomorpholino, and aza-lower alkyleneamino is, for example piperazino or 4-methylpiperazino. Acylamino in particular represents carbamoylamino, lower alkylcarbamoylamino, such as methylcarbamoylamino, ureidocarbonylamino, guanidinocarbonylamino, lower alkoxycarbonylamino, for example methoxycarbonylamino, ethoxycarbonylamino or tert.-butoxycarbonylamino, halogeno-lower alkoxycarbonylamino, such as 2,2,2-trichloroethoxycarbonylamino, phenyl-lower alkoxycarbonylamino, such as 4-methoxybenzyloxycarbonylamino, lower alkanoylamino, such as acetylamino or propionylamino, and also phthalimido, or sulphoamino optionally present in the form of a salt, such as in the form of an alkali metal salt, for example in the form of a sodium salt or ammonium salt.

Lower alkanoyl is, for example, formyl, acetyl, propionyl or pivaloyl.

O-Lower alkyl-phosphono is, for example O-methyl- or O-ethyl-phosphono, O,O'-di-lower alkyl-phosphono is, for example, O,O-dimethyl-phosphono or O,O'-diethylphosphono, O-phenyl-lower alkyl-phosphono is, for example, O-benzyl-phosphono, and O-lower alkyl-O'-phenyl-lower alkyl-phosphono is, for example, O-benzyl-O'-methyl-phosphono.

Lower alkenyloxycarbonyl is, for example, vinyloxycarbonyl, whilst cycloalkoxycarbonyl and phenyl-lower alkoxycarbonyl represent, for example, adamantyloxycarbonyl, benzyloxycarbonyl, 4-methoxy-benzyloxycarbonyl, diphenylmethoxycarbonyl or α-4-biphenyl-α-methyl-ethoxycarbonyl. Lower alkoxycarbonyl, wherein lower alkyl contains, for example, a monocyclic, monoazacyclic, monooxacyclic or monothiacyclic group, is, for example, furyl-lower alkoxycarbonyl, such as furfuryloxycarbonyl, or thienyl-lower alkoxycarbonyl, such as 2-thenyloxycarbonyl.

2-Lower alkylhydrazino and 2,2-di-lower alkylhydrazino are, for example, 2-methylhydrazino or 2,2-dimethylhydrazino, 2-lower alkoxycarbonylhydrazino is, for example, 2-methoxycarbonylhydrazino, 2-ethoxycarbonylhydrazino or 2-tert.-butoxycarbonylhydrazino and lower alkanoylhydrazino is, for example, 2-acetylhydrazino.

An acyl group Ac in particular represents an acyl radical of an organic carboxylic acid, preferably with up to 18 carbon atoms, contained in a naturally occurring or biosynthetically, semi-synthetically or total-synthetically obtainable, preferably pharmacologically active, N-acyl derivative of a 6-amino-penam-3-carboxylic acid compound or 7-amino-3-cephem-4-carboxylic acid compound, or represents an easily removable acyl radical, especially of a carbonic acid half-derivative.

An acyl radical Ac contained in a pharmacologically active N-acyl derivative of a 6-amino-penam-3-carboxylic acid compound or 7-amino-3-cephem-4-carboxylic acid compound is above all a group of the formula

(A), wherein n represents O and $R^I$ denotes hydrogen or an optionally substituted cycloaliphatic or aromatic hydrocarbon radical or an optionally substituted heterocyclic radical, preferably of aromatic character, a functionally modified, for example esterified or etherified, hydroxyl or mercapto group or an optionally substituted amino group, or wherein n represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, on optionally functionally modified, preferably etherified or esterified, hydroxyl or mercapto group, an optionally functionally modified carboxyl group, an acyl group, an optionally substituted amino group or an azido group and each of the radicals $R^{II}$ and $R^{III}$ denotes hydrogen, or wherein n represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably has aromatic character, $R^{II}$ denotes an optionally functionally modified, for example esterified or etherified, hydroxyl or mercapto group, such as a halogen atom, an optionally substituted amino group, an optionally functionally modified carboxyl or sulpho group, an optionally O-monosubstituted or O,O'-disubstituted phosphono group or an azido group and $R^{III}$ represents hydrogen, or wherein n represents 1, each of the radicals $R^I$ and $R^{III}$ denotes a functionally modified, preferably etherified or esterified, hydroxyl group or an optionally functionally modified carboxyl group, and $R^{III}$ represents hydrogen, or wherein n represents 1, $R^I$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cycloaliphatic, cycloaliphatic-aliphatic or araliphatic hydrocarbon radical which is bonded to the carbon atom by a double bond, or wherein n represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

In the abovementioned acyl groups of the formula A, for example, n represents O and $R^I$ represents hydrogen or a cycloalkyl group with 5–7 ring carbon atoms which is optionally substituted, preferably in the 1-position, by optionally protected amino, acylamino, wherein acyl above all represents the acyl radical of a carbonic acid half-ester, such as a lower alkoxycarbonyl, 2-halogeno-lower alkoxycarbonyl or phenyl-lower alkoxycarbonyl radical, or a sulphoamino group which is optionally present in the form of a salt, for example in the form of an alkali metal salt, a phenyl, naphthyl or tetrahydronaphthyl group which is optionally substituted, preferably by hydroxyl, lower alkoxy, for example methoxy, acyloxy, wherein acyl above all represents the acyl radical of a carbonic acid half-ester, such as a lower alkoxycarbonyl, 2-halogeno-lower alkoxycarbonyl or phenyl-lower alkoxycarbonyl radical, and/or halogen, for example chlorine, a heterocyclic group which is optionally substituted, for example by lower alkyl, for example methyl and/or phenyl, which can in turn carry substituents, such as halogen, for example chlorine, such as a 4-isoxazolyl group, or an amino group which is preferably N-substituted, for example by an optionally substituted lower alkyl radical, such as a lower alkyl radical containing halogen, for example chlorine, or n represents 1, $R^I$ represents a lower alkyl group which is optionally substituted, preferably by halogen, such as chlorine, by phenyloxy which is optionally substituted, such as phenyloxy containing hydroxyl, acyloxy, wherein acyl has the abovementioned meaning, and/or halogen, for example chlorine, or by optionally protected amino and/or carboxyl, for example a 3-amino-3-carboxypropyl radical which has an optionally protected amino and/or carboxyl group, for example a silylated, such as tri-lower alkylsilylated, for example trimethylsilylated, amino or acylamino, such as lower alkanoylamino, halogeno-lower alkanoylamino or phthaloylamino group, and/or a silylated, such as tri-lower alkylsilylated, for example trimethylsilylated, carboxyl group, or an esterified carboxyl group, such as a carboxyl group which is esterified by lower alkyl, 2-halogeno-lower alkyl or phenyl-lower alkyl, for example diphenylmethyl, or represents a lower alkenyl group, a phenyl group which is optionally substituted, such as a phenyl group which optionally contains hydroxyl which is acylated, for example as indicated above, and/or halogen, for example chlorine, and also amino-lower alkyl, such as aminomethyl, which is optionally protected, for example acylated as indicated above, or phenyloxy, which possesses hydroxyl which is optionally acylated, for example as indicated above, and/or halogen, for example chlorine, or represents a pyridyl group, for example 4-pyridyl group, pyridinium group, for example 4-pyridinium group, thienyl group, for example 2-thienyl group, furyl group, for example 2-furyl group, imidazolyl group, for example 1-imidazolyl group, or tetrazolyl group, for example 1-tetrazolyl group, which are optionally substituted, for example by lower alkyl, such as methyl, or by amino or aminomethyl which are optionally protected, for example acylated as indicated above, or represents an optionally substituted lower alkoxy group, for example a methoxy group, a phenyloxy group which is optionally substituted, such as a phenyloxy group which contains optionally protected hydroxyl, for example hydroxyl acylated as indicated above, and/or halogen, such as chlorine, or represents a lower alkylthio group, for example n-butylthio group, or lower alkenylthio group, for example allylthio group, a phenylthio, pyridylthio, for example 4-pyridylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol-3-ylthio, 1,3,4-thiadiazol-2-ylthio, such as methyl-1,3,4-thiadiazol-2-yl-thio, or 5-tetrazolylthio, such as 1-methyl-5-tetrazolylthio group, which are optionally substituted, for example by lower alkyl, such as methyl, or represents a halogen atom, especially chlorine or bromine atom, an optionally functionally modified carboxyl group, such as lower alkoxycarbonyl, for example methoxycarbonyl or ethoxycarbonyl, nitrile or carbamoyl which is optionally N-substituted, for example by lower alkyl, such as methyl or phenyl, or represents an optionally substituted lower alkanoyl group, for example an acetyl or propionyl group, or a benzoyl group, or an azido group, and $R^{II}$ and $R^{III}$ represent hydrogen, or n represents 1, $R^I$ represents lower alkyl or a phenyl, furyl, for example 2-furyl, thienyl, for example 2- or 3-thienyl, or isothiazolyl, for example 4-isothiazolyl group which is optionally substituted, such as substituted by hydroxyl which is optionally acylated, for example as indicated above, and/or by halogen, for example chlorine, and also represents a 1,4-cyclohexadienyl group, $R^{II}$ represents optionally protected or substituted amino, for example amino, acylamino, such as lower alkoxycarbonylamino, 2-halogeno-lower alkoxycarbonylamino or optionally substituted phenyl-lower alkoxycarbonylamino such as phenyl-lower alkoxycarbonylamino which contains lower alkoxy, for example methoxy, or nitro, for example tert.-butoxycarbonylamino, 2,2,2-trichloroethoxycarbonylamino, 4-methoxybenzyloxycarbonylamino or diphenylmethyloxycarbonylamino, arylsulphonylamino, for example 4-methylphenylsulphonylamino, tritylamino, arylthioamino, such as nitrophenylthioamino, for example 2-nitrophenylthioamino, or tritylthioamino or 2-propylideneamino which is optionally substituted, such as 2-propylideneamino which contains lower alkoxycarbonyl, for example ethoxycarbonyl, or lower alkanoyl, for example acetyl, such as 1-ethoxycarbonyl-2-propylideneamino, or optionally substituted carbamoylamino, such as guanidinocarbonylamino, or a sulphoamino group which is optionally present in the form of a salt, for example in the form of an alkali metal salt, an azido group, a carboxyl group which is optionally present in the form of a salt, for example in the form of an alkali metal salt, or in a protected form, such as in as esterified form, for example as a lower alkoxycarbonyl group, for example a methoxycarbonyl group or ethoxycarbonyl group, or as a phenyloxycarbonyl group, for example a diphenylmethoxycarbonyl group, a nitrile group, a sulpho group, an optionally functionally modified hydroxyl group, wherein functionally modified hydroxyl in particular represents acyloxy, such as formyloxy, as well as lower alkoxycarbonyloxy, 2-halogeno-lower alkoxycarbonyloxy or phenyl-lower alkoxycarbonyloxy which is optionally substituted, such as phenyl-lower alkoxycarbonyloxy which contains lower alkoxy, for example methoxy, or nitro, for example tert.-butoxycarbonyloxy, 2,2,2-trichloroethoxycarbonyloxy, 4-methoxybenzyloxycarbonyloxy or diphenylmethoxycarbonyloxy, or optionally substituted lower alkoxy, for example methoxy or phenyloxy, a O-lower alkyl-phosphono group or O,O'-di-lower alkyl-phosphono group, for example O-methyl-phosphono or O,O'-dimethylphosphono, or a halogen atom, for example chlorine or bromine, and $R^{III}$ represents hydrogen, or n represents 1, $R^I$ and $R^{II}$ each represent halogen, for example bromine, or lower alkoxycarbonyl, for example methoxycarbonyl, and $R^{III}$ represents hydrogen, or n represents 1, $R^I$ represents a phenyl, furyl, for example 2-furyl, or thienyl, for example 2- or 3-thienyl, or isothiazolyl, for example 4-isothiazolyl, group, which are optionally substituted, for example by hydroxyl which is optionally acylated, for example as indicated above, and/or by halogen, for example chlorine, and also represents a 1,4-cyclohexadienyl group, $R^{II}$ represents aminomethyl which is optionally protected, for example as indicated above, and $R^{III}$ represents hydrogen or n represents 1 and each of the groups $R^I$, $R^{II}$ and $R^{III}$ represents lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group optionally present in the form of a salt, or an amino group which is substituted by an acyl radical which can be split off, preferably easily, for example on treatment with an acid agent, such as trifluoroacetic acid, or by reduction, for example on treatment with a chemical reducing agent, such as zinc in the presence of aqueous acetic acid, or catalytic hydrogen, or hydrolytically, or an acyl radical which can be converted into such a radical, preferably a suitable acyl radical of a carbonic acid half-ester, such as lower alkoxycarbonyl, for example tert.-butoxycarbonyl, 2-halogen-lower alkylcarbonyl, for example 2,2,2-trichloroethoxycarbonyl, 2-bromoethoxycarbonyl or 2-iodoethoxycarbonyl, arylcarbonylmethoxycarbonyl, for example phenacyloxycarbonyl, optionally substituted phenyl-lower alkoxycarbonyl, such as phenyl-lower alkoxycarbonyl containing lower alkoxy, for example methoxy or nitro, for example 4-methoxybenzyloxycarbonyl or diphenylmethoxycarbonyl, or of a carbonic acid half-amide, such as carbamoyl or N-substituted carbamoyl, such as N-lower alkylcarbamoyl, for example N-methylcarbamoyl, as well as by trityl, also by arylthio, for example 2-nitrophenylthio, arylsulphonyl, for example 4-methylphenylsulphonyl or 1-lower alkoxycarbonyl-2-propylidene, for example 1-ethoxycarbonyl-2-propylidene), 2,6-dimethoxybenzoyl, 5,6,7,8-tetrahydronaphthoyl, 2-methoxy-1-naphthoyl, 2-ethoxy-1-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, pivaloyl, hexanoyl, octanoyl, acrylyl, crotonyl, 3-butenoyl, 2-pentenoyl, methoxyacetyl, butylthioacetyl, allylthioacetyl, methylthioacetyl, chloroacetyl, bromoacetyl, dibromoacetyl, 3-chloropropionyl, 3-bromopropionyl, aminoacetyl or 5-amino-5-carboxy-valeryl (with an amino group which is optionally substituted, for example as indicated, such as substituted by a monoacyl or diacyl radical, for example an optionally halogenated lower alkanoyl radical, such as acetyl or dichloroacetyl, or phthaloyl, and/or with an optionally functionally modified carboxyl group, for example a carboxyl group present in the form of a salt, such as a sodium salt, or in the form of an ester, such as a lower alkyl ester, for example a methyl or ethyl ester, or an aryl-lower alkyl ester, for example diphenylmethyl ester), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethylacrylyl, phenylacetyl, α-bromophenylacetyl, α-azidophenylacetyl, 3-chlorophenylacetyl, 2- or 4-aminomethylphenyl-acetyl (with an amino group which is optionally substituted, for example, as indicated), phenacylcarbonyl, phenoxyacetyl, 4-trifluoromethylphenoxyacetyl, benzyloxyacetyl, phenylthioacetyl, bromophenylthioacetyl, 2-phenoxypropionyl, α-phenoxyphenylacetyl, α-methoxyphenylacetyl, α-ethoxyphenylacetyl, α-methoxy-3,4-dichlorophenylacetyl, α-cyano-phenylacetyl, especially phenylglycyl, 4-hydroxyphenylglycyl, 3-chloro-4-hydroxyphenylglycyl, 3,5-dichloro-4-hydroxy-phenylglycyl, α-amino-α-(1,4-cyclohexadienyl)-acetyl, α-amino-α-(1-cyclohexenyl)-acetyl, α-aminomethyl-α-phenylacetyl or α-hydroxyphenylacetyl, (it being possible, in these radicals, for an amino group which is present to be optionally substituted, for example as indicated above, and/or an aliphatic and/or phenolically bonded hydroxyl group which is present to be optionally protected, analogously to the amino group, for example by a suitable acyl radical, especially by formyl or by an acyl radical of a carbonic acid half-ester), or α-O-methyl-phosphono-phenylacetyl or α-O,O-dimethyl-phosphono-phenylacetyl, also benzylthioacetyl, benzylthiopropionyl, α-carboxyphenylacetyl (with a carboxyl group which is optionally functionally modified, for example as indicated above), 3-phenylpropionyl, 3-(3-cyanophenyl)-propionyl, 4-(3-methoxyphenyl)-butyryl, 2-pyridylacetyl, 4-amino-pyridiniumacetyl (optionally with an amino group which is substituted, for example as indicated above), 2-thienylacetyl, 3-thienylacetyl, 2-tetrahydrothienylacetyl, 2-furylacetyl, 1-imidazolylacetyl, 1-tetrazolylacetyl, α-carboxy-2-thienylacetyl or α-carboxy-3-thienylacetyl (optionally with a carboxyl group which is functionally modified, for example as indicated above), α-cyano-2-thienylacetyl, α-amino-α-(2-thienyl)-acetyl, α-amino-α-(2-furyl)-acetyl or α-amino-α-(4-isothiazolyl)-acetyl (optionally with an amino group which is substituted, for example as indicated above), α-sulphophenylacetyl (optionally with a sulpho group which is functionally modified, for example like the carboxyl group), 3-methyl-2-imidazolylthioacetyl, 1,2,4-triazol-3-yl-thioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical Ac, especially of a carbonic acid half-ester, is above all an acyl radical of a half-ester of carbonic acid which can be split off by reduction, for example on treatment with a chemical reducing agent, or by treatment with acid, for example with trifluoroacetic acid, such as a lower alkoxycarbonyl group which preferably has multiple branching and/or an aromatic substituent on the carbon atom in the α-position to the oxy group, or a methoxycarbonyl group which is substituted by arylcarbonyl, especially benzoyl, radicals, or a lower alkoxycarbonyl radical which is substituted in the β-position by halogen atoms, for example tert.-butoxycarbonyl, tert.-pentoxycarbonyl, phenacyloxycarbonyl, 2,2,2-trichloroethoxycarbonyl or 2-Iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyllower alkoxycarbonyl, above all α-phenyl-lower alkoxycarbonyl, wherein the α-position is preferably polysubstituted, for example diphenylmethoxycarbonyl, or α-4-diphenylyl-α-methylethoxycarbonyl, or furyl-lower alkoxycarbonyl, above all α-furyl-lower alkoxycarbonyl, for example furfuryloxycarbonyl.

A bivalent acyl group formed by the two radicals $R_1^A$ and $R_1^b$ is, for example, the acyl radical of a lower alkanedicarboxylic acid or lower alkenedicarboxylic acid, such as succinyl, or an o-arylenedicarboxylic acid, such as phthaloyl.

A further bivalent radical formed by the groups $R_1^A$ and $R_1^b$ is, for example, a 1-oxo-3-aza-1,4-butylene radical which is substituted, especially in the 2-position and contains, for example, optionally substituted phenyl or thienyl, and is optionally monosubstituted or disubstituted by lower alkyl, such as methyl, in the 4-position, for example 4,4-dimethyl-2-phenyl-1-oxo-3-aza-1,4-butylene.

An etherified hydroxyl group $R_2^A$ forms, together with the carbonyl grouping, an esterified carboxyl group which can preferably be split easily or can be converted easily into another functionally modified carboxyl group, such as into a carbamoyl or hydrazinocarbonyl group. Such a group $R_2^A$ is, for example, lower alkoxy, such as methoxy, ethoxy, n-propoxy or isopropoxy, which, together with the carbonyl grouping, forms an esterified carboxyl group, which can easily be converted, especially in 2-cephem compounds, into a free carboxyl group or into another functionally modified carboxyl group.

An etherified hydroxyl group $R_2^A$ which together with a —C(=O)— grouping forms an esterified carboxyl group which can be split particularly easily represents, for example, 2-halogeno-lower alkoxy, wherein halogen preferably has an atomic weight above 19. Such a radical forms, together with the —C(=O)— grouping an esterified carboxyl group which can easily be split on treatment with chemical reducing agents under neutral or weakly acid conditions, for example with zinc in the presence of aqueous acetic acid, or an esterified carboxyl group which can easily be converted into such a group and is, for example, 2,2,2-trichloroethoxy or 2-iodoethoxy, also 2-chloroethoxy or 2-bromoethoxy, which can easily be converted into the latter.

An etherified hydroxyl group $R_2^A$ which together with the —C(=O)— grouping represents an esterified carboxyl group which can also be split on treatment with chemical reducing agents under neutral or weakly acid conditions, for example on treatment with zinc in the presence of aqueous acetic acid, and also on treatment with a suitable nucleophilic reagent, for example sodium thiophenolate, is an arylcarbonylmethoxy group, wherein aryl in particular represents an optionally substituted phenyl group, and preferably phenacyloxy.

The group $R_2^A$ can also represent an arylmethoxy group wherein aryl in particular denotes a monocyclic, preferably substituted, aromatic hydrocarbon radical. Such a radical forms, together with the —C(=O)— grouping, an esterified carboxyl group which can easily be split on irradiation, preferably with ultraviolet light, under neutral or acid conditions. An aryl radical in such an arylmethoxy group is in particular lower alkoxyphenyl, for example methoxyphenyl (wherein methoxy above all is in the 3-, 4- and/or 5-position) and/or above all nitrophenyl (wherein nitro is preferably in the 2-position). Such radicals are, in particular, lower alkoxy-benzyloxy, for example methoxy-benzyloxy, and/or nitrobenzyloxy, above all 3- or 4-methoxybenzyloxy, 3,5-dimethoxy-benzyloxy, 2-nitro-benzyloxy or 4,5-dimethoxy-2-nitro-benzyloxy.

An etherified hydroxyl group $R_2^A$ can also represent a radical which, together with the —C(=O)— grouping forms an esterified carboxyl group which can easily be split under acid conditions, for example on treatment with trifluoroacetic acid or formic acid. Such a radical is above all a methoxy group in which methyl is polysubstituted by optionally substituted hydrocarbon radicals, especially aliphatic or aromatic hydrocarbon radicals, such as lower alkyl, for example methyl, and/or phenyl, or is monosubstituted by a carbocyclic aryl group possessing electron-donating substituents or by a heterocyclic group of aromatic character possessing oxygen or sulphur as a ring member, or in which methyl denotes a ring member in a polycycloaliphatic hydrocarbon radical or denotes the ring member which represents the α-position to the oxygen or sulphur atom in an oxacycloaliphatic or thiacycloaliphatic radical.

Preferred polysubstituted methoxy groups of this nature are tert.-lower alkoxy, for example tert.-butoxy or tert.-pentoxy, optionally substituted diphenylmethoxy, for example diphenylmethoxy or 4,4'-dimethoxydiphenylmethoxy, and also 2-(4-biphenylyl)-2-propoxy, whilst a methoxy group which contains the abovementioned substituted aryl group or the heterocyclic group is, for example, α-lower alkoxyphenyl-lower alkoxy, such as 4-methoxybenzyloxy or 3,4-dimethoxybenzyloxy, or furfuryloxy, such as 2-furfuryloxy. A polycycloaliphatic hydrocarbon radical in which the methyl of the methoxy group represents a branched, preferably triply branched, ring member, is, for example, adamantyl, such as 1-adamantyl, and an abovementioned oxacycloaliphatic or thiacycloaliphatic radical wherein the methyl of the methoxy group is the ring member which represents the α-position to the oxygen atom or sulphur atom, denotes, for example, 2-oxa- or 2-thia-lower alkylene or -lower alkenylene with 5-7 ring atoms, such as 2-tetrahydrofuryl, 2-tetrahydropyranyl or 2,3-dihydro-2-pyranyl or corresponding sulphur analogues.

The radical $R_2^A$ can also represent an etherified hydroxyl group which, together with the —C(=O)— grouping forms an esterified carboxyl group which can be split hydrolytically, for example under weakly basic or weakly acid conditions. Such a radical is, preferably, an etherified hydroxyl group which forms an activated ester group with the —C(=O)— grouping, such as nitrophenyloxy, for example 4-nitrophenyloxy or 2,4-dinitrophenyloxy, nitrophenyl-lower alkoxy, for example 4-nitro-benzyloxy, hydroxy-lower alkylbenzyloxy, for example 4-hydroxy-3,5-tert.-butyl-benzyloxy, polyhalogenophenyloxy, for example 2,4,6-trichlorophenyloxy or 2,3,4,5,6-pentachlorophenyloxy, and also cyanomethoxy, as well as acylaminomethoxy, for example phthaliminomethoxy or succinyliminomethoxy.

The group $R_2^A$ can also represent an etherified hydroxyl group which, together with the carbonyl grouping of the formula —C(=O)—, forms an esterified carboxyl group which can be split under hydrogenolytic conditions and is, for example, α-phenyl-lower alkoxy, which is optionally substituted, for example by lower alkoxy or nitro, such as benzyloxy, 4-methoxybenzyloxy or 4-nitrobenzyloxy.

The group $R_2^A$ can also be an etherified hydroxyl group which, together with the carbonyl grouping —C(=O)—, forms an esterified carboxyl group which can be split under physiological conditions, above all an acyloxymethoxy group, wherein acyl denotes, for example, the radical of an organic carboxylic acid, above all of an optionally substituted lower alkanecarboxylic acid, or wherein acyloxymethyl forms the residue of a lactone. Hydroxyl groups etherified in this way are lower alkanoyloxymethoxy, for example acetoxymethoxy or pivaloyloxymethoxy, amino-lower alkanoyloxymethoxy, especially α-amino-lower alkanoyloxymethoxy, for example glycyloxymethoxy, L-valyloxymethoxy, L-leucyloxymethoxy and also phthalidyloxy.

A silyloxy or stannyloxy group $R_2^A$ preferably contains, as substituents, optionally substituted aliphatic, cycloaliphatic, aromatic or araliphatic hydrocarbon radicals, such as lower alkyl, halogeno-lower alkyl, cycloalkyl, phenyl or phenyl-lower alkyl groups, or optionally modified functional groups, such as etherified hydroxyl groups, for example lower alkoxy groups, or halogen atoms, for example chlorine atoms, and above all represents tri-lower alkylsilyloxy, for example trimethylsilyloxy, halogeno-lower alkoxy-lower alkylsilyl, for example chloromethoxymethylsilyl, or tri-lower alkylstannyloxy, for example tri-n-butylstannyloxy.

An acyloxy radical $R_2^A$ which, together with a —C(=O)— grouping, forms a mixed anhydride group which can be split, preferably hydrolytically, contains, for example, the acyl radical of one of the abovementioned organic carboxylic acids or carbonic acid half-derivatives and is, for example, lower alkanoyloxy which is optionally substituted, such as by halogen, for example fluorine or chlorine, preferably in the α-position, for example acetoxy, pivalyloxy or trichloroacetoxy, or lower alkoxycarbonyloxy, for example methoxycarbonyloxy or ethoxycarbonyloxy.

A radical $R_2^A$ which, together with a —C(=O)— grouping, forms an optionally substituted carbamoyl or hydrazino-carbonyl group is, for example, amino, lower alkylamino or dilower alkylamino, such as methylamino, ethylamino, dimethylamino or diethylamino, lower alkyleneamino, for example pyrrolidino or piperidino, oxa-lower alkyleneamino, for example morpholino, hydroxylamino, hydrazino, 2-lower alkylhydrazino or 2,2-di-lower alkylhydrazino, for example 2-methylhydrazino or 2,2-dimethylhydrazino.

A lower alkyl group $R_3$ with up to 7, preferably with up to 4, carbon atoms is preferably methyl, or ethyl n-propyl, hexyl or heptyl.

The 2-oxa-aliphatic or -cycloaliphatic or 2-thiaaliphatic or -cycloaliphatic hydrocarbon radical $R_3$ is above all a 1-lower alkoxy-1-lower alkyl or 1-lower alkylthio-1-lower alkyl radical, such as 1-methoxy-1-ethyl, 1-ethoxy-1-ethyl, 1-methylthio-1-ethyl or 1-ethylthio-1-ethyl, or a 2-oxa- or 2-thia-lower alkylene or -lower alkenylene radical, with 5–7 ring atoms, such as 2-tetrahydrofuryl, 2-tetrahydropyranyl or 2,3-dihydro-2-pyranyl or a corresponding analogous sulphur compound.

Easily removable silyl or stanhyl groups $R_3$ are preferably sustituted by optionally substituted aliphatic, cycloaliphatic, aromatic or araliphatic hydrocarbon radicals, such as lower alkyl, halogeno-lower alkyl, cycloalkyl, phenyl or phenyl-lower alkyl groups, or optionally functionally modified groups, such as etherified hydroxyl groups, for example lower alkoxy groups, or halogen atoms, for example chlorine atoms. Representative examples of such groups are above all tri-lower alkylsilyl, such as trimethylsilyl, halogeno-lower alkoxy-lower alkylsilyl, such as chloromethoxymethylsilyl, or tri-lower alkylstannyl, such as tri-n-butylstannyl.

Further easily removable hydroxyl protective groups $R_3$ are, for example, α-phenyl-lower alkyl, such as benzyl and diphenylmethyl, wherein possible substituents of the phenylnuclei are, for example, esterified or etherified hydroxyl such as halogen, for example fluorine, chlorine or bromine, or lower alkoxy, such as methoxy.

Salts are, in particular, those of compounds of the formulae IA and IB having an acid grouping, such as a carboxyl, sulpho or phosphono group, above all metal salts or ammonium salts, such as alkali metal salts and alkaline earth metal salts, for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzylethylenediamine, and also bases of the pyridine type, for example pyridine, collidine or quinoline. Compounds of the formulae IA and IB which possess a basic group can also form acid addition salts, for example with inorganic acids, such as hydrochloric acid, sulphuric acid or phosphoric acid, or with suitable organic carboxylic acids or sulphonic acids, for example trifluoroacetic acid or p-toluenesulphonic acid. Compounds of the formulae IA and IB having an acid group and a basic group can also be in the form of inner salts, that is to say in the form of a zwitter-ion. 1-Oxides of compounds of the formula IA having salt-forming groups can also form salts, as described above.

The compounds of the present invention possess valuable pharmacological properties or can be used as intermediate products for the manufacture of such compounds. Compounds of the formula Ia wherein, for example, $R_1^a$ represents an acyl radical Ac occurring in pharmacologically active N-acyl derivatives of 6β-amino-penam-3-carboxylic acid compounds or 7β-amino-3-cephem-4-carboxylic acid compounds and $R_1^b$ represents hydrogen, or wherein $R_1^a$ and $R_1^b$ together represent a 1-oxo-3-1,4-butylene radical which is preferably substituted in the 2-position, for example by an aromatic or heterocyclic radical, and preferably substituted in the 4-position, for example by 2 lower alkyl, such as methyl, $R_2$ denotes hydroxyl or an etherified hydroxyl group $R_2^A$ which, together with the carbonyl group, forms an esterified carboxyl group which can easily be split under physiological conditions, and $R_3$ denotes lower alkyl, and functional groups which may be present in an acyl radical $R_1^a$, such as amino, carboxyl, hydroxyl and/or sulpho, are usually in the free form, or salts of such compounds having salt-forming groups, are effective, on parenteral and/or oral administration, against micro-organisms such as Gram-positive bacteria, for example *Staphylococcus aureus, Streptococcus pyogenes* and *Diplococcus pneumoniae* (for example in mice at doses of about 0.001 to about 0.02 g/kg s.c. or p.o.), and Gram-negative bacteria, for example, *Escherichia coli, Salmonella typhimurium, Shigella flexneri, Klebsiella pneumoniae, Enterobacter cloacae, Proteus vulgaris, Proteus rettgeri* and *Proteus mirabilis* (for example in mice in doses of about 0.001 to about 0.15 g/kg s.c. or p.o.), and especially also against penicillin-resistant bacteria, and are of low toxicity. These new compounds can therefore be used, for example in the form of antibiotically active preparations, for the treatment of corresponding infections.

Compounds of the formula IB or 1-oxides of compounds of the formula IA, wherein $R_1^a$, $R_1^b$, $R_2$ and $R_3$ have the meanings indicated in the context of the formula IA, or compounds of the formula IA, wherein $R_3$ has the abovementioned meaning, the radicals $R_1^a$ and $R_1^b$ represent hydrogen, or $R_1^a$ denotes an amino protective group different from an acyl radical occurring in pharmacologically active N-acyl derivatives of 6β-amino-penam-3-carboxylic acid compounds or 7β-amino-3-cephem-4-carboxylic acid compounds and $R_1^b$ denotes hydrogen, or $R_1^a$ and $R_1^b$ together represent a bivalent amino protective group different from a 1-oxo-3-aza-1,4-butylene radical which is preferably substituted in 2-position, for example by an aromatic or heterocyclic radical, and preferably substituted in the 4-position, for example by 2 lower alkyl, such as methyl, and $R_2$ represents hydroxyl, or $R_1^a$ and $R_1^b$ have the abovementioned meanings, $R_2$ represents a radical $R_2^A$ which together with the —C(=O)— grouping forms a protected carboxyl group which can preferably be split easily, a carboxyl group protected in this way being different from a carboxyl group which can be split physiologically, and $R_3$ has the abovementioned meanings, are valuable intermediate products, which can be converted in a simple manner, for example as is described below, into the abovementioned pharmacologically active compounds.

The invention in particular relates to the manufacture of 3-cephem compounds of the formula IA, wherein $R_1^a$ denotes hydrogen or preferably an acyl radical contained in a fermentatively obtainable (that is to say naturally occurring) or biosynthetically, semi-synthetically or total-synthetically obtainable, in particular pharmacologically active, such as highly active, N-acyl derivative of a 6β-amino-penam-3-carboxylic acid compound or 7β-amino-3-cephem-4-carboxylic acid compound, such as one of the abovementioned acyl radicals of the formula A, in which $R^I$, $R^{II}$, $R^{III}$ and n above all have the preferred meanings, $R_1^b$ represents hydrogen, or $R_1^a$ and $R_1^b$ together represent a 1-oxo-3-aza-1,4-butylene radical which is preferably substituted in the 2-position, for example by an aromatic or heterocyclic radical, such as phenyl, and preferably substituted in the 4-position, for example by two lower alkyl, such as methyl, $R_2$ represents hydroxyl, lower alkoxy which is optionally monosubstituted or polysubstituted, preferably in the α-position, for example by optionally substituted aryloxy, such as lower alkoxyphenyloxy, for example 4-methoxyphenyloxy, lower alkanoyloxy, for example acetoxy or pivaloyloxy, α-amino-lower alkanoyloxy, for example glycyloxy, L-valyloxy or L-leucyloxy, arylcarbonyl, for example benzoyl, or optionally substituted aryl, such as phenyl, lower alkoxyphenyl, for example 4-methoxyphenyl, nitrophenyl, for example 4-nitrophenyl, or biphenylyl, for example 4-biphenylyl, or is monosubstituted or polysubstituted in the β-position by halogen, for example chlorine, bromine or iodine, such as lower alkoxy, for example methoxy, ethoxy, n-propoxy, isopropoxy, n-butoxy, tert.-butoxy or tert.-pentoxy, bis-phenyloxy-methoxy which is optionally substituted by lower alkoxy, for example bis-4-methoxyphenyloxy-methoxy, lower alkanoyloxy-methoxy, for example acetoxymethoxy or pivaloyloxymethoxy, α-amino-lower alkanoyloxymethoxy, for example glycyloxymethoxy, phenacyloxy, optionally substituted phenyl-lower alkoxy, especially 1-phenyl-lower alkoxy, such as phenylmethoxy, with such radicals being able to contain 1-3 phenyl radicals which are optionally substituted, for example by lower alkoxy, such as methoxy, nitro or phenyl, for example benzyloxy, 4-methoxy-benzyloxy, 2-biphenylyl-2-propoxy, 4-nitro-benzyloxy, diphenylmethoxy, 4,4'-dimethoxy-diphenylmethoxy or trityloxy, or 2-halogeno-lower alkoxy, for example 2,2,2-trichloroethoxy, 2-chloroethoxy, 2-bromoethoxy or 2-iodoethoxy, and also 2-phthalidyloxy, as well as acyloxy, such as lower alkoxycarbonyloxy, for example methoxycarbonyloxy or ethoxycarbonyloxy, or lower alkanoyloxy, for example acetoxy or pivaloyloxy, tri-lower alkylsilyloxy, for example trimethylsilyloxy, or amino or hydrazino which is optionally substituted, for example, by lower alkyl, such as methyl, or hydroxyl, for example amino, lower alkylamino or di-lower alkylamino, such as methylamino or dimethylamino, hydrazino, 2-lower alkylhydrazino or 2,2-di-lower alkylhydrazino, for example 2-methylhydrazino or 2,2-dimethylhydrazino, or hydroxyamino, and $R_3$ represents hydrogen, lower alkyl, especially methyl or a hydroxyl protective group, such as tri-lower alkylsilyl, for example trimethylsilyl, or benzyl or diphenylmethyl which are optionally substituted, for example by halogen or lower alkoxy, as well as the 1-oxides thereof, and also the corresponding 2-cephem compounds of the formula IB, or salts of such compounds with salt-forming groups.

Above all, in a 3-cephem compound of the formula IA, and in a corresponding 2-cephen compound of the formula IB, and also in a 1-oxide of a 3-cephem compound of the formula IA, or in a salt of such a compound having salt-forming groups, $R_1^a$ represents hydrogen or an acyl radical contained in fermentatively obtainable (that is to say naturally occurring) or biosynthetically obtainable N-acyl derivatives of 6β-amino-penam-3-carboxylic acid compounds or 7β-amino-3-cephem-4-carboxylic acid compounds, especially of the formula A, wherein $R^I$, $R^{II}$ and $R^{III}$ and n above all have the preferred meanings, such as a phenylacetyl or phenyloxyacetyl radical which is optionally substituted, for example by hydroxyl, also a lower alkanoyl or lower alkenoyl radical which is optionally substituted, for example by lower alkylthio, or lower alkenylthio, as well as by optionally substituted, such as acylated, amino and/or functionally modified, such as esterified, carboxyl, for example 4-hydroxy-phenylacetyl, hexanoyl, octanoyl or n-butylthioacetyl, and especially 5-amino-5-carboxy-valeryl, wherein the amino and/or the carboxyl groups are optionally protected and are present, for example, as acylamino or esterified carboxyl, phenylacetyl or phenyloxyacetyl, or an acyl radical occurring in highly active N-acyl derivatives of 6β-amino-penam-3-carboxylic acid compounds or 7β-amino-3-cephem-4-carboxylic acid compounds, especially of the formula A, wherein $R^I$, $R^{II}$, $R^{III}$ and n above all have the preferred meanings, such as formyl, 2-halogenothylcarbamoyl, for example 2-chloroethylcarbomoyl, cyanoacetyl, phenylacetyl, thienylacetyl, for example 2-thienylacetyl, or tetrazolylacetyl, for example 1-tetrazolylacetyl, but especially acetyl substituted in the α-position by a cyclic, such as a cycloaliphatic, aromatic or heterocyclic, above all monocyclic, radical and by a functional group, above all amino, carboxyl, sulpho or hydroxyl groups, especially phenylglycyl, wherein phenyl represents phenyl which is optionally substituted, for example by optionally protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxy-phenyl (optionally also with a protected hydroxyl group, such as an acylated hydroxyl group), and wherein the amino group can also optionally be substituted and represents, for example, a sulphoamino group optionally present in the form of a salt, or an amino group which contains, as substituents, a hydrolytically removable trityl group or above all an acyl group, such as an optionally substituted carbamoyl group, such as an optionally substituted ureidocarbonyl group, for example ureidocarbonyl or N'-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or reductively, such as on treatment with a chemical reducing agent, such as zinc in the presence or aqueous acetic acid, or with catalytic hydrogen, or hydrolytically, or an acyl radical which can be converted into such a radical, preferably a suitable acyl radical of a carbonic acid half-ester, such as one of the above-mentioned, for example optionally halogen-substituted or benzoyl-substituted, lower alkoxycarbonyl radicals, for example tert.-butoxycarbonyl, 2,2,2-trichloroethoxycarbonyl, 2-chloroethoxycarbonyl, 2-bromoethoxycarbonyl, 2-iodoethoxycarbonyl or phenacyloxycarbonyl, optionally lower alkoxy-substituted or nitro-substituted phenyl-lower alkoxycarbonyl, for example 4-methoxy-benzyloxycarbonyl or diphenylmethoxycarbonyl, or a suitable acyl radical of a carbonic acid half-amide, such as carbamoyl or N-methylcarbamoyl, or an arylthio or aryl-lower alkylthio radical which can be split off with a nucleophilic reagent, such as hydrocyanic acid, sulphurous acid or thioacetic acid amide, for example 2-nitrophenylthio or tritylthio, an arylsulphonyl radical which can be split off by means of electrolytic reduction, for example 4-methylphenylsulphonyl, or a 1-lower alkoxycarbonyl or 1-lower alkanoyl-2-propylidene radical which can be split off with an acid agent, such as formic acid or aqueous mineral acid, for example hydrochloric acid or phosphoric acid, for example 1-ethoxycarbonyl-2-propylidene, and also α-(1-4, cyclohexadienyl)-glycyl, α-(1-cyclohexenyl)-glycyl, α-thienyl-glycyl, such as α-2- or α-3-thienylglycyl, α-furylglycyl, such as α-2-furylglycyl, α-isothiazolylglycyl, such as α-4-isothiazolyl-glycyl, it being possible for the amino group in such radicals to be substituted or protected, for example as indicated for a phenylglycyl radical, also α-carboxy-phenylacetyl or α-carboxy-thienylacetyl, for example α-carboxy-2-thienylacetyl (optionally with a functionally modified carboxyl group, for example a carboxyl group present in the form of a salt, such as a sodium salt, or in the form of an ester, such as a lower alkyl ester, for example methyl or ethyl ester, or phenyl-lower alkyl ester, for example diphenylmethyl ester), α-sulpho-phenylacetyl (optionally also with a sulpho group which is functionally modified, for example like the carboxyl group), α-phosphono-, α-O-methyl-phosphono- or α-O,O'-dimethyl-phosphono-phenylacetyl, or α-hydroxy-phenylacetyl (optionally with a functionally modified hydroxyl group, especially with an acyloxy group, wherein acyl denotes an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as one of the abovementioned lower alkoxycarbonyl radicals which are, for example, optionally substituted by halogen or benzoyl, for example 2,2,2-trichlroethoxycarbonyl, 2-chloroethoxycarbonyl, 2-bromoethoxycarbonyl, 2-iodoethoxycarbonyl, tert.-butoxycarbonyl or phenacyloxycarbonyl, and also formyl), as well as 1-amino-cyclohexylcarbonyl, aminomethylphenylacetyl, such as 2- or 4-aminomethylphenylacetyl, or amino-pyridiniumacetyl, for example 4-amino-pyridiniumacetyl (optionally also with an amino group which is substituted, for example as indicated above), or pyridylthioacetyl, for example 4-pyridylthioacetyl, and $R_1^b$ represents hydrogen, or $R_1^a$ and $R_1^b$ together represent a 1-oxo-3-aza-1,4-butylene radical which is preferably substituted in the 2-position by phenyl which is optionally substituted by protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxy-phenyl (optionally also with a hydroxyl group which is protected, for example acylated as indicated above), and which optionally contains two lower alkyl, such as methyl, in the 4-position, and $R_2$ represents hydroxyl, lower alkoxy, especially α-poly-branched lower alkoxy, for example tert.-butoxy, also methoxy or ethoxy, 2-halogeno-lower alkoxy, for example 2,2,2-trichloroethoxy, 2-iodoethoxy or 2-chloroethoxy or 2-bromoethoxy which can easily be converted into 2-iodoethoxy, phenacyloxy, 1-phenyl-lower alkoxy with 1–3 phenyl radicals which are optionally substituted by lower alkoxy or nitro, for example 4-methoxybenzyloxy, 4-nitrobenzyloxy, diphenylmethoxy, 4,4'-dimethoxydiphenylmethoxy or trityloxy, lower alkanoyloxymethoxy, for example acetoxymethoxy or pivaloyloxymethoxy, α-amino-lower alkanoyloxymethoxy, for example glycyloxymethoxy, 2-phthalidyloxymethoxy, lower alkoxycarbonyloxy, for example ethoxycarbonyloxy, or lower alkanoyloxy, for example acetoxy, and also tri-lower alkylsilyloxy, for example trimethylsilyloxy, and $R_3$ represents hydrogen, lower alkyl, especially methyl, or a hydroxyl protective group, such as tri-lower alkylsilyl, for example trimethylsilyl, or benzyl or diphenylmethyl which are optionally substituted, for example by halogen, such as chlorine or bromine, or lower alkoxy, such as methoxy.

The invention above all relates to the manufacture of 3-cephem compounds of the formula IA, wherein $R_1{}^a$ denotes hydrogen or an acyl group of the formula

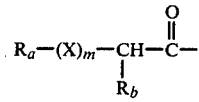
(B)

wherein $R_a$ denotes phenyl or hydroxyphenyl, for example 3- or 4-hydroxyphenyl, also hydroxy-chlorophenyl, for example 3-chloro-4-hydroxyphenyl or 3,5-dichloro-4-hydroxy-phenyl, it being possible for hydroxy substituents in such radicals to be protected by acyl radicals, such as optionally halogenated lower alkoxycarbonyl radicals, for example tert.-butoxycarbonyl or 2,2,2-trichloroethoxycarbonyl, as well as thienyl, for example 2- or 3-thienyl, and also pyridyl, for example 4-pyridyl, aminopyridinium, for example 4-aminopyridinium, furyl, for example 2-furyl, isothiazolyl, for example 4-isothiazolyl, or tetrazolyl, for example 1-tetrazolyl, or 1,4-cyclohexadienyl or 1-cyclohexenyl, X represents oxygen or sulphur, m represents 0 or 1 and $R_b$ represents hydrogen, or, if m represents O, $R_b$ represents amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino or diphenylmethoxycarbonylamino, or 3-guanylureido, also sulphoamino or tritylamino, as well as arylthioamino, for example 2-nitrophenylthioamino, arylsulphonylamino, for example 4-methylphenylsulphonylamino, or 1-lower alkoxycarbonyl-2-propylidene amino, for example 1-ethoxycarbonyl-2-propylideneamino, carboxyl, or carboxyl present in the form of a salt, for example an alkali metal salt, such as a sodium salt, as well as protected carboxyl, for example esterified carboxyl, such as phenyl-lower alkoxycarbonyl, for example diphenylmethoxycarbonyl, sulpho, or sulpho present in the form of a salt, for example an alkali metal salt, such as a sodium salt, as well as protected sulpho, hydroxyl, as well as protected hydroxyl, such as acyloxy, for example α-poly-branched lower alkoxycarbonyloxy, such as tert.-butoxycarbonyloxy or 2-halogeno-lower alkoxycarbonyloxy, such as 2,2,2-trichloroethoxycarbonyloxy, 2-iodoethoxycarbonyloxy or 2-bromoethoxycarbonyloxy, also formyloxy, or O-lower alkylphosphono or O,O'-di-lower alkylphosphono, for example O-methyl-phosphono or O,O'-dimethylphosphono, or denotes a 5-amino-5-carboxy-valeryl radical, wherein the amino and/or carboxyl groups can also be protected and are, for example, present as acylamino, for example lower alkanoylamino, such as acetylamino, halogeno-lower alkanoylamino such as dichloroacetylamino, benzoylamino or phthaloylamino, or as esterified carboxyl, such as phenyl-lower alkoxycarbonyl, for example diphenylmethoxycarbonyl, and m preferably denotes 1 if $R_a$ represents phenyl, hydroxyphenyl, hydroxychlorophenyl or pyridyl, and m denotes O and $R_b$ differs from hydrogen if $R_a$ represents phenyl, hydroxyphenyl, hydroxy-chlorophenyl, thienyl, furyl, isothiazolyl, 1,4-cyclohexadienyl or 1-cyclohexenyl, $R_1{}^b$ denotes hydrogen, $R_2$ above all represents hydroxyl and also represents lower alkoxy, especially α-poly-branched lower alkoxy, for example tert.-butoxy, 2-halogeno-lower alkoxy, for example 2,2,2-trichloroethoxy, 2-iodoethoxy or 2-bromoethoxy, or diphenylmethoxy which is optionally substituted, for example, by lower alkoxy, for example methoxy, for example diphenylmethoxy or 4,4'-dimethoxydiphenylmethoxy, as well as tri-lower alkylsilyloxy, for example trimethylsilyloxy, and $R_3$ denotes hydrogen, lower alkyl, for example methyl, ethyl or n-butyl, as well as tri-lower alkylsilyl, for example trimethylsilyl, and benzyl or diphenylmethyl which is optionally substituted for example by halogen, such as chlorine or bromine, or lower alkoxy, such as methoxy, as well as the 1-oxides of such 3-cephem compounds of the formula IA, and also the corresponding 2-cephem compounds of the formula IB, or salts, especially pharmaceutically usable, non-toxic salts, of such compounds having salt-forming groups, such as alkali metal salts, for example sodium salts, or alkaline earth metal salts, for example calcium salts, or ammonium salts, including those with amines, of compounds wherein $R_2$ represents hydroxyl, and which contain a free amino group in the acyl radical of the formula B.

Above all, in 3-cephem compounds of the formula IA, and also in corresponding 2-cephem compounds of the formula IB, as well as in salts, especially in parmaceutically usable non-toxic salts, of such compounds which have salt-forming groups, as in the salts mentioned in the preceding paragraph, $R_1{}^a$ represents hydrogen, the acyl radical of the formula B wherein $R_a$ denotes phenyl, as well as hydroxyphenyl, for example 4-hydroxy-phenyl, thienyl, for example 2- or 3-thienyl, 4-isothiazolyl, 1,4-cyclohexadienyl or 1-cyclohexenyl, x denotes oxygen, m denotes O or 1 and $R_b$ denotes hydrogen, or, if m represents O, denotes amino, as well as protected amino, such as acylamino, for example α-poly-branched lower alkoxycarbonylamino, such as tert.-butoxycarbonylamino, or 2-halogeno-lower alkoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino, or hydroxyl, as well as protected hydroxyl, such as acyloxy, for example α-polybranched lower alkoxycarbonyloxy, such as tert.-butoxy-carbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or represents a 5-amino-5-carboxy-valeryl radical, wherein the amino and carboxyl group can also be protected and, for example, are in the form of acylamino, for example lower alkanoylamino, such as acetylamino, halogeno-lower alkanoylamino, such as dichloroacetylamino, benzoylamino or phthaloylamino, or of esterified carboxyl, such as phenyl-lower alkoxycarbonyl, for example diphenylmethoxycarbonyl, with m preferably denoting 1, if $R_a$ is phenyl or hydroxyphenyl, $R_1{}^b$ represents hydrogen, $R_2$ above all denotes hydroxyl and also lower alkoxy which is optionally halogen-substituted, for example chlorine-substituted, bromine-substituted or iodine-substituted, in the 2-position, especially α-poly-branched lower alkoxy, or example tert.-butoxy, or 2-halogeno-lower alkoxy, for example 2,2,2-trichloroethoxy, such as methoxy-substituted diphenylmethoxy, for example diphenylmethoxy or 4,4'-dimethoxy-diphenylmethoxy, or p-nitrobenzyloxy, and also tri-lower alkylsilyloxy, for example trimethylsilyloxy, and $R_3$ denotes hydrogen, lower alkyl, especially methyl, tri-lower alkylsilyl, for example trimethylsilyl, or a benzyl or diphenylmethyl group which is optionally substituted by halogen, for example chlorine or bromine, or lower alkoxy, for example methoxy.

The invention above all relates to the manufacture of 7β-(D-α-amino-α-$R_a$-acetylamino)-3-lower alkoxy-3-cephem-4-carboxylic acids, wherein $R_a$ represents phenyl, 4-hydroxyphenyl, 2-thienyl, 1,4-cyclohexadienyl or 1-cyclohexenyl and lower alkoxy contains up to 4 carbon atoms and represents, for example, ethoxy or n-butoxy, but above all methoxy, and the inner salts thereof, and above all 3-methoxy-7β-(D-α-phenylglycylamino)-3-cephem-4carboxylic acid and the inner salt thereof; in the abovementioned concentrations, especially on oral administration, these compounds display excellent antibiotic properties both against Gram-positive and especially against Gram-negative bacteria, and are of low toxicity.

According to the process of the invention, compounds of the formula IA, their 1-oxides, compounds of the formula IB and salts of such compounds, having salt-forming groups, are manufactured by treating a compound of the formula

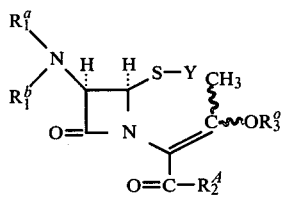

(II)

wherein $R_1{}^a$, $R_1{}^b$ and $R_2{}^A$ have the meanings mentioned under formula IA, $R_3{}^o$ represents lower alkyl or a hydroxyl protective group, and Y represents a group which is removed, with a base, and, if desired, in a resulting compound of the formula IA or IB, converting the protected carboxyl group of the formula —C(=O)—$R_2{}^A$ into the free carboxyl group or into another protected carboxyl group, and/or, if desired, converting the protected hydroxyl group —O—$R_3{}^o$ into a free hydroxyl group and/or converting the resulting free hydroxyl group or the protected hydroxyl group —O—$R_3{}^o$ into a lower alkoxy group —O—$R_3$, and/or, is desired, within the definition of the end products, converting a resulting compund into another compound and/or, if desired, converting a resulting compound having a salt-forming group into a salt or converting a resulting salt into the free compound or into another salt and/or, if desired, separating a resulting mixture of isomeric compunds into the individual isomers.

In a compound of the formula II, the group —O—$R_3{}^o$ can be in the trans-position (crotonic acid configuration) or in the cis-position (isocrotonic acid configuration) relative to the carboxyl group.

In a starting compound of the formula II, a group Y which is removed is, for example, a —S—$R_4$ group, a —S—$R_4$ group, a —$SO_2$—$R_5$ group bonded by the sulphur atom to the thio group —S—, or a —S—$SO_2R_5$ group.

In the group —S—$R_4$, $R_4$ is an optionally substituted aromatic heterocyclic radical with up to 15, preferably up to 9, carbon atoms, and at least one ring nitrogen atom and optionally a further ring hetero-atom, such as oxygen or sulphur, which radical is bonded to the thio group —S— by one of its ring carbon atoms, which is bonded to a ring nitrogen atom by a double bond. Such radicals are monocyclic or bicyclic and can be substituted, for example by lower alkyl, such as methyl or ethyl, lower alkoxy, such as methoxy or ethoxy, halogen, such as fluorine or chlorine, or aryl, such as phenyl.

Such radicals $R_4$ are, for example, monocyclic five-membered thiadiazacyclic, thiatriazacyclic, oxadiazacyclic or oxatriazacyclic radicals of aromatic character, but especially monocyclic five-membered diazacyclic, oxazacyclic and thiazacyclic radicals of aromatic character, and/or, above all, the corresponding benzdiazacyclic, benzoxazacyclic or benzthiazacyclic radicals, wherein the heterocyclic part is five-membered and is of aromatic character, and in radicals $R_4$ a substitutable ring nitrogen atom can be substituted, for example, by lower alkyl. Representative examples of such groups $R_4$ are 1-methyl-imidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 2-quinolyl, 1-methyl-benzimidazol-2-yl, benzoxazol-2-yl and especially benzthiazol-2-yl. Further groups $R_4$ are acyl radicals of organic carboxylic acids or thiocarboxylic acids, such as optionally substituted aliphatic, cycloaliphatic, araliphatic or aromatic acyl or thioacyl groups with up to 18, preferably with up to 10, carbon atoms, such as lower alkanoyl, for example acetyl or propionyl, lower thioalkanoyl, for example thioacetyl or thiopropionyl, cycloalkanecarboxyl, for example cyclohexanecarbonyl, cycloalkanethiocarbonyl, for example cyclohexanethiocarbonyl, benzoyl, thiobenzoyl, naphthylcarbonyl, naphthylthiocarbonyl, heterocyclic carbonyl or thiocarbonyl, such as 2-, 3- or 4-pyridylcarbonyl, 2- or 3-thenoyl, 2- or 3-furoyl, 2-, 3- or 4-pyridylthiocarbonyl, 2- or 3-thiothenoyl, or 2- or 3-thiofuroyl, or corresponding substituted acyl or thioacyl groups, for example acyl or thioacyl groups monosubstituted or polysubstituted by lower alkyl, such as methyl, halogen, such a fluorine or chlorine, lower alkoxy, such as methoxy, aryl, such as phenyl, or aryloxy, such as phenyloxy.

In the groups —$SO_2$-$R_5$ and —S—$SO_2R_5$, $R_5$ is an optionally substituted, especially an aliphatic, cycloaliphatic, araliphatic or aromatic, hydrocarbon radical with up to 18, preferably with up to 10, carbon atoms. Suitable groups $R_5$ are, for example, optionally substituted, such as lower alkoxy-, such as methoxy-, halogen-, such as fluorine-, chlorine- or bromine-, aryl-, such as phenyl-, or aryloxy-, such as phenyloxy-monosubstituted or -polysubstituted alkyl groups, especially lower alkyl groups, such as methyl, ethyl or butyl groups, alkenyl groups, such as allyl or butenyl groups, cycloalkyl groups, such as cyclopentyl or cyclohexyl groups, or naphthyl or especially phenyl groups which are optionally monosubstituted or polysubstituted by lower alkyl, such as methyl, lower alkoxy, such as methoxy, halogen, such as fluorine, chlorine or bromine, aryl, such as phenyl, aryloxy, such as phenyloxy, or nitro, for example phenyl, o-, m- or preferably p-tolyl, o-, m- or preferably p-methoxyphenyl, o-, m- or p-chlorophenyl, p-biphenylyl, p-phenoxyphenyl, p-nitrophenyl or 1- or 2-naphthyl.

In a starting material of the formula II, $R_2{}^A$ preferably represents an etherified hydroxyl group which, with the —C(=O)- grouping, forms an esterified carboxyl group which can be split, especially under mild conditions, it being possible for functional groups which may be present in a carboxyl protective group $R_2^A$ to be protected in a manner which is in itself known, for example as indicated above. A group $R_2^A$ is, for example, in particular an optionally halogen-substituted lower alkoxy group, such as methoxy, α-poly-branched lower alkoxy, for example tert.-butoxy, or 2-halogeno-lower alkoxy, wherein halogen represents, for example, chlorine, bromine or iodine, above all 2,2,2-trichloroethoxy, 2-bromoethoxy, or 2-iodoethoxy, or an optionally substituted 1-phenyl-lower alkoxy group, such as a 1-phenyl-lower alkoxy group which contains lower alkoxy, for example methoxy, or nitro, such as benzyloxy or diphenylmethoxy which are optionally substituted, for example as indicated, for example benzyloxy, 4-methoxybenzyloxy, 4-nitrobenzyloxy, diphenylmethoxy or 4,4'-dimethoxy-diphenylmethoxy, and also an organic silyloxy or stannyloxy group, such as tri-lower alkylsilyloxy, for example trimethylsilyloxy, or halogen, for example chlorine. Preferably, in a starting material of the formula II, the radical $R_1^a$ denotes an amino protective group $R_1^A$, such as an acyl group Ac, in which free functional groups which may be present, for example amino, hydroxyl, carboxyl or phosphono groups, can be protected in a manner which is in itself known, amino groups, for example, by the abovementioned acyl, trityl, silyl or stannyl radicals as well as substituted thio or sulphonyl radicals, and hydroxyl, carboxyl or phosphono groups, for example, by the abovementioned ether or ester groups, including silyl or stannyl groups, and $R_1^b$ denotes hydrogen.

In a starting material of the formula II, $R_3^a$ preferably denotes lower alkyl, especially methyl, or, as a hydroxyl protective group, preferably a substituted silyl group, especially the trimethylsilyl group, as well as an α-phenyl-lower alkyl group, such as the benzyl or diphenylmethyl group.

Suitable bases for the cyclisation reaction are, in particular, strong organic or inorganic bases. Bases to be singled out particularly are bicyclic amidines, such as diazabicycloalkenes, for example 1,5-diazabicyclo[4.3.0]non-5-ene or 1,5-diazabicyclo[5.4.0]undec-5-ene, substituted guanidines, for example guanidines polysubstituted by lower alkyl, such as tetramethylguanidine, and also metal bases, such as hydride, amides or alcoholates of alkali metals, especially of lithium, sodium or potassium, for example sodium hydride, lithium di-lower alkylamides, such as lithium diisopropylamide and potassium lower alkanolates, such as potassium tert.-butylate. Compounds of the formula II, in which $R_2^A$ denotes halogen, for example chlorine, can also be cyclised with a tertiary oranic nitrogen base, for example a tri-lower alkylamine, such as triethylamine, and in the presence of an alcohol, such as a lower alkanol, for example tert.-butanol, the corresponding ester of the formula IA and/or IB can be obtained.

The reaction according to the invention is carried out in a suitable inert solvent, for example in an aliphatic, cycloaliphatic or aromatic hydrocarbon, such as hexane, cyclohexane, benzene or toluene, a halogenated hydrocarbon, such as methylene chloride, an ether, such as a di-lower alkyl ether, for example diethyl ether, a di-lower alkoxy-lower alkane, such as dimethoxyethane, a cyclic ether, such as dioxane or tetrahydrofurane, or a lower alkanol, for example methanol, ethanol or tert.-butanol, or a mixture thereof, at room temperature or with slight warming to 40°-50°, if desired in an inert gas atmosphere, such as a nitrogen atomsphere.

When treating a compound of the formula II, wherein Y denotes a —S—$R_4$ group, for example the 2-benzthiazolylthio radical, with one of the bases mentioned, for example with 1,5-diazabicyclo[5.4.0]undec-5-ene, the yield of compounds of the formula IA and IB can be increased by adding a sulphinic acid of the formula H—$SO_2$—$R_5$, for example p-toluenesulphinic acid.

In the cyclisation reaction according to the invention it is possible, depending on the starting material and reaction conditions, to obtain single compounds of the formula IA or IB or mixtures of compounds of the formula IA and IB. Suitable mixtures can be separated in a manner which is in itself known, for example with the aid of suitable methods of separation, for example by absorption and fractional elution, including chromatography (column, paper or plate chromatography) using suitable adsorbents, such as silica gel or aluminium oxide, and eluting agents, and also by fractional crystallisation, solvent distribution and the like.

Resulting compounds of the formulae IA and IB which are suitable intermediates for the manufacture of pharmacologically more active end products can be converted into such active end products by various additional measures which are in themselves known.

In a compound, obtainable according to the invention, of the formulae IA or IB, a hydroxyl protective group $R_3$ can easily be split off and replaced by hydrogen. A 2-oxa-aliphatic or -cycloaliphatic or 2-thia-aliphatic or -cycloaliphatic hydrocarbon radical can, for example, be split off by acid hydrolysis and a silyl or stannyl group by hydrolysis, alcoholysis or acidolysis, for example by treatment with water or with an alcohol, such as methanol or ethanol, or with an acid, such as acetic acid.

The splitting off of an optionally substituted α-phenyl-lower alkyl group, for example benzyl group or diphenylmethyl group, is effected, for example, by acidolysis, for example by treatment with a suitable inorganic or organic acid, such as hydrochloric acid, sulphuric acid, formic acid or especially trifluoroacetic acid, or by hydrogenolysis, for example by treatment with hydrogen in the presence of a catalyst, such as palldium. The resulting 3-hydroxy compounds are in the main in the 3-cephem form. The splitting off of a hydroxyl protective group $R_3$ can optionally be carried out selectively, that is to say without a carboxyl protective group $R_2^A$ being split off at the same time.

Enol-ethers, that is to say compounds of the formula IA and/or IB, wherein $R_3$ represents lower alkyl, are obtained from compounds of the formulae IA or IB, wherein $R_3$ is a radical which protects hydroxyl groups, by replacing this radical by hydrogen and subsequently etherifying the free hydroxyl group in accordance with any process suitable for the etherification of enol groups. Preferably, the etherifying reagent used is a diazo compound of the formula $R_3$-$N_2$ corresponding to the optionally substituted hydrocarbon radical $R_3$, above all an optionally substituted diazo-lower alkane, for example diazomethane, diazoethane or diazo-n-butane, or an optionally substituted α-phenyl-diazo-lower alkane, for example phenyldiazomethane or diphenyldiazomethane. These reagents are used in the presence of a suitable inert solvent, such as an aliphatic, cycloaliphatic or aromatic hydrocarbon, such as hexane, cyclohexane, benzene or toluene, of a halogenated aliphatic hydrocarbon, for example methylene chloride, of a lower alkanol, for example methanol, ethanol or tert.-butanol, or of an ether, such as of a di-lower alkylether, for example diethyl ether, or of a cyclic ether, for example tetrahydrofurane or dioxane, or of a solvent mixture and, depending on the diazo reagent, with cooling, at room temperature or with slight warming and also, if necessary, in a closed vessel and/or under an inert gas atmosphere, for example a nitrogen atmosphere.

Furthermore, enol-ethers of the formula IA and/or IB can be formed by treatment with a reactive ester of an alcohol of the formula $R_3$—OH which corresponds to the lower alkyl radical or the optionally substituted α-phenyl-lower alkyl, for example benzyl or diphenylmethyl, radical $R_3$. Suitable esters are above all those with strong inorganic or organic acids, such as mineral acids, for example hydrogen halide acids, such as hydrochloric acid, hydrobromic acid or hydriodic acid, also sulphuric acid or halogeno-sulphuric acids, for example fluorosulphuric acid, or strong organic sulphonic acids, such as lower alkanesulphonic acids which are optionally substituted, for example by halogen, such as fluorine, or aromatic sulphonic acids, such as, for example, benzene-sulphonic acids which are optionally substituted, for example by lower alkyl, such as methyl, halogen, such as bromine, and/or nitro, for example methanesulphonic acid, trifluoromethanesulphonic acid or p-toluenesulphonic acid. These reagents, especially di-lower alkyl sulphates, such as dimethyl sulphate, and also lower alkyl fluorosulphates, for example methyl fluorosulphate, or optionally halogensubstituted methanesulphonic acid lower alkyl esters, for example trifluoromethanesulphonic acid methyl ester, are usually employed in the presence of a solvent, such as of an optionally halogenated, such as chlorinated, aliphatic, cycloaliphatic or aromatic hydrocarbon, for example methylene chloride, of an ether, such as dioxane or tetrahydrofurane, or of a lower alkanol, such as methanol, or of a mixture. At the same time, suitable condensation agents are preferably employed, such as alkali metal carbonates or bicarbonates, for example sodium carbonate or bicarbonate or potassium carbonate or bicarbonate (usually together with a sulphate) or organic bases such as, usually sterically hindered, tri-lower alkylamines, for example N,N-diisopropyl-N-ethyl-amine (preferably together with lower alkyl halogenosulphates or optionally halogen-substituted methanesulphonic acid lower alkyl esters), the reaction being carried out with cooling, at room temperature or with warming, for example at temperatures of about −20° C. to about 50° C. and, if necessary, in a closed vessel and/or in an inert gas atmosphere, for example a nitrogen atmosphere.

Enol-ethers can also be manufactured by treatment with a compound containing two or three etherified hydroxyl groups of the formula $R_3$—O— on the same carbon atom of aliphatic character, that is to say by treatment with an appropriate acetal or ortho-ester, in the presence of an acid agent. Thus, for example, it is possible to use, as etherifying agents, gem-lower alkoxy-lower alkanes, such as 2,2-dimethoxy-propane, in the presence of a strong organic sulphonic acid, such as p-toluenesulphonic acid, and of a suitable solvent, such as of a lower alkanol, for example methanol, or of a di-lower alkylsulphoxide or lower alkylenesulphoxide, for example dimethylsulphoxide, or orthoformic acid tri-lower alkyl esters, for example orthoformic acid tri-ethyl ester, in the presence of a strong mineral acid, for example sulphuric acid or of a strong organic sulphonic acid, such as p-toluenesulphonic acid, and of a suitable solvent, such as of a lower alkanol, for example ethanol, or of an ether, for example dioxane, and thus to arrive at compounds of the formula IA and/or IB, wherein $R_3$ represents lower alkyl, for example methyl or ethyl.

The enol-ethers of the formula IA and/or IB can also be obtained if starting substances of the formula II are treated with tri-$R_3$-oxonium salts of the formula $(R_3)_3 O^\oplus A^\ominus$ (so-called Meerwein salts), as well as di-$R^3O$-carbenium salts of the formula $(R_3O)_2CH^\oplus A^\ominus$ or di-$R_3$halonium salts of the formula $(R_3)_2Hal^\oplus A^\ominus$, wherein $A^\ominus$ denotes the anion of an acid and $Hal^\oplus$ denotes a halonium ion, especially a bromonium ion. The salts concerned are above all tri-lower alkyloxonium salts, as well as di-lower alkoxycarbenium salts or di-lower alkylhalonium salts, especially the appropriate salts with complex acids containing fluorine, such as the appropriate tetrafluoroborates, hexafluophosphates, hexafluoantimonates or hexachloroantimonates. Such reagents are, for example, trimethyloxonium or triethyloxonium hexafluoantimonate, hexachloroantimonate, hexafluophosphate or tetrafluoborate, dimethoxycarbenium hexafluophosphate or dimethylbromonium hexafluoantimonate. These etherifying agents are preferably used in an inert solvent such as an ether or a halogenated hydrocarbon, for example diethyl ether, tetrahydrofurane or methylene chloride, or in a mixture thereof, if necessary in the presence of a base, such as of an organic base, for example of a preferably sterically hindered tri-lower alkylamine, for example N,N-diisorpopyl-N-ethyl-amine, and with cooling, at room temperature or with slight warming, for example at about −20° C. to about 50° C., if necessary in a closed vessel and/or in an inert gas atmosphere, for example a nitrogen atmosphere.

The enol-ethers of the formulae IA and/or IB can also be manufactured by treating starting substances of the formula II with a 3-substituted or 1—$R_3$-triazene compound (that is to say a compound of the formula Subst. —N=N—NH—$R_3$), the substituent of the 3-nitrogen atom denoting an organic radical bonded via a carbon atom, preferably a carbocyclic aryl radical, such as an optionally substituted phenyl radical, for example lower alkylphenyl, such as 4-methyl-phenyl. Such triazene compounds are 3-aryl-1-lower alkyl-triazenes, for example 3-(4-methylphenyl)-1-methyl-triazine, 3-(4-methylphenyl)-1-ethyl-triazine, 3-(4-methylphenyl)-1-n-propyltriazine or 3-(4-methylphenyl)-1-isopropyl-triazene, and also 3-aryl-1-(α-phenyl-lower alkyl)-triazenes, for example 1-benzyl-3-(4-methyl-phenyl)-triazine. These reagents are usually employed in the presence of inert solvents, such as optionally halogenated hydrocarbons or ethers, for example benzene or solvent mixtures, and with cooling, at room temperature and preferably at elevated temperature, for example at about 20° C. to about 100° C., if necessary in a closed vessel and/or in an inert gas atmosphere, for example a nitrogen atmosphere.

In the process according to the invention, and in additional measures which may require to be carried out it is possible, if necessary, temporarily to protect, in a manner which is in itself known, free functional groups, which do not participate in the reaction, in the starting substances, or in the compounds obtainable according to the process, for example free amino groups by, for example, acylation, tritylation or silylation, free hydroxyl or mercapto groups by, for example, etherification or esterification, and free carboxyl groups by, for example, esterification, including silylation and in each case to liberate them after the reaction has taken place, if desired, individually or conjointly, in a manner which is in itself known. Thus it is preferably possible, for example, to protect amino, hydroxyl, carboxyl or phosphono groups in an acyl radical $R_1^A$ or $R_1^b$, for example in the form of acylamino groups, such as those mentioned above, for example 2,2,2-trichloroethoxycarbonylamino, 2-bromoethoxycarbonylamino, 4-methoxybenzyloxycarbonylamino, dphenylmethoxycarbonylamino or tert.-butoxycarbonylamino groups, of arylthioamino or aryl-lower alkylthioamino groups, for example 2-nitrophenylthioamino groups, or arylsulphonylamino groups, for example 4-methylphenylsulphonylamino groups, or of 1-lower alkoxycarbonyl-2-propylideneamino groups, or, respectively, or acyloxy groups, such as those mentioned above, for example tert.-butoxycarbonyloxy, 2,2,2-trichloroethoxycarbonyloxy of 2-bromoethoxycarbonyloxy groups, or, respectively, of esterified carboxyl groups, such as those mentioned above, for example diphenylmethoxycarbonyl groups, or, respectively, O,O'-disubstituted phosphono groups, such as those mentioned above, for example O,O'-di-lower alkylphosphono groups, for example O,O'-dimethylphosphono groups and subsequently, optionally after conversion of the protective group, for example of a 2-bromoethoxycarbonyl group into a 2-iodoethoxycarbonyl group, to split the protected group in a manner which is in itself known and depending on the nature of the protective group, for example a 2,2,2-trichloroethoxycarbonylamino or 2-iodoethoxycarbonylamino group by treatment with suitable reducing agents, such as zinc in the presence of aqueous acetic acid, a diphenylmethoxycarbonylamino or tert.-butoxycarbonylamino group by treatment with formic acid or trifluoroacetic acid, an arylthioamino or aryl-lower alkylthioamino group by treatment with a nucleophilic reagent, such as sulphurous acid, an arylsulphonylamino group by means of electrolytic reduction, a 1-lower alkoxycarbonyl-2-propylideneamino group by treatment with an aqueous mineral acid, or a tert.-butoxycarbonyloxy group by treatment with formic acid or trifluoroacetic acid, or a 2,2,2-trichloroethoxycarbonyloxy group by treatment with a chemical reducing agent, such as zinc in the presence of aqueous acetic acid, or a diphenylmethoxycarbonyl group by treatment with formic acid or trifluoroacetic acid or by hydrogenolysis, or an O,O'-disubstituted phosphono group by treatment with an alkali metal halide, the splitting being carried out if desired, for example partially.

In a compound of the formula IA or IB obtainable according to the invention and possessing a protected, especially esterified, carboxyl group of the formula $-C(=O)-R_2^A$, the latter can be converted into the free carboxyl group in a manner which is in itself known, for example depending on the nature of the group $R_2^A$. An esterified carboxyl group, for example a carboxyl group esterified by a lower alkyl radical, especially methyl or ethyl, or by a benzyl radical, especially in a 2-cephem compound of the formula IB, can be converted into a free carboxyl group by hydrolysis in a weakly basic medium, for example by treatment with an aqueous solution of an alkali metal hydroxide or carbonate or alkaline earth metal hydroxide or carbonate, for example sodium hydroxide or potassium hydroxide, preferably at a pH value of about 9 to 10, and optionally in the presence of a lower alkanol. A carboxyl group esterified by a suitable 2-halogeno-lower alkyl group or by an arylcarbonylmethyl group can be split, for example, by treatment with a chemical reducing agent, such as a metal, for example zinc, or a reducing metal salt, such as a chromium-II salt, for example chromium-II chloride, usually in the presence of a hydrogen donor which is capable of producing nascent hydrogen together with the metal, such as an acid, above all acetic acid and also formic acid, or an alcohol, water being added preferably, a carboxyl group esterified by an arylcarbonylmethyl group can also be split by treatment with a nucleophilic, preferably salt-forming, reagent, such as sodium thiophenolate or sodium iodide, a carboxyl group esterified by a suitable arylmethyl grouping can be split, for example, by irradiation, preferably with ultraviolet light, for example below 290 m$\mu$, if the arylmethyl group represents, for example, a benzyl radical which is optionally substituted in the 3-, 4- and-/or 5-position, for example by lower alkoxy and/or nitro groups, or with ultraviolet light of longer wavelengths, for example above 290 m$\mu$, if the arylmethyl group denotes, for example, a benzyl radical which is substituted by a nitro group in the 2-position, a carboxyl group which is esterified by a suitably substituted methyl group, such as tert.-butyl or diphenylmethyl can be split, for example, by treatment with a suitable acid agent, such as formic acid or trifluoroacetic acid, optionally with the addition of a nucleophilic compound, such as phenol or anisole, an activated esterified carboxyl group, and also a carboxyl group present in the form of an anhydride, can be split by hydrolysis for example by treatment with an acid or weakly basic aqueous agent, such as hydrochloric acid or aqueous sodium bicarbonate or an aqueous potassium phosphate buffer or pH about 7 to about 9, and an esterified carboxyl group which can be split hydrogenolytically can be split by hydrogenolysis, for example by treatment with hydrogen in the presence of a noble metal catalyst, for example a palladium catalyst.

A carboxyl group protected, for example, by silylation or stannylation can be liberated in the usual manner, for example by treatment with water or an alcohol.

Resulting compounds of the formula IA or IB can be converted in a manner which is in itself known into other compounds of the formula IA or IB.

In a resulting compound it is possible, for example, to split off an amino protective group $R_1^A$ or $R_1^b$, especially an easily removable acyl group, in a manner which is in itself known, for example an $\alpha$-polybranched lower alkoxycarbonyl group, such as tert.-butoxycarbonyl, by treatment with trifluoroacetic acid, and a 2-halogeno-lower alkoxycarbonyl group, such as 2,2,2-trichloroethoxycarbonyl or 2-iodoethoxycarbonyl or a phenacyloxycarbonyl group, by treatment with a suitable reducing metal or corresponding metal compound, for example zinc, or a chromium-II compound, such as chromium-II chloride or chromium-II acetate, advantageously in the presence of an agent which together with the metal or the metal compound generates nascent hydrogen, preferably in the presence of aqueous acetic acid.

It is furthermore possible, in a resulting compound of the formula IA or IB, wherein a carboxyl group of the formula $-C(=O)-R_2$ preferably represents a carboxyl group which is protected, for example by esterification, including silylation, for example by reaction with a suitable organic halogenosilicon compound or halogeno-tin-IV compound, such as trimethylchlorosilane or tri-n-butyl-tin chloride, to split off an acyl group $R_1^a$ or $R_1^b$, wherein optionally present free functional groups are optionally protected, by treatment with an imide-halide-forming agent, reaction of the resulting imide-halide with an alcohol and splitting of the imino-ether formed, it being possible for a protected carboxyl group, for example a carboxyl group protected by an organic silyl radical, already to be liberated in the course of the reaction.

Imide-halide-forming agents in which halogen is bonded to an electrophilic central atom are above all acid halides, such as acid bromides and especially acid chlorides. The acid halides are above all acid halides or inorganic acids, above all of acids containing phosphorus, such as phosphorus oxyhalides, phosphorus trihalides and especially phosphorus pentahalides, for example phosphorus oxychloride, phosphorus trichloride and above all phosphorus pentachloride, and also pyrocatechyl-phosphorus trichloride, as well as acid halides, especially acid chlorides, of acids containing sulphur or of carboxylic acids, such as thionyl chloride, phosgene or oxalyl chloride.

The reaction with one of the imide-halide-forming agents mentioned is usually carried out in the presence of a suitable base, especially of an organic base, above all of a tertiary amine, for example a tertiary aliphatic monoamide or diamine, such as a tri-lower alkylamine, for example trimethylamine, triethylamine or N,N-diisopropyl-N-ethylamine, also a N,N,N',N'-tetra-lower alkyl-lower alkylenediamine, for example N,N,N',N'-tetramethyl-1,5-pentylenediamine or N,N,N',N'-tetramethyl-1,6-hexylenediamine, a monocyclic or bicyclic monoamine or diamine, such as a N-substituted, for example N-lower alkylated, alkyleneamine, azaalkyleneamine or oxaalkyleneamine, for example N-methyl-piperidine or N-methyl-morpholine, as well as 2,3,4,6,7,8-hexahydro-pyrrolo[1,2-a]pyrimidine (diazabicyclo-nonene; DBN), or a tertiary aromatic amine such as a di-lower alkylaniline, for example N,N-dimethylaniline, or above all a tertiary heterocyclic, monocyclic or bicyclic, base, such as quinoline or isoquinoline, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; the latter can, however, also be present in more than or less than equimolar amount, for example in about 0.2-fold to about 1-fold amount or in, say, up to 10-fold, in particular about 3-fold to 5-fold, excess.

The reaction with the imide-halide-forming agent is preferably carried out with cooling, for example at temperatures of about −50° C. to about +10° C., but it is also possible to work at higher temperatures, that is to say, for example, up to about 75° C., if the stability of the starting substances and of the products permits a higher temperature.

The imide-halide product which is usually further processed without isolation, is reacted according to the process with an alcohol, preferably in the presence of one of the abovementioned bases, to give the imino-ether. Examples of suitable alcohols are aliphatic as well as araliphatic alcohols, above all optionally substituted, such as halogenated, for example chlorinated, lower alkanols or lower alkanols possessing additional hydroxyl groups, for example ethanol, propanol or butanol but especially methanol, also 2-halogeno-lower alkanols, for example 2,2,2-trichloroethanol or 2-bromoethanol, and optionally substituted phenyl-lower alkanols, such as benzyl alcohol. Usually an excess, for example up to about 100-fold excess, of the alcohol is employed and the reaction is preferably carried out with cooling, for example at temperatures of about −50° C. to about 10° C.

The imino-ether product can advantageously be split without isolation. The splitting of the imino-ether can be achieved by treatment with a suitable hydroxy compound, preferably by means of hydrolysis, and also be alcoholysis, and the latter can take place directly following the formation of the imino-ether, if an excess of the alcohol is used. Preferably, water or an alcohol, especially a lower alkanol, for example methanol, or an aqueous mixture of an organic solvent, such as an alcohol, is used. The reaction is usually carried out in an acid medium, for example at a pH value of about 1 to about 5 which can, if necessary, be obtained by adding a basic agent, such as an aqueous alkali metal hydroxide, for example sodium hydroxide or potassium hydroxide, or an acid, for example a mineral acid, or an organic acid, such as hydrochloric acid, sulphuric acid, phosphoric acid, fluoboric acid, trifluoroacetic acid or p-toluenesulphonic acid.

The three-stage process for splitting off an acyl group, described above, is advantageously carried out without isolation of the imide-halide and imino-ether intermediate products, usually in the presence of an organic solvent which is inert towards the reactants, such as an optionally halogenated hydrocarbon, for example methylene chloride, and/or in an inert gas atmosphere, such as a nitrogen atmosphere.

If the imide-halide intermediate product obtained according to the above process, instead of being reacted with an alcohol, is reacted with a salt, such as an alkali metal salt, of a carboxylic acid, especially of a sterically hindered carboxylic acid, a compound of the formula IA or IB, wherein both radicals $R_1^a$ and $R_1^b$ represent acyl groups, is obtained.

In a compound of the formula IA or IB, wherein both radicals $R_1^a$ and $R_1^b$ represent acyl groups, one of these groups, preferably the sterically less hindered group, can be removed selectively, for example by hydrolysis or aminolysis.

In a compound of the formulae IA or IB, wherein $R_1^A$ and $R_1^b$ together with the nitrogen atom represent a phthalimido group, the latter can be converted into the free amino group, for example by hydrazinolysis, that is to say on treatment of such a compound with hydrazine.

Certain acyl radicals $R_1^A$ of an acylamino grouping in compounds obtainable according to the invention such as, for example, the 5-amino-5-carboxy-valeryl radical, wherein carboxyl is optionally protected, for example by esterification, especially by diphenylmethyl, and/or the amino group is optionally protected, for example by acylation, especially by an acyl radical of an organic carboxylic acid, such as halogeno-lower alkanoyl, such as dichloroacetyl, or phthaloyl, can also be split off by treatment with a nitrosylating agent, such as nitrosyl chloride, with a carbocyclic arenediazonium salt, such as benzenediazonium chloride, or with an agent which releases positive halogen, such as a N-halogeno-amide or -imide, for example N-bromosuccinimide, preferably in a suitable solvent or solvent mixture, such as formic acid, together with a nitro- or cyano-lower alkane, and treatment of the reaction product with a hydroxylic agent, such as water or a lower alkanol, for example methanol or, if in the 5-amino-5-carboxy-valeryl radical $R_1^A$ the amino group is substituted and the carboxyl group is protected, for example by esterification, and $R_1^b$ preferably represents an acyl radical but can also denote hydrogen, by leaving the substance to stand in an inert solvent, such as dioxane or a halogenated aliphatic hydrocarbon, for example methylene chloride and, if necessary, working up the free or monoacylated amino compound according to methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group, such as the trityl group $R_1^A$, can be split off, for example by treatment with an acid agent, such as a mineral acid, for example hydrochloric acid.

In a compound of the formula IA or IB, wherein $R_1^a$ and $R_1^b$ represent hydrogen, the free amino group can be substituted according to methods which are in themselves known, above all acylated by treatment with acids, such as carboxylic acids, or reactive derivatives thereof.

If a free acid wherein optionally present functional groups, such as an optionally present amino group, are preferably protected, is employed for the acylation, suitable condensation agents are usually employed, such as carbodiimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyl diimidazole, or isoxazolinium salts, for example N-ethyl-5-phenyl-isoxazolinium-3'-sulphonate and N-tert.-butyl-5-methyl-isoxazolinium perchlorate, or a suitable acylamino compound, for example 2-ethoxy-1-ethoxycarbonyl-1,2-dihydroquinoline.

The condensation reaction is preferably carried out in one of the anhydrous reaction media mentioned later, for example in methylene chloride, dimethylformamide or acetonitrile.

An amide-forming functional derivative of an acid, wherein optionally present groups, such as an optionally present amino group, are preferably protected, is above all an anhydride of such an acid, including, and preferably, a mixed anhydride. Mixed anhydrides are, for example, those with inorganic acids, especially with hydrogen halide acids, that is to say the corresponding acid halides, for example acid chlorides or acid bromides, and also with hydrazoic acid, that is to say the corresponding acid azides, with an acid containing phosphorus, for example phosphoric acid or phosphorous acid, with an acid containing sulphur, for example sulphuric acid, or with hydrocyanic acid. Further mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl half-ester or isobutyl half-ester of carbonic acid, or with organic, especially aliphatic or aromatic, sulphonic acids, for example p-toluenesulphonic acid.

It is furthermore possible to use, as acylating agents, inner anhydrides, such as ketenes, for example diketene, isocyanates, (that is to say inner anhydrides of carbamic acid compounds) or inner anhydrides of carboxylic acid compounds having carboxyl-substituted hydroxyl or amino groups, such as mandelic acid O-carboxanhydride or the anhydride of 1-N-carboxyamino-cyclohexanecarboxylic acid.

Further acid derivatives suitable for reaction with the free amino group are activated esters, wherein optionally present functional groups are usually protected, such as esters with vinylogous alcohols, (that is to say enols), such as vinylogous lower alkanols, or aryl esters, such as phenyl esters which are preferably substituted, for example by nitro or halogen, such as chlorine, for example pentachlorophenyl, 4-nitrophenyl or 2,4-dinitrophenyl esters, hetero-aromatic esters, such as benztriazole esters, or diacylimino esters, such as succinylimino esters or phthalylimino esters.

Further acylation derivatives are, for example, substituted formimino derivatives, such as substituted N,N-dimethylchloroformimino derivatives of acids, or N-substituted N,N-diacylamines, such as a N,N-diacylated aniline.

The acylation with an acid derivative, such as an anhydride, and especially with an acid halide, can be carried out in the presence of an acid-binding agent, for example of an organic base, such as an organic amine, for example a tertiary amine, such as tri-lower alkylamine, for example triethylamine, N,N-di-lower alkylaniline, for example N,N-dimethylaniline, or a base of the pyridine type, for example pyridine, an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or of an oxirane, for example a lower 1,2-alkylene oxide, such as ethylene oxide or propylene oxide.

The above acylation can be carried out in an aqueous or, preferably, non-aqueous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered, or elevated temperature and/or in an inert gas atmosphere, for example a nitrogen atmosphere.

In the above N-acylation reactions it is possible to start from compounds of the formulae IA or IB, wherein $R_3$ is lower alkyl or an optionally substituted α-phenyl-lower alkyl group, for example a benzyl or diphenylmethyl group, and $R_2$ has the above meaning, and compounds having free carboxyl groups of the formula —C(=O)—$R_2$, wherein $R_2$ represents hydroxyl, can also be used in the form of salts, for example ammonium salts, such as with triethylamine, or in the form of a compound with a carboxyl group protected by reaction with a suitable organic phosphorus halide compound, such as with a lower alkyl- or lower alkoxy-phosphorus dihalide, such as methyl-phosphorus dichloride, ethyl-phosphorus dibromide or methoxyphosphorus dichloride; in the resulting acylation product the protected carboxyl group can be liberated in a manner which is in itself known, for example as described above, including by hydrolysis or alcoholysis.

An acyl group can also be introduced by acylating a compound of the formula IA or IB, wherein $R_1^a$ and $R_1^b$ together represent an ylidene radical, (which can also be introduced subsequently, for example by treating a compound wherein $R_1^a$ and $R_1^b$ represent hydrogen, with an aldehyde, such as an aliphatic, aromatic or araliphatic aldehyde), for example according to the methods indicated above, and the acylation product can be hydrolyzed, preferably in a neutral or weakly acid medium.

An acyl group can also be introduced stepwise. Thus, for example, it is possible to introduce into a compound of the formula IA or IB, having a free amino group, a halogeno-lower alkanoyl group, for example a bromoacetyl group, or, for example by treatment with a carbonic acid dihalide, such as phosgene, a halogenocarbonyl group, for example a chlorocarbonyl group, and to react a N-(halogeno-lower alkanoyl)-amino compound or N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol and thus to obtain substituted N-lower alkanoyl-amino or N-hydroxycarbonylamino compounds.

In both reactants, free functional groups can temporarily be protected during the acylation reaction, in a manner which is in itself known and be liberated, after the acylation, by means of methods which are in themselves known, for example as described above.

The acylation can also be effected by replacement of an already existing acyl group by another, preferably sterically hindered, acyl group, for example according to the process described above, by manufacturing the imide-halide compound, treating this with a salt of an acid and splitting off hydrolytically one of the acyl groups present in the product thus obtainable, usually the sterically less hindered acyl group.

It is furthermore possible, for example, to react a compound of the formula IA or IB, wherein $R_1^a$ represents a glycyl group which is preferably substituted in the α-position, such as phenylglycyl, and $R_1^b$ represents hydrogen, with an aldehyde, for example formaldehyde, or a ketone, such as a lower alkanone, for example acetone, and thus to arrive at compounds of the formula IA or IB, wherein $R_1^A$ and $R_1^b$ together with the nitrogen atom represent a 5-oxo-1,3-diaza-cyclopentyl radical which is preferably substituted in the 4-position and is optionally substituted in the 2-position.

In a compound of the formula IA or IB, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-di-lower alkylsilane, lower alkoxy-lower alkyl-dihalogenosilane or tri-lower alkyl-silyl halide, for example dichlorodimethylsilane, methoxy-methyl-dichloro-silane, trimethylsilyl chloride or dimethyl-tert.-butyl-silyl chloride, such silyl halide compounds preferably being used in the presence of a base, for example pyridine, or by treatment with an optionally N-mono-lower alkylated, N,N-di-lower alkylated, N-tri-lower alkylsilylated or N-lower alkyl-N-tri-lower alkyl-silylated N-(tri-lower alkylsilyl)-amine (see, for example, British Pat. No. 1,073,530), or with a silylated carboxylic acid amide, such as a bis-tri-lower alkyl-silylacetamide, for example bis-trimethylsilyl-acetamide or trifluorosilylacetamide, or by treatment with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or with a tri-lower alkyl-tin halide, for example tri-n-butyl-tin chloride (see, for example, Netherlands Published Specification No. 67/11,107).

In a compound of the formula IA or IB, obtainable according to the process, which contains a free carboxyl group of the formula $-C(=O)-R_2$, such a group can be converted into a protected carboxyl group in a manner which is in itself known. Thus esters are obtained, for example, by treatment with a suitable diazo compound, such as a diazo-lower alkane, for example diazomethane or diazobutane, or a phenyl-diazo-lower alkane, for example diphenyldiazomethane, if necessary in the presence of a Lewis acid, such as, for example, boron trifluoride, or by reaction with an alcohol suitable for the esterification reaction, in the presence of an esterifying agent, such as a carbodiimide, for example dicyclohexylcarbodiimide, as well as carbonyldiimidazole, and also with a N,N'-disubstituted O- or S-substituted isourea or isothiourea, wherein a O-substituent and S-substituent are, for example, lower alkyl, especially tert.-butyl, phenyl-lower alkyl or cycloalkyl, and N-substituents or N'-substituents are, for example, lower alkyl, especially isopropyl, cycloalkyl or phenyl, or according to any other known and suitable esterification process, such as reaction of a salt of the acid with a reactive ester of an alcohol and of a strong inorganic acid, or with a strong organic sulphonic acid. Furthermore, acid halides, such as acid chlorides (manufactured, for example, by treatment with oxalyl chloride), activated esters (formed, for example, with N-hydroxy-nitrogen compounds, such as N-hydroxy-succinimide), or mixed anhydrides (obtained, for example, with halogenoformic acid lower alkyl esters, such as chloroformic acid ethyl ester or chloroformic acid isobutyl ester, or with halogenoacetic acid halides, such as trichloroacetic acid chloride) can be converted into an esterified carboxyl group by reaction with alcohols, optionally in the presence of a base, such as pyridine.

In a resulting compound having an esterified grouping of the formula $-C(=O)-R_2$, this grouping can be converted into a different esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

Mixed anhydrides can be manufactured by reacting a compound of the formula IA or IB, having a free carboxyl group of the formula $-C(=O)-R_2$, preferably a salt, especially an alkali metal salt, for example a sodium salt, or ammonium salt, for example triethylammonium salt, thereof, with a reactive derivative, such as a halide, for example the chloride, of an acid, for example a halogenoformic acid lower alkyl ester or a lower alkanecarboxylic acid chloride.

In a compound obtainable according to the process, having a free carboxyl group of the formula —C(=O)-R$_2$, such a group can also be converted into an optionally substituted carbamoyl or hydrazinocarbonyl group, for which preferably reactive functionally modified derivatives, such as the abovementioned acid halides, and generally esters, including also the abovementioned activated esters, or mixed anhydrides of the appropriate acid are reacted with ammonia or amines, including hydroxylamine, or hydrazines.

A carboxyl group protected by an organic silyl or stannyl group can be formed in a manner which is in itself known, for example by treating compounds of the formulae IA or IB, wherein R$_2$ represents hydroxyl, or salts thereof, such as alkali metal salts thereof, for example sodium salts thereof, with a suitable silylating or stannylating agent, such as one of the abovementioned silylating or stannylating agents; see, for example, British Pat. No. 1,073,530 or Netherlands Published Specification No. 67/17,107.

It is furthermore possible to liberate modified functional substituents in groups R$_1^A$, R$_1^b$ and/or R$_2$, such as substituted amino groups, acylated hydroxyl groups, esterified carboxyl groups or O,O'-disubstituted phosphono groups, according to methods which are in themselves known, for example those described above, or functionally to modify free functional substituents in groups R$_1^A$, R$_1^b$ and/or R$_2$, such as free amino, hydroxyl, carboxyl or phosphono groups, according to processes which are in themselves known, for example acylation or esterification or substitution. Thus, for example, an amino group can be converted into a sulphoamino group by treatment with sulphur trioxide, preferably in the form of a complex with an organic base, such as tri-lower alkylamine, for example triethylamine. Furthermore, the reaction mixture obtained by reaction of an acid addition salt of a 4-guanylsemicarbazide with sodium nitrite can be reacted with a compound of the formula IA or IB, wherein, for example, the amino protective group R$_1^A$ represents an optionally substituted glycyl group, and the amino group can thus be converted into a 3-guanylureido group. Further, compounds with aliphatically bonded halogen, for example with an optionally substituted α-bromoacetyl grouping, can be reacted with esters of phosphorous acid, such as tri-lower alkyl-phosphite compounds, and corresponding phosphono compounds can thus be obtained.

Resulting cephem compounds of the formula IA and IB can be converted into 1-oxides of the corresponding 3-cephem compounds of the formula IA by oxidation with suitable oxidising agents, such as those described below. Resulting 1-oxides of 3-cephem compounds of the formula IA can be reduced to the corresponding 3-cephem compounds of the formula IA by reduction with suitable reducing agents such as, for example, those described below. In these reactions it is necessary to ensure that, if necessary, free functional groups are protected and are subsequently again liberated, if desired.

Cephem compounds obtained can be isomerised. Thus, resulting 2-cephem compounds of the formula IB, or resulting mixtures of 2-cephem and 3-cephem compounds, can be converted into the corresponding 3-cephem compounds of the formula IA by isomerising a 2-cephem compound of the formula IB, or a mixture consisting of a 2-cephem and 3-cephem compound, wherein free functional groups can, if appropriate, be protected temporarily, for example as indicated. In this reaction it is possible to use, for example, 2-cephem compounds of the formula IB wherein the group of the formula —C(=O)—R$_2$ represents a free or protected carboxyl group, it also being possible to form a protected carboxyl group during the reaction.

Thus it is possible to isomerise a 2-cephem compound of the formula IB by treating it with a basic agent and isolating the corresponding 3-cephem compound of the formula IA from an equilibrium mixture of the 2- and 3-cephem compounds which may be obtained.

Examples of suitable isomerising agents are organic nitrogen-containing bases, such as tertiary heterocyclic bases of aromatic character, and above all tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N-diisopropyl-N-ethylamine, N-lower alkyl-azacycloalkanes, for example N-methylpiperidine, or N-phenyl-lower alkyl-N,N-di-lower alkyl-amines, for example N-benzyl-N,N-dimethylamine, as well as mixtures thereof, such as the mixture of a base of the pyridine type, for example pyridine, and a N,N,N-tri-lower alkylamine, for example pyridine and triethylamine. Furthermore it is also possible to use inorganic or organic salts of bases, especially of medium strength to strong bases, with weak acids, such as alkali metal salts or ammonium salts of lower alkanecarboxylic acids, for example sodium acetate, triethylammonium acetate or N-methyl-piperidine acetate, as well as other analogous bases or mixtures of such basic agents.

The above isomerisation with basic agents can be carried out for example, in the presence of a derivative of a carboxylic acid which is suitable for forming a mixed anhydride, such as a carboxylic acid anhydride or carboxylic acid halide, for example with pyridine in the presence of acetic anhydride. This reaction is preferably carried out in an anhydrous medium, in the presence or absence of a solvent, such as an optionally halogenated, for example chlorinated, aliphatic, cycloaliphatic or aromatic hydrocarbon, or of a solvent mixture, it being possible for bases used as reactants and liquid under the reaction conditions at the same time also to serve as solvents, if necessary with cooling or heating, preferably in a temperature range of about −30° C. to about +100° C., in an inert gas atmosphere, for example a nitrogen atmosphere, and/or in a closed vessel.

The 3-cephem compounds of the formula IA, thus obtainable, can be separated from 2-cephem compounds of the formula IB which may still be present, in a manner which is in itself known, for example by adsorption and/or crystallisation.

The isomerisation of 2-cephem compounds of the formula IB can also be carried out by oxidising these in the 1-position, if desired separating an isomer mixture of the 1-oxides of 3-cephem compounds of the formula IA which may be obtained, and reducing the 1-oxides of the corresponding 3-cephem compounds of the formula IA, thus obtainable.

Suitable oxidising agents for the oxidation of 2-cephem compounds in the 1-position are inorganic per-acids which have a reduction potential of at least +1.5 volt and which consist of non-metallic elements, organic per-acids or mixtures of hydrogen peroxide and acids, especially organic carboxylic acids, having a dissociation constant of at least $10^{-5}$. Suitable inorganic per-acids are periodic acid and persulphuric acid. Organic per-acids are appropriate percarboxylic acids and persulphonic acids which can be added as such or can be formed in situ by the use of at least one equivalent of hydrogen peroxide and of a carboxylic acid. It is desirable to use a large excess of the carboxylic acid if, for example, acetic acid is used as the solvent. Suitable per-acids are, for example, performic acid, peracetic acid, pertrifluoroacetic acid, permaleic acid, perbenzoic acid, monoperphthalic acid or p-toluenepersulphonic acid.

The oxidation can also be carried out using hydrogen peroxide and catalytic amounts of an acid having a dissociation constant of at least $10^{-5}$, it being possible to employ low concentrations, for example 1-2% or less, but also larger amounts, of the acid. The activity of the mixture above all depends on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Acids suitable as catalysts are, for example, acetic acid, perchloric acid, and trifluoroacetic acid. Usually, at least molar amounts of the oxidising agent, and preferably a small excess of about 10% to about 20%, are used. The oxidation is carried out under mild conditions, for example at temperatures of about $-50°$ C. to about $+100°$ C., preferably of about $-10°$ C. to about $+40°$ C.

The oxidation of 2-cephem compounds to the 1-oxides of the corresponding 3-cephem compounds can also be carried out by treatment with ozone, as well as with organic hypohalite compounds, such as lower alkyl hypochlorites, for example tert.-butylhypochlorite, which are used in the presence of inert solvents, such as optionally halogenated hydrocarbons, for example methylene chloride, and at temperatures of about $-10°$ C. to about $+30°$ C., with periodate compounds, such as alkali metal periodates, for example potassium periodate, which are preferably used in an aqueous medium at a pH value of about 6 and at temperatures of about $-10°$ C. to about $+30°$ C., with iodobenzene dichloride, which is used in an aqueous medium, preferably in the presence of an organic base, for example pyridine, and with cooling, for example at temperatures of about $-20°$ C. to about $0°$, or with any other oxidising agent which is suitable for conversion of a thio group into a sulphoxide grouping.

In the 1-oxides of 3-cephem compounds of the formula IA, thus obtainable, especially in those compounds in which $R_1{}^a$, $R_1{}^b$ and $R_2$ have the abovementioned preferred meanings, the groups $R_1{}^a$, $R_1{}^b$ and/or $R_2$ can, within the defined framework, be converted into one another, split off or introduced. A mixture of isomeric α- and β-1-oxides can be separated, for example chromatographically.

The reduction of the 1-oxides of 3-cephem compounds of the formula IA can be carried out in a manner which is in itself known, by treatment with a reducing agent, if necessary in the presence of an activating agent. Possible reducing agents are: catalytically activated hydrogen, using noble metal catalysts which contain palladium, platinum or rhodium and which are optionally employed together with a suitable carrier, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediamine-tetraacetic acid or nitrilotriacetic acid; reducing dithionite, iodide or ferrocyanide anions which are used in the form of appropriate inorganic or organic salts, such as alkali metal salts, for example sodium dithionite or potassium dithionite, sodium iodide or potassium iodide, or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinous, phosphonous or phosphorous acids, as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethylene-iminium salts, especially chlorides or bromides, wherein the iminium group is substituted by a bivalent or two monovalent organic radicals, such as optionally substituted lower alkylene or lower alkyl groups, such as N-chloromethylene-N,N-diethyliminium chloride or N-chloromethylene-pyrrolidinium chloride; and the complex metal hydrides, such as sodium borohydride, in the presence of suitable activating agents, such as cobalt-II chloride, as well as borane dichloride.

As activating agents which are used together with those of the abovementioned reducing agents which do not themselves possess Lewis acid properties, that is to say which above all are employed together with the dithionite, iodide or ferrocyanide reducing agents and the trivalent phosphorus reducing agents which do not contain halogen, or in the catalytic reduction, there should especially be mentioned organic carboxylic acid halides and sulphonic acid halides, also sulphur halides, phosphorus halides or silicon halides having the same or a greater second order hydrolysis constant than benzoyl chloride, for example phosgene, oxalyl chloride, acetic acid chloride or acetic acid bromide, or chloroacetic acid chloride, pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethylchlorosilane or trichlorosilane and also suitable acid anhydrides such as trifluoroacetic acid anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting substances and the choice of the reducing agent, such as, for example, lower alkanecarboxylic acids or esters thereof, such as acetic acid and ethyl acetate, in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide, dimethylacetamide or hexamethylphosphoramide, ethers, for example diethyl ether, tetrahydrofurane or dioxane, ketones, for example acetone, or sulphones, especially aliphatic sulphones, for example dimethylsulphone or tetramethylenesulphone, and the like, together with the chemical reducing agents, these solvents preferably not containing any water. The reaction is usually carried out at temperatures of about −20° C. to about 100° C., it being possible to carry out the reaction at lower temperatures if very reactive activating agents are used.

In the 3-cephem compounds of the formula IA, thus obtainable, $R_1^a$, $R_1^b$ and/or $R_2$ can be converted into other groups $R_1^a$, $R_1^b$ or $R_2$ as described above.

Salts of compounds of the formulae IA and IB can be manufactured in a manner which is in itself known. Thus, salts of such compounds which possess acid groups can be formed, for example, by treatment with metal compounds, such as alkali metal salts, of suitable carboxylic acids, for example the sodium salt of α-ethylcaproic acid, or with ammonia or a suitable organic amine, preferably using stoichiometric amounts or only a small excess of the salt-forming agent. Acid addition salts of compounds of the formula IA and IB having basic groupings are obtained in the customary manner, for example by treatment with an acid or with a suitable anion exchange reagent. Inner salts of compounds of the formulae IA and IB which contain a salt-forming amino group and a free carboxyl group can be formed, for example, by neutralising salts, such as acid addition salts, to the isoelectric point, for example with weak bases, or by treatment with liquid ion exchangers. Salts of 1-oxides of compounds of the formula IA having salt-forming groups can be manufactured analogously.

Salts can be converted into the free compounds in the customary manner, metal salts and ammonium salts, for example, by treatment with suitable acids, and acid addition salts, for example, by treatment with a suitable basic agent.

Resulting mixtures of isomers can be separated into the individual isomers according to methods which are in themselves known, mixtures of diastereomeric isomers, for example, by fractional crystallisation, adsorption chromatography (column chromatography or thin layer chromatography) or other suitable separation processes. Resulting racemates can be separated into the antipodes in the usual manner, if appropriate after introducing suitable salt-forming groupings, for example by forming a mixture of diastereomeric salts with optically active salt-forming agents, separating the mixture into the diastereomeric salts and converting the separated salts into the free compounds, or by fractional crystallisation from optically active solvents.

The process also encompasses those embodiments according to which compounds arising as intermediate products are used as starting substances and the remaining process steps are carried out with these, or the process is stopped at any stage; furthermore, starting substances can be used in the form of derivatives or be formed during the reaction.

Preferably, those starting substances are used, and the reaction conditions are so chosen, that the compounds initially mentioned as being particularly preferred are obtained.

In the starting compounds of the formula II, the group Y which is removed is preferably a $-SO_2-R_5$ group, wherein $R_5$ has the indicated meaning, but especially the indicated preferred meaning.

The process according to the invention is distinguished, relative to previously known processes, by the fact that it starts from inexpensive, easily accessible starting materials, such as, in particular, the 1-oxides of the fermentatively preparable penicillins G or V and of 6-aminopenicillanic acid, of which the reactive groups can be protected in any known manner and can easily be liberated again after the reaction, and that the manufacture of the intermediate products required according to the invention takes place with high yields.

The starting materials of the formula II used according to the invention can be manufactured, for example, in accordance with the following reaction scheme:

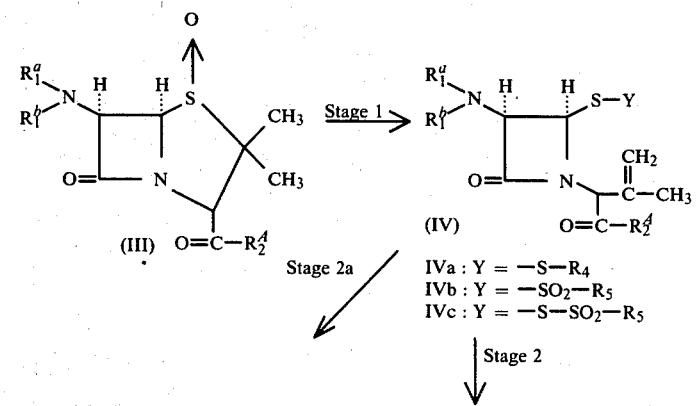

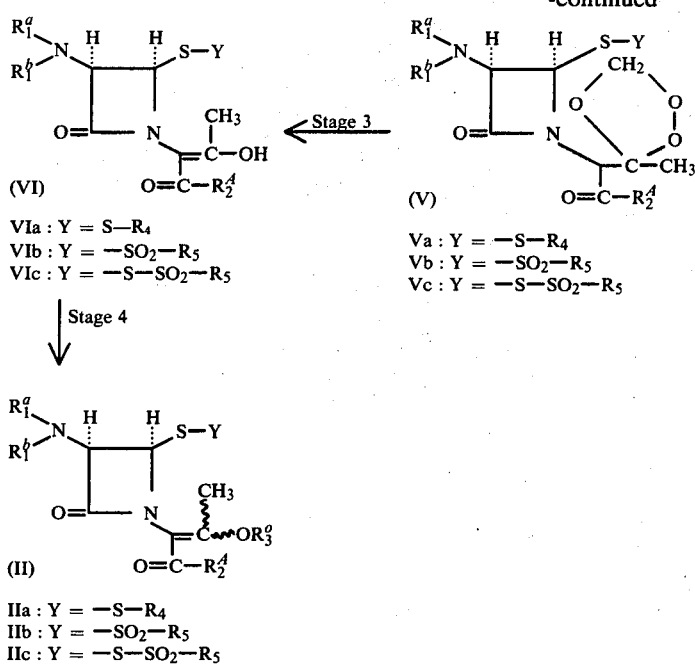

IIa : Y = —S—R$_4$
IIb : Y = —SO$_2$—R$_5$
IIc : Y = —S—SO$_2$—R$_5$

Starting compounds of the formula III are known or can be prepared according to known processes.

Compounds of the formula IVa are also known or can be prepared according to Netherlands Patent Specification No. 72/08,671.

The new compounds of the formulae IVb, IVc, Va, Vb, Vc, VIa, VIb, VIc, IIa, IIb and IIc, in which $R_1{}^a$, $R_1{}^b$, $R_2{}^A$ and Y have the meaning mentioned under formula II, and processes for their manufacture, are also a subject of the present invention.

Compounds of the formula IVb can be obtained from compounds of the formula III by reaction with a sulphinic acid of the formula HSO$_2$-R$_5$ or a sulphonyl cyanide of the formula N≡C—SO$_2$-R$_5$. Compounds of the formula IVc can be obtained from compounds of the formula III by reaction with a thiosulphonic acid of the formula H—S—SO$_2$-R$_5$. The reaction is carried out in an inert solvent or solvent mixture, for example an optionally halogenated, such as chlorinated, aliphatic, cycloaliphatic or aromatic hydrocarbon, such as pentane, hexane, cyclohexane, benzene, toluene, methylene chloride, chloroform or chlorobenzene, an aliphatic, cycloaliphatic or aromatic alcohol, such as a lower alkanol, for example methanol, ethanol, cyclohexanol or phenol, a polyhydroxy compounds, for example a polyhydroxyalkane, such as a dihydroxy-lower alkane, for example ethylene glycol or propylene glycol, a lower ketone, such as acetone or methyl ethyl ketone, an ether-like solvent, such as diethyl ether, dioxane or tetrahydrofurane, a lower carboxylic acid amide, such as dimethylformamide or dimethylacetamide, a lower dialkyl sulphoxide, such as dimethylsulphoxide and the like, or mixtures thereof.

The reaction is carried out at room temperature or preferably at elevated temperature, for example at the boiling point of the solvent employed, if desired in an inert gas atmosphere, such as a nitrogen atmosphere.

The reaction with the sulphonyl cyanide of the formula N≡C—SO$_2$-R$_5$ is accelerated by addition of compounds which provide halogen anions. Examples of suitable compounds which provide halogen anions are quaternary ammonium halides, especially chlorides and bromides, such as tetra-lower alkylammonium halides optionally substituted at the lower alkyl groups, for example by aryl, such as phenyl, such as tetraethylammonium chloride or bromide or benzyltriethylammonium chloride or bromide. The compounds which provide halogen anions are added in amounts of about 1 to about 50 mol percent, preferably of about 2 to about 5 mol percent.

Compounds of the formula IVb and IVc can also be obtained by reacting a compound of the formula IVa with a heavy metal sulphinate of the formula $M^{n+}(^-SO_2\text{-}R_5)_n$ or with a heavy metal thiosulphonate of the formula $M^{n+}(^-S\text{—}SO_2\text{-}R_5)_n$, wherein M represents a heavy metal cation and n denotes the valency of this cation. Suitable heavy metal sulphinates or heavy metal thiosulphonates are in particular those which have a higher solubility product in the reaction medium used than the heavey metal compounds of the formula $M^{n+}(\text{—S-R}_4)_n$ which are produced during the reaction. Suitable heavy metal cations $M^{n+}$ are in particular those which form particularly sparingly soluble sulphides. These include, for example, the monovalent or divalent cations of copper, mercury, silver and tin, copper$^{++}$ and silver$^+$ cations being preferred.

The heavy metal sulphinate or heavy metal thiosulphonate can either be employed as such or be formed in situ during the reaction, for example from a sulphinic acid of the formula HSO$_2$-R$_5$ or a thiosulphonic acid of the formula H—S—SO$_2$-R$_5$, or a soluble salt thereof, for example an alkali metal salt, such as a sodium salt, and a heavy metal salt of which the solubility product is higher than that of the heavy metal sulphinate or heavy metal thiosulphonate produced, for example a heavy metal nitrate, acetate or sulphate, for example silver nitrate, mercury-II diacetate or copper-II sulphate, or a soluble chloride, such as tin-II chloride dihydrate.

The reaction of a compound of the formula IVa with the heavy metal sulphinate of the formula $M^{n+}(^-SO_2\text{-}R_5)_n$ or the heavy metal thiiosulphonate of the formula $M^{n+}(^-S\text{—}SO_2\text{-}R_5)_n$ can be carried out in an inert organic solvent, in water or in a solvent mixture consisting of water and a water-miscible solvent. Suitable inert organic solvents are, for example, aliphatic, cycloaliphatic or aromatic hydrocarbons, such as pentane, hexane, cyclohexane, benzene, toluene or xylene, or aliphatic, cycloaliphatic or aromatic alcohols, such as lower alkanols, for example methanol, ethanol, cyclohexanol or phenol, polyhydroxy compounds, such as polyhydroxyalkanes, for example dihydroxy-lower alkanes, such as ethylene glycol or propylene glycol, carboxylic acid esters, for example lower carboxylic acid lower alkyl ester, such as ethyl acetate, lower ketones, such as acetone or methyl ethyl ketone, ether-like solvents, such as dioxane or tetrahydrofurane or polyethers, such as dimethoxyethane, lower carboxylic acid amides, such as dimethylformamide, lower alkyl nitriles, such as acetonitrile, or lower sulphoxides, such as dimethylsulphoxide. In water, or especially in mixtures of water and one of the solvents mentioned, including in emulsions, the reactions usually takes place substantially more rapidly than in the organic solvents alone.

The reaction temperature is usually about room temperature but can be lowered to slow down the reaction or raised, say up the boiling point of the solvent employed, to accelerate the reaction, it being possible to carry out the reaction under normal or elevated pressure.

In a resulting compound of the formula IV, a group $R_1{}^a$, $R_1{}^b$ or $R_2{}^A$ can be converted into another group $R_1{}^a$, $R_1{}^b$ or $R_2{}^A$, for which purpose it is possible to use analogous reactions to those indicated for the conversion of these groups in the case of compounds of the formula IA or IB.

In stage 2 and 3 or 2a, a compound of the formula IV can be converted into compound of the formula VI by oxidative degradation of the methylene group to an oxo group.

The oxidative splitting off of the methylene group in compounds of the formula IV to form an oxo group can be carried out by forming an ozonide compound of the formula V by treatment with ozone. Herein, ozone is usually employed in the presence of a solvent, such as an alcohol, for example a lower alkanol, such as methanol or ethanol, a ketone, for example a lower alkanone, such as acetone, an optionally halogenated aliphatic, cycloaliphatic or aromatic hydrocarbon, for example a halogeno-lower alkane, such as methylene chloride or carbon tetrachloride, or a solvent mixture, including an aqueous mixture, and with cooling or slight warming, for example at temperatures of about −90° C. to about +40° C.

An ozonide of the formula Va obtained as an intermediate product can, optionally without isolation, be converted into a compound of the formula Vb or Vc by reaction with a heavy metal sulphinate of the formula $M^{n+}(-SO-R_5)_n$ or a heavy metal thiosulphonate of the formula $M^{n+}(-S-SO_2-R_5)_n$, analogously to the conversion of compounds of the formula IVa to compounds of the formula IVb or IVc.

An ozonide of the formula V can be split by reduction in stage 3, to give a compound of the formula VI, for which it is possible to use catalytically activated hydrogen, for example hydrogen in the presence of a heavy metal hydrogenation catalyst, such as a nickel catalyst or a palladium catalyst, preferably on a suitable carrier, such as calcium carbonate or charcoal, or chemical reducing agents, such as reducing heavy metals, including heavy metal alloys or amalgams, for example zinc, in the presence of a hydrogen donor, such as an acid, for example acetic acid, or an alcohol, for example a lower alkanol, reducing inorganic salts, such as alkali metal iodides, for example sodium iodide, in the presence of a hydrogen donor, such as an acid, for example acetic acid, a reducing sulphide compound such as a di-lower alkylsulphide, for example dimethylsulphide, a reducing organic phosphorus compound, such as a phosphine, which can optionally contain substituted aliphatic or aromatic hydrocarbon radicals as substituents, such as tri-lower alkylphosphines, for example tri-n-butylphosphine, or triarylphosphines, for example triphenylphosphine, also phosphites which contain optionally substituted aliphatic hydrocarbon radicals as substituents, such as tri-lower alkylphosphites, usually in the form of corresponding alcohol adduct compounds, such as trimethyl-phosphite, or phosphorous acid triamides which contain optionally substituted aliphatic hydrocarbon radicals as substituents, such as hexa-lower alkylphosphorous acid triamides, for example hexamethyl-phosphorous acid triamide, the latter preferably in the form of a methanol adduct, or tetracyanoethylene. The splitting of the ozonide, which is usually not isolated, is normally carried out under the conditions which are employed for its manufacture, that is to say in the presence of a suitable solvent or solvent mixture, and with cooling or slight warming.

Enol compounds of the formula VI can also be present in the tautomeric keto form.

An enol compound of the formula VIa can be converted into a compound of the formula VIb or VIc by reaction with a heavy metal sulphinate of the formula $M^{n+}(-SO_2-R_5)_n$ or heavy metal thiosulphonate of the formula $M^{n+}(-S-SO_2-R_5)_n$, analogously to the conversion of compounds of the formula IVa to compounds of the formula IVb or IVc.

In a resulting compound of the formula VI, a group $R_1{}^a$, $R_1{}^b$ or $R_2{}^A$ can be converted into another group $R_1{}^a$, $R_1{}^b$ or $R_2{}^A$, for which analogous reactions can be used to those appropriate for the conversion of these groups in compounds of the formula IA or IB.

In the 4th stage, a resulting enol compound of the formula VI is converted into a compound of the formula II by etherification.

To manufacture lower alkyl enol ethers and optionally substituted α-phenyl-lower alkyl enol ethers of the formula II, the etherifying reagent used is, for example, a corresponding diazo compound, for example a diazo-lower alkane, such as diazomethane, diazoethane, diazo-n-butane or an optionally substituted α-phenyl-diazo-lower alkane, for example phenyldiazomethane or diphenyldiazomethane. These reagents are employed in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, a lower alkanol, for example methanol, ethanol or tert.-butanol, or an ether, such as a di-lower alkyl ether, for example diethyl ether, or a cyclic ether, for example tetrahydrofurane or dioxane, or a solvent mixture, and, depending on the diazo reagent, with cooling, at room temperature or with slight warming, and also, if necessary, in a closed vessel and/or under an inert gas atmosphere, for example a nitrogen atmosphere.

Furthermore it is possible to form lower alkyl enol ethers and optionally substituted α-phenyl-lower alkyl enol ethers of the formula II by treating an enol compound of the formula VI with a reactive ester of a corresponding alcohol of the formula $R_3^o$-OH. Suitable esters are above all those with strong inorganic or organic acids, such as mineral acids, for example hydrogen halide acids, such as hydrochloric acid, hydrobromic acid or hydriodic acid, and also sulphuric acid or halogenosulphuric acids, for example fluorosulphuric acid, or strong organic sulphonic acids, such as lower alkanesulphonic acids which are optionally substituted, for example by halogen, such as fluorine, or aromatic sulphonic acids, such as, for example, benzenesulphonic acids which are optionally substituted, for example by lower alkyl, such as methyl, halogen, such as bromine, and/or nitro, for example methanesulphonic acid, trifluoromethanesulphonic acid or p-toluenesulphonic acid. These reagents, especially dilower alkyl sulphates, such as dimethyl sulphate, as well as lower alkyl fluorosulphates, for example methyl fluorosulphate, or optionally halogen-substituted methanesulphonic acid lower alkyl esters, for example trifluoromethanesulphonic acid methyl ester, or corresponding α-phenyl-lower alkyl esters, for example benzyl esters and diphenylmethyl esters, such as benzyl halides or diphenylmethyl halides, such as chlorides or bromides, are usually employed in the presence of a solvent, such as an optionally halogenated, such as chlorinated, aliphatic, cycloaliphatic or aromatic hydrocarbon for example methylene chloride, an ether, such as dioxane or tetrahydrofurane, or a lower alkanol, such as methanol, or a solvent mixture. At the same time preferably suitable condensation agents are used, such as alkali metal carbonates or alkali metal bicarbonates, for example sodium carbonate or bicarbonate or potassium carbonate or bicarbonate (usually together with a sulphate), or organic bases such as, usually sterically hindered, tri-lower alkylamines, for example N,N-diisopropyl-N-ethylamine (preferably together with lower alkyl halogenosulphates, or optionally halogen-substituted methanesulphonic acid lower alkyl esters), the reaction being carried out with cooling, at room temperature or with warming, for example at temperatures of about $-20°$ C. to about 50° C., and, if necessary, in a closed vessel and/or in an inert gas atmosphere, for example a nitrogen atmosphere.

The etherification reaction can be accelerated substantially by phase transfer catalysis (see E. V. Dehmlow, Angewandte Chemie 5/1974, page 187). Phase transfer catalysts which can be used are quaternary phosphonium salts and especially quaternary ammonium salts, such as optionally substituted tetraalkylammonium halides, for example tetrabutylammonium chloride, bromide or iodide, or benzyltriethylammonium chloride, in catalytic amounts or in up to equimolar amounts. The organic phase used can be any water-immiscible solvent, for example one of the optionally halogenated, such as chlorinated, aliphatic, cycloaliphatic or aromatic hydrocarbons, such as trichloroethylene or tetrachloroethylene, dichloroethane, trichloroethane or tetrachloroethane, chlorobenzene and especially carbon tetrachloride, or also toluene or xylene. The alkali metal carbonates or alkali metal bicarbonates suitable for use as condensation agents, for example potassium carbonate or bicarbonate or sodium carbonate or bicarbonate, alkali metal phosphates, for example potassium phosphate, and alkali metal hydroxides, for example sodium hydroxide, can, in the case of compounds sensitive to bases, be added to the reaction mixture by titration so that the pH value remains approximately between 7 and 8.5 during the etherification.

Lower alkyl enol ethers of the formula II can also be prepared by treating an enol compound of the formula VI with a compound containing two or three hydroxyl groups etherified by lower alkyl, of the formula $R_3^o$-O, on the same carbon atom of aliphatic character, that is to say with a corresponding acetal or ortho-ester, in the presence of an acid agent. Thus, for example, it is possible to use, as etherifying agents, gem-lower alkoxy-lower alkanes, such as 2,2-dimethoxypropane, in the presence of a strong organic sulphonic acid, such as p-toluenesulphonic acid, and of a suitable solvent, such as a lower alkanol, for example methanol, or a di-lower alkylsulphoxide or lower alkylenesulphoxide, for example dimethylsulphoxide, or orthoformic acid tri-lower alkyl esters, for example orthoformic acid triethyl ester, in the presence of a strong mineral acid, for example sulphuric acid, or of a strong organic sulphonic acid, such as p-toluenesulphonic acid, and of a suitable solvent, such as a lower alkanol, for example ethanol, or an ether, for example dioxane, and compounds of the formula II, wherein $R_3^o$ represents lower alkyl, for example methyl or ethyl, can thus be obtained.

The lower alkyl enol ethers of the formula II can also be obtained when enol compounds of the formula VI are treated with tri-lower alkyl-oxonium salts of the formula $(R_3^o)_3O^\oplus A^\ominus$ (so-called Meerwein salts), or di-$R_3$O-carbenium salts of the formula $(R_3^oO)_2CH^\oplus A^\ominus$, or di-$R_3$-halonium salts of the formula $(R_3^o)_2Hal^\oplus A^\ominus$, wherein $A^\ominus$ denotes the anion of an acid and $Hal^\oplus$ denotes a halonium ion, especially a bromonium ion, and $R_3^o$ denotes lower alkyl. Such salts are, above all, tri-lower alkyl-oxonium salts, as well as di-lower alkoxy-carbenium salts or di-lower alkyl-halonium salts, especially the corresponding salts with complex acids containing fluorine, such as the corresponding tetrafluoborates, hexafluorophosphates, hexafluoroantimonates or hexachloroantimonates. Examples of such reagents are trimethyloxonium or triethyloxonium hexafluoantimonate, hexachloroantimonate, hexafluophosphate or tetrafluoborate, dimethoxycarbenium hexafluophosphate or dimethylbromonium hexafluoantimonate. These etherifying agents are preferably used in an inert solvent, such as an ether or a halogenated hydrocarbon, for example diethyl ether, tetrahydrofurane or methylene chloride, or in a mixture thereof, if necessary in the presence of a base, such as an organic base, for example a preferably sterically hindered tri-lower alkylamine, for example N,N-diisopropyl-N-ethyl-amine, and with cooling, at room temperature or with slight warming, for example at about $-20°$ C. to about 50° C., if necessary in a closed vessel and/or in an inert gas atmosphere, for example a nitrogen atmosphere.

Compounds of the formula II, wherein the hydroxy protective group $R_3^o$ is a 2-oxa-aliphatic or 2-oxa-cycloaliphatic or 2-thia-aliphatic or 2-thia-cycloaliphatic hydrocarbon radical are manufactured by acid-catalysed addition reaction, for example addition reaction catalysed by a strong mineral acid, such as sulphuric acid or hydrochloric acid, of α,β-unsaturated aliphatic or cycloaliphatic ethers or thioethers, such as 1-lower alkoxy-lower alkenes, for example 1-methoxyethene or 1-methoxypropene, 1-lower alkylthio-lower alkenes, such as 1-methylthio-ethene or 1-methylthio-propene, oxa- or thia-cyclo-lower alk-2-enes or -2,4-dienes having 5–7 ring atoms, for example 2,3-dihydrofurane, 2H-pyrane, 3,4-dihydro-2H-pyrane or corresponding analogous sulphur compounds, with the 3- hydroxy group of a compound of the formula VI. The addition reaction can be carried out in an excess of the unsaturated ether or thioether and optionally in an inert organic solvent, for example in an aliphatic, cycloaliphatic or aromatic hydrocarbon, such as pentane, hexane, cyclohexane, benzene, toluene and the like, with exclusion of water.

Silyl ethers of stannyl ethers embraced by the formula II, that is to say compounds of the formula II, wherein $R_3^o$ denotes a substituted silyl or stannyl group, are obtained in accordance with any process suitable for the silylation or stannylation of enol groups, for example by treatment with a suitable silylating agent, such as a dihalogeno-di-lower alkyl-silane, lower alkoxy-lower alkyl-dihalogeno-silane or tri-lower alkyl-silyl halide, for example dichloro-dimethylsilane, methoxy-methyl-dichloro-silane, trimethylsilyl chloride or dimethyl-tert.-butyl-silyl chloride, such silyl halide compounds preferably being used in the presence of a base, for example pyridine, with an optionally N-mono-lower alkylated, N,N-di-lower alkylated, N-tri-lower alkyl-silylated or N-lower alkyl-N-tri-lower alkyl-silylated N-(tri-lower alkyl-silyl)-amine (see, for example, British Pat. No. 1,073,530), for example with a hexa-lower alkyl-disilazane, such as hexamethyldisilazane, or with a silylated carboxylic acid amide, such as a bis-tri-lower alkyl-silyl-acetamide, for example bis-trimethylsilyl-acetamide, or trifluorosilylacetamide, or with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or a tri-lower alkyl-tin halide, for example tri-n-butyl-tin chloride (see, for example Netherlands Published Specification No. 67//11,107).

A compound of the formula IIa, wherein $R_3^o$ denotes lower alkyl or a protective radical for a hydroxyl group, can be converted into a compound of the formula IIb or IIc by reaction with a heavy metal sulphinate of the formula $M^{n+}(-SO_2-R_5)_n$ or a heavy metal thiosulphonate of the formula $M^{n+}(-S—SO_2-R_5)_n$, analogously to the conversion of compounds of the formula IVa to IVb or IVc.

In a resulting compound of the formula II, a group $R_1^a$, $R_1^b$, $R_2^A$ or $R_3$ can be converted into another group $R_1^a$, $R_1^b$, $R_2^A$ or $R_3$, for which purpose it is possible to use analogous reactions to those indicated for the conversion of these groups in the case of compounds of the formula IA or IV.

The pharmacologically usable compounds of the present invention can, for example, be used for the manufacture of pharmaceutical preparations which contain an effective amount of the active substance together with, or mixed with, inorganic or organic, solid or liquid, pharmaceutically usable excipients which are suitable for enteral administration or preferably for parenteral administration. Thus, tablets or gelatine capsules are used which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicaate, starches, such as corn starch, wheat starch, rice starch or arrowroot starch, gelatine, tragacanth, methylcellulose, sodium carboxymethylcellulose and/or polyvinyl-pyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Furthermore, the new pharmacologically active compounds can be used in the form of injectable preparations, for example preparations which can be administered intravenously, or of infusion solutions. Such solutions are, preferably, isotonic aqueous solutions or suspensions and these can, for example, be manufactured before use from lyophilised preparations which contain the active substance by itself or together with an excipient, for example mannitol. The pharmaceutical preparations can be sterilised and/or contain auxiliaries, for example preservatives, stabilisers, wetting agents and/or emulsifiers, solubilising agents, salts for regulating the osmotic pressure and/or buffers. The present pharmaceutical preparations which can, if desired, contain further pharmacologically valuable substances, are manufactured in a manner which is in itself known, for example by means of conventional mixing, granulating, dragee-making, dissolving or lyophilising processes, and contain from about 0.1% to 100%, especially from about 1% to about 50%, of lyophilised products or up to 100% of the active substance.

In the context of the present description, the organic radicals described as "lower" contain, unless expressly defined, up to 7, preferably up to 4, carbon atoms; acyl radicals contain up to 20, preferably up to 12, and above all up to 7, carbon atoms.

The examples which follow serve to illustrate the invention. The cephem compounds mentioned in the examples possess the R-configuration in the 6- and 7-position, and the azetidinone componds mentioned possess the R-configuration in the 3- and 4-position.

EXAMPLE 1

A solution of 60 μl (2 equivalents) of 1,5-diazabicyclo[5.4.0]undec-5-ene in 1 ml of tetrahydrofurane is added dropwise over the course of 5 minutes to a solution of 133 mg (0.2 mM) of an isomer mixture consisting of 2-[4-(p-toluenesulphonylthio)-3-phenoxyacetamido-2-oxoazetidin-1-yl]-3-methoxy-crotonic acid p-nitrobenzyl ester and the corresponding isocrotonic acid ester, in the ratio of about 4:1, in 4 ml of dry tetrahydrofurane. After standing at room temperature for 40 minutes, the mixture is diluted with 20 ml of benzene, cooled in an in icebath and stirred for 10 minutes with 10 ml of a 10% strength citric acid solution. The organic layer is separated off and washed successively with saturated sodium chloride solution, 10% strength sodium bicarbonate solution and sodium chloride solution. The solution is dried over magnesium sulphate and concentrated in vacuo, and the resulting yellow oil is purified by chromatography-filtration on 4 g of acid-washed silica gel (2 kg of silica gel are stirred three times with 2 l of concentrated hydrochloric acid in each case for 10 minutes, separated from the acid by decanting, washed with distilled water until neutral, rinsed with methanol and activated for 60 hours at 120° C.), with benzene/ethyl acetate, 5:1, as the eluting agent. The fractions containing the isomer mixture are combined and concentrated in vacuo. A semi-solid isomer mixture, consisting of 7β-phenoxyacetamido-3-methoxy-ceph-3-em-4-carboxylic acid p-nitrobenzyl ester and 7β-phenoxyacetamido-3-methoxy-ceph-2-em-4-carboxylic acid p-nitrobenzyl ester in the ratio of about 1:3 is obtained and can be separated into the two isomers on Woelm silica gel (activity III) with benzene/ethyl acetate, 5:1. The faster-running 7β-phenoxyacetamido-3-methoxy-ceph-2-em-4-carboxylic acid p-nitrobenzyl ester is recrystallised from methylene chloride/ether and has a melting point of 129°-131.5° C. The slower-running 7β-phenoxyacetamido-3-methoxy-ceph-3-em-4-carboxylic acid p-nitrobenzyl ester has a melting point of 140.5°-142° C. (from methylene chloride/ether).

The products can be further converted as follows:

A solution, prepared at 0° C., of 555 mg (1.11 mmols) of a crude mixture consisting of 7β-phenoxyacetamido-3-methoxy-ceph-2-em-4α-carboxylic acid p-nitrobenzyl ester and 7β-phenoxyacetamido-3-methoxy-ceph-3-em-4-carboxylic acid p-nitrobenzyl ester in the ratio of about 3:1, in 33 ml of tetrahydrofurane, is mixed, whilst stirring, with 16 ml of an 0.1N potassium hydroxide solution which has been precooled to 0° C. The mixture is stirrred for a further 5 minutes at 0° C., 100 ml of ice water and 100 ml of precooled methylene chloride are then added and the whole is stirred up briefly. Addition of 1 ml of saturated aqueous sodium chloride solution causes the two phases to separate. The organic phase is separated off, and the aqueous phase is again washed with 20 ml of methylene chloride, then covered with 50 ml of methylene chloride and acidified with 20 ml of 2 N hydrochloric acid. After shaking up, the organic phase is separated off and the hydrochloric acid solution is extracted twice more with 10 ml of methylene chloride at a time. The combined methylene chloride extracts are dried over sodium sulphate and evaporated in vacuo. The residue is recrystallised from methylene chloride/diethyl ether/pentane and gives 7β-phenoxyacetamido-3-methoxy-ceph-2-em-4α-carboxylic acid of melting point 142°-145° C.

The starting materials can be obtained as follows:

(a) A solution under 36.6 g (0.1 M) of 6-phenoxyacetamidopenicillanic acid 1β-oxide, 11.1 ml (0.11 M) of triethylamine and 23.8 g (0.11 M) of p-nitrobenzyl bromide in 200 ml of dimethylformamide is stirred for 4 hours uner nitrogen at room temperature. The reaction solution is then introduced into 1.5 l of ice water and the precipitate is filtered off, dried and twice recrystallised from ethyl acetate-methylene chloride. The colourless, crystalline 6-phenoxyacetamidopenicillanic acid p-nitrobenzyl ester 1β-oxide melts at 179°-180° C.

(b) A solution of 5.01 g (10 mM) of 6-phenoxyacetamidopenicillanic acid p-nitrobenzyl ester 1β-oxide and 1.67 g (10 mM) of 2-mercaptobenzthiazole in 110 ml of dry toluene is boiled for 4 hours under reflux in a nitrogen atmosphere. The solution is concentrated to approx. 25 ml by distilling off solvent and diluted with approx. 100 ml of ether. The product which has separated out is recrystallised from methylene chloride/ether and 2-[4-(benzthiazol-2-yldithio)-3-phenoxyacetamido-2-oxoazetidin-1-yl]-3-methylene-butyric acid p-nitrobenzyl ester of melting point 138°-141° C. is obtained.

(c) 1.06 g of finely powdered silver nitrate are added to a solution of 3.25 g (5.0 mM) of 2-[4-(benzthiazol-2-yldithio)-3-phenoxycetamido-2-oxaazetidin-1-yl]-3-methylenebutyric acid p-nitrobenzyl ester in 200 ml of acetone/water, 9:1 (v/v). Immediately afterwards, a solution of 890 mg (5 mM) of sodium p-toluenesulphinate in 100 ml of the same solvent mixture is introduced (over the course of 10 minutes). A light yellow precipitate forms immediately. After stirring for one hour at room temperature, the mixture is filtered, with addition of Celite. The filtrate is diluted with water and twice extracted with ether. The combined ether extracts are dried over sodium sulphate and after concentration give pale yellow solid 2-[4-(p-toluenesulphonylthio)-3-phenoxyacetamido-2-oxoazetidin-1-yl]-3-methylene-butyric acid p-nitrobenzyl ester. Thin layer chromatogram on silica gel (toluene/ethyl acetate, 2:1): Rf value = 0.24; IR spectrum (in $CH_2Cl_2$): characteristic bands at 3.90, 5.56, 5.70, 5.87, 6.23, 6.53, 6.66, 7.40, 7.50, 8.10, 8.72, 9.25 and 10.95 μ. The product can be employed without further purification in the subsequent reaction.

The same compound can also be obtained in accordance with the following methods:

(ci) 1.58 g (1.2 equivalents) of silver p-toluenesulphinate are added in portions for 10 minutes to a solution of 3.25 g (5.0 mM) of 2-[4-(benzthiazol-2-yldithio)-3-phenoxyacetamido-2-oxoazetidin-1-yl]-3-methylene-butyric acid p-nitrobenzyl ester in 200 ml of acetone/water, 9:1 (v/v). The suspension is stirred for one hour at room temperature, filtered and then further processed as described in Example 1c). 2-[4-(p-toluenesulphonylthio)-3-phenoxyacetamido-2-oxoazetidin-1-yl]-3-methylene-butyric acid p-nitrobenzyl ester is obtained in quantitative yield.

Silver p-tolenesulphinate is obtained as a colourless precipitate by combining aqueous solutions of equimolar amounts of silver nitrate and sodium p-toleuensulphinate. The product is dried in vacuo for 24 hours.

(cii) 2-[4-(p-Toluensulphonylthio)-3-phenoxyacetamido-2-oxoacetidin-1-yl]-3-methylene-butyric acid p-nitrobenzyl ester can also be obtained in quantitative yield, analogously to Example 1ci) from 3.25 g of 2-[4-(benzthiazol-2-yldithio)-3-phenoxyacetamido-2-oxoazetidin-1-yl]-3-methylene-butyric acid p-nitrobenzyl ester and 1.87 g (2equivalents) of copper-II di-p-toluenesulphinate.

Copper-II di-p-toluenesuphinate is obtained by reaction of copper sulphate and sodium p-toluenesulphinate (2 equivalents) in water. After filtering off, the salt is dried in vacuo for 12 hours at 60° C.

(ciii) 2-[4-(p-Toluensulphonylthio)-3-phenoxyacetamido-2-oxoazetidin-1-yl]-3-methylene-butyric acid p-nitrobenzyl ester can also be obtained analogously to Example 1ci) from 130 mg of 2-[4-(benzthizol-2-yldithio)-3-phenoxyacetamido-2-oxoazetidin-1-yl]-3-methylene-butyric acid p-nitrobenzyl ester and 85 mg (2 equivalents) of tin-II di-p-toluenesulphinate.

Tin-II di-p-toluenesulphinate is obtained by reaction of tin-II chloride ($2H_2O$) and sodium p-toleuensulphinate in water. After filtering off, and washing with water, the salt is dried in vacuo for about 12 hours at 50°-60° C.

(civ) 2-[4-(p-Toluenesulphonylthio)-3-phenoxyacetamido-2-oxoazetidin-1-yl]-3-methylene-butyric acid p-nitrobenzyl ester can also be obtained analogously to Example 1ci) from 130 mg of 2-[4-(benzthiazol-2-yldithio)-3-phenoxyacetamido-2-oxoazetidin-1-yl]-3-methylene-butyric acid p-nitrobenzyl ester and 102 mg (2 equivalents) of mercury-II di-p-toluenesulphinate.

Mercury-II di-p-toluenesulphinate is obtained by reaction of mercury-II diacetate and sodium p-toluenesulphinate in water. After filtering off, and washing with water, the salt is dried in vacuo for about 12 hours at 50°-60° C.

(cv) A solution of 517 mg (1.02 mM) of 6-phenoxyacetamidopenicillanic acid p-nitrobenzyl ester 1β-oxide and 187 mg (1.2 mM) of p-toluenesulphinic acid in 10 ml of 1,2-dimethoxyethane (or dioxane) is heated under reflux for 4.5 hours in the presence of 3.5 g of a molecular sieve 3A, and in a nitrogen atmosphere, after which a further 308 mg (1.98 mM) of p-toluenesulphinic acid, dissolved in 2 ml of 1,2-dimethoxyethane, are added in five portions at 45 minutes intervals. After 4.5 hours, the reaction mixture is poured into 100 ml of 5% strength aqueous sodium bicarbonate solution and extracted with ethyl acetate. The combined organic phases are washed with water and saturated aqueous sodium chloride solution, dried over magnesium sulphate and concentrated by evaporation. The residue is chromatographed on silica gel thick layer plates with toluene/ethyl acetate, 2:1, and gives 2-[4-(p-toluenesulphonylthio)-3-phenoxyacetamido-2-oxoazetidin-1-yl]-3-methylene-butyric acid p-nitrobenzyl ester.

(cvi) A mixture of 250 mg (0.5 mM) of 6-phenoxyacetamidopenicillanic acid p-nitrobenzyl ester 1β-oxide, 110 mg (0.61 mM) of p-toluenesulphonyl cyanide and 5 mg (0.022 mM) of benzyltriethylammonium chloride in 2 ml of dry, peroxide-free dioxane is stirred under argon at 110° C. for 4.5 hours. The solvent is evaporated off in vacuo and the yellow oil which remains is chromatographed on acid-washed silica gel. Elution with 30% ethyl acetate in toluene gives 2-[4-(p-toluenesulphonylthio)-3-phenoxyacetamido-2-oxoazetidin-1-yl]-3-methylene-butyric acid p-nitrobenzyl ester.

(cvii) A mixture of 110 mg (0.61 mM) of p-toluenesulphonyl cyanide and 4.5 mg (0.021 mM) of tetraethylammonium bromide in 1 ml of pure dioxane is stirred for 30 minutes at 110° C. under argon. A suspension of 250 mg (0.5 mM) of 6-phenoxyacetamidopenicillanic acid p-nitrobenzyl ester 1β-oxide in 1 ml of dioxane is then added and the resulting solution is stirred for 4 hours at 110° C. under argon. The solvent is removed in vacuo, the crude product is dissolved in ethyl acetate and the solution is washed with water and with saturated aqueous sodium chloride solution. The organic phase is dried with magnesium sulphate and freed from the solvent in vacuo, giving crude 2-[4-(p-toluenesulphonylthio)-3-phenoxyacetamido-2-oxoazetidin-1-yl]-3-methylene-butyric acid p-nitrobenzyl ester.

(d) 1.1 equivalents of ozone are passed into a solution of 1.92 g (3.0 mM) of 2-[4-(p-toluenesulphonylthio)-3-phenoxyacetamido-2-oxoazetidin-1-yl]-3-methylene-butyric acid p-nitrobenzyl ester in 30 ml of dry methyl acetate, at −78° C., over the course of 33 minutes. Immediately thereafter, excess ozone is removed by means of a stream of nitrogen (15 minutes at −78° C). 2.2 ml of dimethyl sulphide (10 equivalents) are added and the solution is warmed to room temperature. After standing for 5 hours, the solvent is distilled off in vacuo and the colourless oil which remains is taken up in 100 ml of benzene. The benzene solution is washed with three 50 ml portions of saturated sodium chloride solution, dried over magnesium sulphate and concentrated to dryness in vacuo. After recrystallising the residue from toluene, 2-[4-(p-toluenesulphonylthio)-3-phenoxyacetamido-2-oxoazetidin-1-yl]-3-hydroxy-crotonic acid p-nitrobenzyl ester of melting point 159°–160° C. is obtained.

(di) The crude 2-[4-(p-toluenesulphonylthio)-3-phenoxyacetamido-2-oxoazetidin-1-yl]-3-methylene-butyric acid p-nitrobenzyl ester obtained according to Example 1.cvii) is dissolved in 20 ml of methyl acetate and ozonised at −70° C. until starting material is no longer present, according to a thin layer chromatogram. A stream of nitrogen is then passed through the solution and the latter is warmed to 0°–5° C. A solution of 300 mg of sodium bisulphite in 5 ml of water is added and the mixture is stirred for about 5 minutes until no further ozonide is detectable by means of potassium iodide/starch paper. The mixture is diluted with ethyl acetate, the aqueous phase is separated off and the organic phase is washed with water, dried over magnesium sulphate and freed from the solvent in vacuo. The crude product is dissolved in 3 ml of methylene chloride and 15 ml of toluene are added. The precipitate is filtered off and the filtrate is concentrated by evaporation in vacuo. The residue is recrystallised from methanol and gives 2-[4-(p-toluenesulphonylthio)-3-phenoxyacetamido-2-oxoazetidin-1-yl]-3-hydroxy-crotonic acid p-nitrobenzyl ester of melting point 159°–160° C. 155°–

(e) A solution of 1.93 g of 2-[4-(p-toluenesulphonylthio)-3-phenoxyacetamido-2-oxoazetidin-1-yl]-3-oxo-butyric acid p-nitrobenzyl ester (3.0 mM) in 15 ml of dry chloroform is cooled to 0° C. and 6 ml of a solution of diazomethane in ether (0.75 molar, corresponding to 1.5 equivalents) is added over the course of 10 minutes. The mixture is stirred for two hours at 0° C., excess diazomethane is removed by means of a stream of nitrogen and the solvent is stripped off in vacuo. The crude product is purified by filtration through Woelm silica gel (activity III, 40-fold amount), using benzene/-ethyl acetate, 5:1. The colourless oil obtained after distilling off the solvent crystallises on standing. After recrystallisation from methylene chloride/ether, an isomer mixture consisting of 2-[4-(p-toluenesulphonylthio)-3-phenoxyacetamido-2-oxoazetidin-1-yl]-3-methoxy-crotonic acid p-nitrobenzyl ester and the corresponding isocrotonic acid ester in the ratio of about 4:1 is obtained. Melting point of the mixture: 155–156.5° C.

EXAMPLE 2

A solution of 279 mg of 2-[4-(p-toluenesulphonylthio)-3-phenoxyacetamido-2-oxoazetidin-1-yl]-3-hydroxy-crotonic acid diphenylmethyl ester (0.428 mmol) in 4 ml of chloroform and 1 ml of hexamethyldisilazane is heated for one hour under reflux and evaporated in vacuo, and the oily residue is dried for one hour under a high vacuum. The silylated crude product consists of 2-[4-(p-toluenesulphonylthio)-3-phenoxyacetamido-2-oxoazetidin-1-yl]-3-trimethylsilyloxy-crotonic acid diphenylmethyl ester and the corresponding isocrotonic acid diphenylmethyl ester.

The resulting crude product is taken up in 3 ml of dry chloroform, the solution is cooled to 0° C. and 0.069 ml (0.47 mmol) of 1,5-diazbicyclo[5.4.0]undec-5-ene is added under nitrogen, whilst stirring. After a reaction time of 1 hour, the solution is mixed with 0.3 ml of acetic acid and dilutec with chloroform. The chloroform solution is washed with dilute sulphuric acid, water and dilute sodium bicarbonate solution. The aqueous phases are extracted with chloroform and the combined organic phases are dried over sodium sulphate and concentrated in vacuo. Crude 7β-phenoxyacetamido-3-hydroxy-ceph-3-em-4-carboxylic acid diphenylmethyl ester is obtained. Rf value: 0.13 (silica gel; toluene/ethyl acetate, 3:1).

· The resulting crude product is taken up in methanol and an excess of diazomethane solution in ether is added at 0° C. After a reaction time of 5 minutes, the solution is concentrated completely and the oily residue is chromatographed on silica gel thick layer plates (toluene-/ethyl acetate, 3:1). The silica gel of the zone at Rf=0.19 is extracted with ethyl acetate and gives 7β- phenoxyacetamido-3-methoxy-ceph-3-em-4-carboxylic acid diphenylmethyl ester; melting point 120° C. (from ether). IR spectrum (in CHCl$_3$):3,310, 1,775, 1,700, 1,690 and 1,600 cm$^{-1}$.

The starting material is prepared as follows:

(a) 100 g (27.3 mM) of 6-phenoxyacetamido-penicillanic acid 1β-oxide, 500 ml of dioxane and 58.4 g (30 mM) of diphenylmethyldiazomethane after about 2 hours give 6-phenoxyacetamidopenicillanic acid diphenylmethyl ester 1β-oxide; melting point 144°–146° C. (ethyl acetate/petroleum ether).

(b) Analogously to Example 1b), 292 g (55 mM) of 6-phenoxyacetamido-penicillanic acid diphenylmethyl ester 1β-oxide and 99 g (59.5 mM) of 2-mercaptobenzthiazole give 2-[4(benzthiazol-2-yldithio)-3-phenoxyacetamido-2-oxoazetidin-1-yl]-3-methylene-butyric acid diphenylmethyl ester; melting point 140°–141° C. (from toluene/ether).

(c) Analogously to Example 1c), 10 g (14.7 mM) of 2-[4-(benzthiazol-2-yldithio)-3-phenoxyacetamido-2-oxoazetidin-1-yl]-3-methylene-butyric acid diphenylmethyl ester in 50 ml of ethyl acetate and 4.92 g (24.98 mM) of finely powdered silver p-toluenesulphinate on stirring for 7 hours at room temperature give 2-[4-(p-toluenesulphonylthio)-3-phenoxyacetamido-2-oxoazetidin-1-yl]-3-methylene-butyric acid diphenylmethyl ester. Rf value=0.28 (silica gel, toluene/ethyl acetate, 3:1); IR spectrum (CHCl$_3$):1,782, 1,740, 1,695, 1,340 and 1,150 cm$^{-1}$.

2-[4-(p-Toluenesulphonylthio)-3-phenoxyacetamdio-2-oxozetidin-1-yl]-3-methylene-butyric acid diphenylmethyl ester can also be prepared as follows:

(ci) A suspension of 106.5 g of 6-phenoxyacetamidopenicillanic acid diphenylmethyl ester 1β-oxide and 33.8 g of 2-mercaptobenzthiazole in 900 ml of toluene and 9 ml of glacial acetic acid is boiled for 2 hours under nitrogen using a water separator, during which time about 4.5 ml of water are separated off. The solution is cooled to room temperature, a total of 85.5 g of silver p-toluenesulphinate is added in portions over the course of 1 hour and the mixture is then stirred for a further 2 hours at 22° C. The mixture is filtered through Hyflo and the filtrate is washed twice with saturated aqueous sodium chloride solution. The organic phase is dried over magnesium sulphate, concentrated in vacuo to about 1 liter, decolorised with 30 g of Norit and concentrated by evaporation. The resulting yellow foam is crystallised from methylene chloride/diethyl ether. Melting point 79°–82° C. Rf value=0.55 (silica gel; toluene/ethyl acetate, 3:1). Further quantities of the substance can be obtained from the mother liquors by crystallisation from methylene chloride/-diethyl ether.

(d) Analogously to Example 1d), 10.8 g (16.2 mM) of 2-[4-(p-toluenesulphonylthio)-3-phenoxyacetamido-2-oxoaxetidin-1-yl]-3-methylene-butyric acid diphenylmethyl ester in 1 l of methylene chloride and 1.1 equivalents of ozone give 2-[4-(p-toluenesulphonylthio)-3-phenoxyacetamido-2-oxoazetidin-1-yl]-3-hydroxy-crotonic acid diphenylmethyl ester; melting point 142°–143° C. (from ether/pentane).

The ozonisation can also be carried out at 0° C:

15.2 mmols of ozone are passed into a solution of 9.23 g (13.8 mmols) of 2-[4-(p-toluenesulphonylthio)-3-phenoxyacetamido-2-oxoazetidin-1-yl]-3-methylene-butyric acid diphenylmethyl ester in 960 ml of methylene chloride at 0° C. over the course of 19 minutes. 10 ml of dimethylsulphide are added to the clear reaction solution and the mixture is stirred for 20 minutes at 5° C. After concentrating under a waterpump vacuum, and drying the residue in a high vacuum, a light yellow foam results, which crystallises from methylene chloride/hexane; the melting point of the resulting 2-[4-(p-toluenesulphonylthio)-3-phenoxyacetamido-2-oxoazetidin-1-yl]-3-hydroxy-crotonic acid diphenymethyl ester is about 134°–138° C. Thin layer chromatogram: Rf value ~ 0.46 (silica gel; toluene/ethyl acetate, 3:1).

The same compound can also be obtained in accordance with the following methods:

(di) A solution of 684 mg (1 mM) of 2-[4-(benzthiazol-2-yldithio)-3-phenoxyacetamido-2-oxoazetidin-1-yl]-3-hydroxycrotonic acid diphenylmethyl ester in 20 ml of acetone/water, 9:1 (v/v) is stirred with 341 mg (1.3 mM) of silver p-toluenesulphinate for 60 minutes at room temperature. The yellow reaction mixture is mixed with 50 ml of acetone and filtered. The filtrate is concentrated by evaporated in vacuo and the residue is chromatographed on 30 g of acid-washed silica gel using toluene/ethyl acetate, 4:1. The resulting 2-[4-(p-toluenesulphonylthio)-3-phenoxyacetamido-2-oxoazetidin-1-yl]-3-hydroxy-crotonic acid diphenylmethyl ester is recrystallised from ether/pentane and melts at 142°–143° C.

(dii) A solution of 72.9 mg (0.1 mM) of the crude ozonide, obtained by ozonisation of 68.1 mg (0.1 mM) of 2-[4-benzthiazol-2-ylthio)-3-phenoxyacetamido-2-oxoazetidin-1-yl]-3-thiazol-2-ylthio)-3-phenoxyacetamido-2-oxoazetidin-1-yl]-3-methylene-butyric acid diphenylmethyl ester in ethyl acetate and evaporation of the solvent, in 2 ml of acetone/water, 9:1 (v/v) is stirred with 35 mg (1.3 equivalents) of silver p-toluenesulphinate for one hour at room temperature. The reaction mixture is diluted with 3 ml of acetone and filtered. 0.2 ml of dimethylsulphide is added to the filtrate and the mixture is stirred for two hours at room temperature (until it gives a negative iodine-starch reaction) After removing the solvent in vacuo, the residue is chromatographed on 3 g of acid-washed silica gel, using toluene/ethyl acetate, 4:1. The resulting 2-[4-(p-toluenesulphonylthio)-3-phenoxyacetamido-2-oxoazetidin-1-yl]-3-hydroxy-crotonic acid diphenylmethyl ester is recrystallised from ether/pentane and melts at 142°–143° C. After a further recrystallisation, from methylene chloride/diethyl ether, a melting point of 144°–145° C. (corrected) is obtained; $[\alpha]_D^{20} = -68°\pm1°$ (c=1; chloroform); thin layer chromatogram: Rf value=0.81 (silica gel; methylene chloride/ethyl acetate, 8:2) UV spectrum (ethyl alcohol): $\lambda_{max}$=261 nm (ε=14,400); IR spectrum (Nujol): characteristic bands at 3.00; 5.56; 5.93; 5.98; 6.06; 6.19; 6.25; 6.54; 6.70; 6.82; 7.02; 7.47; 8.03; 8.76; 9.53; 10.23; 10.60; 12.30; 13.26 and 14.30 μ.

EXAMPLE 3

0.12 ml of bis-trimethylsilyl-acetamdide (0.508 mmol) is added to a solution of 301 mg (0.462 mmol) of 2-[4-(p-toluenesulphonylthio)-3-phenoxyacetamido-2-oxoazetidin-1-yl]-3-hydroxy-crotonic acid diphenylmethyl ester in 3 ml of 1,2-dimethoxyethane under a nitrogen atmosphere, and the mixture is stirred for one hour at room temperature. The solution is completely concentrated by evaporation and the oily residue is dried for one hour under a high vacuum. The silylated crude product is taken up in 3 ml of dried 1,2-dimethoxyethane and after cooling to 0° C. 0.075 ml (0.508 mmol) of 1,5-diazabicyclo [5.4.0]undec-5-ene is added. After 6 hours' reaction time at 0° C. under a nitrogen atmosphere, 0.3 ml of acetic acid is added and the mixture is diluted with methylene chloride. The methylene chloride solution is washed successively with dilute sulphuric acid, water and dilute bicarbonate solution. The aqueous phases are extracted with methylene chloride and the combined organic phases are dried with sodium sulphate, concentrated in vacuo and dried under a high vacuum. Crude 7β-phenoxyacetamido-3-hydroxy-ceph-3-em-4-carboxylic acid diphenylmethyl ester is obtained. An excess of a solution of diazomethane in ether is added to the solution of the crude product is chloroform at 0° C. and the mixture is left to stand for 5 minutes at 0° C. It is then concentrated completely and the residue is chromatographed on silica gel, as in Example 2. 7β-Phenoxyacetamido-3-methoxy-ceph-3-em-4-carboxylic acid diphenylmethyl ester; Rf value=0.19 (silica gel; toluene/ethyl acetate, 3:1); melting point 120° C. (from ether), IR spectrum (in $CHCl_3$):3,310, 1,775, 1,710, 1,690 and 1,600 $cm^{-1}$, is obtained.

EXAMPLE 4

0.045 ml (0.3 mmol) of 1,5-diazabicyclo[5.4.0]undec-5-ene is added to a solution of 100 m (0.15 mmol) of an isomer mixture consisting of 2-[4-(p-toluenesulphonylthio)-3-phenoxyacetamido-2-oxoazetidin-1-yl]-3-methoxy-crotonic acid diphenylmethyl ester and the corresponding isocrotonic acid ester in 4 ml of dry 1,2-dimethoxyethane whilst stirring in a nitrogen atmosphere. The solution is stirred for 40 minutes at room temperature under nitrogen and then cooled with ice, and 0.1 ml of acetic acid is added. The solution, diluted with methylene chloride, is successively washed with dilute sulphuric acid, water and dilute bicarbonate solution. The aqueous phases are extracted with methylene chloride. The combined organic phases are dried with sodium sulphate, concentrated and completely freed from the solvent under a high vacuum. The oily residue is chromatographed on a silica gel thick layer plate (running agent toluene/ethyl acetate, 3:1, developed once). The two zones at Rf=0.19 and 0.4 respectively are jointly extracted with ethyl acetate and the resulting solution is concentrated completely. An oily product is obtained, which consists of 7β-phenoxyacetamido-3-methoxy-ceph-3-em-4-carboxylic acid diphenylmethyl ester and the isomer 7β-phenoxyacetamido-3-methoxy-ceph-2-em-4-carboxylic acid diphenylmethyl ester in the ratio of 1:4. Rf value=0.14 and 0.32 respectively (silica gel, toluene/ethyl acetate, 3:1); IR spectrum (in $CHCl_3$):3,400, 3,310, 1,785, 1,770, 1,750, 1,710, 1,690, 1,630 and 1,600 $cm^{-1}$.

(i) The ratio of resulting ceph-2-em to ceph-3-em derivative depends, inter alia, on the solvent used for the cyclisation, on the concentration of the starting material and of the 1,5-diazabicyclo[5.4.0]undec-5-ene and also on the reaction time. The table which follows lists some reactions which were carried out analogously to the above example, in each case with 100 mg of an isomer mixture consisting of about 95% of 2-[4-(p-toluenesulphonylthio)-3-phenoxyacetamido-2-oxoazetidin-1-yl]-3-methoxy-isocrotonic acid diphenylmethyl ester and about 5% of the corresponding crotonic acid derivative. The reaction time was 20 minutes in each case and the working up was carried out analogously to the preceding example.

| Solvent | Concentration of starting material weight/volume | Equivalents of 1,5-diazabicyclo-[5.4.0]undec-5-ene | Ratio of resulting ceph-2-em to ceph-3-em derivative |
| --- | --- | --- | --- |
| Acetone | 10% | 1.5 | ~ 3 : 2 |
| Toluene | 10% | 1.5 | ~ 1 : 1 |
| Ethyl acetate | 10% | 1.5 | ~ 4 : 3 |
| Ethyl acetate | 20% | 1.3 | ~ 4 : 3 |
| Isobutyl methyl ketone | 20% | 1.3 | ~ 9 : 10 |
| Methylchloroform | 20% | 1.3 | ~ 9 : 7 |
| 1,2-Dimethoxyethane | 20% | 1.3 | ~ 6 : 5 |

(a) The isomer mixture employed as the starting material can be obtained analogously to Example 1(e) from 4 g (6.14 mM) of 2-[4-(p-toluenesulphonylthio)-3-phenoxyacetamido-2-oxoazetidin-1-yl]-3-hydroxy-crotonic acid diphenylmethyl ester and an excess of diazomethane solution in ether. The resulting isomer mixture consisting of 2-[4-(p-toluenesulphonylthio)-3-phenoxyacetamido-2-oxoazetidin-1-yl]-3-methoxy-crotonic acid diphenylmethyl ester and the corresponding isocrotonic acid diphenylmethyl ester (about 3:1) crystallises from ethyl acetate/pentane and has a melting point of 150°-152° C.

The isomer mixture employed as the starting material, or the crotonic acid and isocrotonic acid derivative, can also be obtained as follows:

(ai) A solution of 698 mg (1 mM) of an isomer mixture consisting of 2-[4-(benzthiazol-2-ylthio)-3-phenoxyacetamido-2-oxoazetidin-1-yl]-3-methoxy-crotonic acid diphenylmethyl ester and the corresponding isocrotonic acid diphenylmethyl ester in 20 ml of acetone/water, 9:1 (v/v) is stirred with 341 mg (1.3 mM) of silver p-toluenesulphinate for 1 hour at room temperature. The yellow reaction mixture is diluted with 50 ml of acetone and filtered. The filtrate is concentrated by evaporation in vacuo and the residue is chromatographed on 30 g of acid-washed silica gel using toluene/ethyl acetate, 2:1. An isomer mixture consisting of 2-[4-(p-toluenesulphonylthio)-3-phenoxyacetamido-2-oxoazetidin-1-yl]-3-methoxy-crotonic acid diphenylmethyl ester and 2-[4-(p-toluenesulphonylthio)-3-phenoxyacetamido-2-oxoazetidin-1-yl]-3-methoxy-isocrotonic acid diphenylmethyl ester is obtained.

(aii) The reaction described under ai) can also be carried out in tetrahydrofurane instead of in acetone/water, in which case the mixture must be stirred for about 24 hours at room temperature.

(aiii) 0.21 ml (1.2 mM) of ethyl-diisopropylamine and 0.12 ml (1.5 mM) of fluorosulphonic acid methyl ester are added to a solution of 336 mg (0.5 mM) of 2-[4-(p-toluenesulphonylthio)-3-phenoxyacetamido-2-oxoazetidin-1-yl]-3-hydroxy-crotonic acid diphenylmethyl ester in 4 ml of ethylene chloride at 0° C. and the mixture is stirred for 30 minutes at 0° C. and a further 30 minutes at room temperature. The reaction mixture is diluted with ethyl acetate, washed with saturated aqueous sodium chloride solution and dilute aqueous sodium bicarbonate solution and dried over sodium sulphate. The residue which remains after concentrating by evaporation is chromatographed on silica gel. With toluene- /ethyl acetate, 4:1, a little starting material is first eluted. Thereafter, an isomer mixture consisting of 2-[4-(p-toluenesulphonylthio)-3-phenoxyacetamido-2-oxoazetidin-1-yl]-3-methoxy-crotonic acid diphenylmethyl ester and the corresponding isocrotonic acid diphenylmethyl ester is isolated with toluene/ethyl acetate, 1:1. (aiv) 76 mg (0.55 mM) of potassium carbonate and 0.088 ml (0.92 mM) of dimethyl sulphate are added to a solution of 300 mg (0.447 mM) of 2-[4-(p-toluenesulphonylthio)-3-phenoxyacetamido-2-oxoazetidin-1-yl]-3-hydroxy-crotonic acid diphenylmethyl ester in 4 ml of acetone and the mixture is stirred for 5 hours at room temperature. The solution is then diluted with ethyl acetate, washed with water and dried over sodium sulphate. After removing the solvent, the residue is recrystallised from ethyl acetate/pentane, giving an isomer mixture consisting of 2-[4-(p-toluenesulphonylthio)-3-phenoxyacetamido-2-oxoazetidin-1-yl]-3-methoxy-crotonic acid diphenylmethyl ester and the corresponding isocrotonic acid diphenylmethyl ester.

(av) 1.57 g of N,N'-dinitroso-N,N'-dimethyloxamide are added to a solution of 6.73 g of 2-[4-(p-toluenesulphonxylthio)-3-phenoxyacetamido-2-oxoazetidin-1-yl]-3-hydroxy-crotonic acid diphenylmethyl ester (crystalline) in 67 ml of absolute tetrahydrofurane at $-20°$ C., and thereafter a solution of 0.57 ml (0.51 g) of ethylenediamine in 5 ml of tetrahydrofurane is added over the course of 15 minutes. After the addition, the mixture is stirred for 1 hour at 0° C., 0.53 ml (11 mmols) of glacial acetic acid and 6.7 g of Celite are added and the whole is filtered. The residue is washed with 5 times 20 ml of tetrahydrofurane. The filtrate and the wash liquids are combined, concentrated to approx. 20 g and mixed with 20 ml of hexane. The crystals are filtered of, washed with tetrahydrofurane/hexane, 1:2, and dried under a high vacuum.

The crystals consist in the main of 2-[4-(p-toluenesulphonylthio)-3-phenoxyacetamido-3-oxoazetidin-1-yl]-3-methoxy-isocrotonic acid diphenylmethyl ester. A sample is recrystallised from ethyl acetate/diethyl ether and gives the following analytical data: melting point 167°–169° C.; $[\alpha]_D^{20} = -30° \pm 1°$ 1; methylene chloride); thin layer chromatogram: Rf value=0.57 (silica gel; methylene chloride/ethyl acetate/glacial acetic acid, 60:40:1); UV spectrum (ethyl alcohol): $\lambda_{max}=260$ mμ ($\epsilon=16,600$); IR spectrum (Nujol): characteristic bands at 2.97; 5.62; 5.90; 6.27; 6.61; 6.66; 7.17; 7.53; 7.70; 7.96; 8.02; 8.20; 8.80; 9.20; 10.26; 12.24 and 13.30 μ. NMR spectrum (100 megacycles/second, in CDCl$_3$): δ2.32(s/CH$_3$); 2.34(s/CH$_3$); 3.73 (s/OCH$_3$); 4.30/4.44 (AB; J=5/azetidine-4-CH-); 6.8–7.5 (m/19 aromatic H, NH) ppm.

Apart from a little isocrotonic acid derivative, the mother liquor in the main contains 2-[4-(p-toluenesulphonylthio)-3-phenoxyacetamido-2-oxoazetidin-1-yl]-3-methoxy-crotonic acid diphenylmethyl ester, which after chromatographic purification on silica gel has a melting point of 146°–148° C. (corrected, from ethyl acetate/hexane); NMR spectrum (100 megacycles/second, in CDCl$_3$): δ2.08 (s/vinyl—CH$_3$); 2.26 (s/aromatic—CH$_3$); 3.70 (s/—OCH$_3$); 4.47 (s/—OCH$_2$CO—); 4.94 (dd/J=5 and 8/azetidine-3—CH—); 5.83 (d/J=5/azetidine-4-CH-), 6.8—7.5 (m/19 aromatic H, —NH—) ppm; $[\alpha]_D^{20}=+21°\pm 1°$; (c=1, methylene chloride).

(avi) 3.78 g (30 mmols) of dimethylsulphate and 30 ml of 20 percent strength aqueous potassium bicarbonate solution are added to a suspension of 6.72 g (10 mmols) of 2-[4-(p-toluenesulphonylthio)-3-phenoxyacetamido-2-oxoazetidin-1-yl]-3-hydroxy-crotonic acid diphenylmethyl ester (crystalline) and 0.36 g (1 mmol) of tetra-n-butylammonium iodide in 100 ml of toluene and the mixture is stirred vigorously for 4 hours at room temperature. During the first 15 minutes, the solid dissolves. The mixture is diluted with toluene and washed with saturated aqueous sodium chloride solution. After drying the organic phase with sodium sulphate, and concentrating it, crystallisation from ethyl acetate/diethyl ether gives 2-[4-(p-toluenesulphonylthio)-3-phenoxyacetamido-2-oxoazetidin-1-yl]-3-methoxy-isocrotonic acid diphenylmethyl ester.

(avii) 1.08 g (3 mmols) of tetrabutylammonium iodide and 1.9 ml (2.52 g, 20 mmols) of dimethylsulphate are added to a suspension of 3.36 g (5 mmols) of 2-[4-(p-toluenesulphonylthio)-3-phenoxyacetamido-2-oxoazetidin-1-yl]-3-hydroxy-crotonic acid diphenylmethyl ester (crystalline) in 15 ml of carbon tetrachloride and 10 ml of water. The mixture is vigorously stirred at room temperature and 1 N sodium hydroxide solution is added to it by means of an automatic titrator in sufficient amount to keep the pH constant at 7.0. In the course of 4–5 hours, 1.5–2 equivalents of sodium hydroxide solution are consumed. The mixture is diluted with ethyl acetate and water and a little sodium chloride is added. The organic phase is dried over sodium sulphate and concentrated by evaporation. The residue is crystallised from a little ethyl acetate/hexane, 1:1, and gives 2-[4-(p-toluenesulphonylthio)-3-phenoxyacetamido-2-oxoazetidin-1-yl]-3-methoxy-iso-crotonic acid diphenylmethyl ester.

The isomer mixture employed as the starting material can also be obtained via the corresponding 2-benzoxazole derivatives as follows:

(aviii) A solution of 10 g of 6-phenoxyacetamidopenicillanic acid diphenylmethyl ester 1β-oxide and 3 g of 2-mercaptobenzoxazole in 25 ml of dry tetrahydrofurane is completely concentrated by evaporation in vacuo. The foam which remains is heated to 120° C. (oil bath temperature) for 70 minutes, under a waterpump vacuum. The fused residue is cooled and then chromatographed on 500 g of acid-washed silica gel, using toluene/ethyl acetate, 6:1 followed by 3:1. 2-[4-(Benzoxazol-2-yldithio)-3-phenoxyacetamido-2-oxoazetidin-1-yl]-3-methylenebutyric acid diphenylmethyl ester is obtained in the form of a white foam; IR spectrum (methylene chloride): characteristic bands at 5.6, 5.75, 5.90 and 6.7 μ.

(aix) Approximately one equivalent of ozone (in the form of an O$_2$/O$_3$ mixture) is passed into a solution, cooled to $-70°$ C., of 3.35 g of 2-[4-(benzoxazol-2-yldithio)-3-phenoxyacetamido-2-oxoazetidin-1-yl]-3-methylene-butyric acid diphenylmethyl ester in 125 ml of ethyl acetate, until starting material is no longer detectable by thin layer chromatography (silica gel; toluene/ethyl acetate, 3:1). The solution is concentrated by evaporation to about 50 ml in vacuo, mixed with 5 ml of dimethyl sulphide and stirred until the potassium iodide/starch test no longer gives a reaction. The mixture is concentrated by evaporation in vacuo, the residue is dissolved in 150 ml of benzene and the solution is washed with water. The organic phase is dried over sodium sulphate and concentrated by evaporation. The residue is chromatographed on 150 g of acid-washed silica gel, using toluene/ethyl acetate, 4:1. 2-[4-(Benzoxazol-2-yldithio)-3-phenoxyacetamido-2-oxoazetidin-1-yl]-3-hydroxy-crotonic acid diphenylmethyl ester is obtained in the form of a white foam; IR spectrum (methylene chloride): characteristic bands at 5.60, 5.90 and 6.0 μ.

(ax) A solution of diazomethane in ether is added dropwise to a solution of 1.7 g of 2-[4-(benzoxazol-2-yldithio)-3-phenoxyacetamido-2-oxoazetidin-1-yl]-3-hydroxy-crotonic acid diphenylmethyl ester in 12.5 ml of methylene chloride at 0° C., whilst stirring, until starting material is no longer detectable by thin layer chromatography (silica gel; toluene/ethyl acetate, 3:2). The mixture is concentrated by evaporation in vacuo and the residue is chromatographed on 80 g of acid-washed silica gel, using toluene/ethyl acetate, 2:1. An isomer mixture consisting of 2-[4-(benzoxazol-2-yldithio)-3-phenoxyacetamido-2-oxoazetidin-1-yl]-3-methoxy-crotonic acid diphenylmethyl ester and the corresponding isocrotonic acid diphenylmethyl ester in the ratio of about 5:1 is obtained; IR spectrum (methylene chloride): characteristic bands at 5.60, 5.85 sh, 5.90, 6.40 and 6.65 μ.

(axi) A solution of 682 mg (1 mM) of an isomer mixture consisting of 2-[4-(benzoxazol-2-yldithio)-3-phenoxyacetamido-2-oxoazetidin-1-yl]-3-methoxy-crotonic acid diphenylmethyl ester and the corresponding isocrotonic acid diphenylmethyl ester in 20 ml of acetone/water, 9:1 (v/v) is stirred with 350 mg (1.3 mM) of silver p-toluenesulphinate for 90 minutes at room temperature. The mixture is filtered through Celite ® and the filtrate is concentrated to 5 ml in vacuo and extracted with 30 ml of methylene chloride. The methylene chloride phase is dried over sodium sulphate and concentrated by evaporation in vacuo. The residue is chromatographed on 30 g of acid-washed silica gel, using toluene/ethyl acetate, 1:1, and gives an isomer mixture consisting of 2-[4-(p-toluenesulphonylthio)-3-phenoxyacetamido-2-oxoazetidin-1-yl]3-methoxy-crotonic acid diphenylmethyl ester and the corresponding isocrotonic acid diphenylmethyl ester.

EXAMPLE 5

A solution of 300 mg (0.45 mmol) of the crystalline isomer mixture, obtainable according to Example 4(a), consisting of 2-[4-(p-toluenesulphonylthio)-3-phenox-acetamido-2-oxo-azetidin-1-yl]-3-methoxy-crotonic acid diphenylmethyl ester and the corresponding isocrotonic acid ester, in 4 ml of dry 1,2-dimethoxyethane is stirred with 0.134 ml (0.9 mmol) of 1,5-diazabicyclo[5.4.0]undec-5-ene at room temperature under nitrogen. After a reaction time of 40 minutes, the solution is cooled to 0° C. and 0.4 ml of acetic acid, followed by 180 mg (1.36 mmols) of m-chloroperbenzoic acid (85% strength) are added. The solution is stirred for 10 minutes at 0° C. under nitrogen, diluted with chloroform and washed with dilute sulphuric acid/sodium thiosulphate, water and dilute sodium bicarbonate solution. The aqueous phases are extracted with chloroform and the combined organic phases are dried over sodium sulphate, concentrated in vacuo and freed from the solvent under a high vacuum. The resulting crude product is separated on silica gel thick layer plates (running agent ethyl acetate, one development). The silica gel of the zone at Rf=0.51 is extracted with ethyl acetate, the resulting solution is concentrated and the residue is dried under a high vacuum. 7β-Phenoxyacetamido-3-methoxy-ceph-3-em-4-carboxylic acid diphenylmethyl ester 1β-oxide is obtained as an oily residue which crystallises from methylene chloride/pentane, melting point 115°–120° C.

7β-Phenoxyacetamido-3-methoxy-ceph-3-em-4-carboxylic acid diphenylmethyl ester 1α-oxide can be obtained by extracting the silica gel of the zone at Rf=0.22 with ethyl acetate, concentrating the solution on a rotary evaporator and drying the oily residue; melting point 175°–180° C. (from chloroform).

The same compounds can also be prepared according to Example (i) or (ii):

(i) A solution of 24.7 mg (36 mmols) of the crystalline isomer mixture obtainable according to Example 4(a), consisting of 2-[4-(p-toluenesulphonylthio)-3-phenoxyacetamido-2-oxoazetidin-1-yl]-3-methoxy-crotonic acid diphenylmethyl ester and the corresponding isocrotonic acid ester, in 247 ml of dry 1,2-dimethoxyethane is stirred with 8.22 ml (54 mmols) of 1,5-diazabicyclo[5.4.0]undec-5-ene at room temperature under nitrogen. After a reaction time of 40 minutes, the solution is cooled to 0° C. and 3.73 ml of formic acid are added, followed by 37.3 ml (108 mmols) of performic acid (prepared from 33 ml of hydrogen peroxide solution (30% strength) and 100 ml of formic acid). The solution is stirred for 10 minutes at 0° C. under nitrogen, diluted with chloroform and washed with dilute sulphuric acid/sodium thiosulphate, water and dilute sodium bicarbonate solution. The aqueous phases are extracted with chloroform and the combined organic phases are dried over sodium sulhate, concentrated in vacuo and freed from the solvent under a high vacuum. The resulting crude product is crystallised from methylene chloride/pentane and gives 7β-phenoxyacetamido-3-methoxy-ceph-3-em-4-carboxylic acid diphenylmethyl ester 1β-oxide of melting pint 115°–120° C.

(ii) A solution of 1.5 g (2.19 mmols) of the crystalline isomer mixture obtainable according to Example 4(a), consisting of 2-[4-(p-toluenesulphonylthio)-3-phenoxyacetamido-2-oxoazetidin-1-yl]-3-methoxy-crotonic acid diphenylmethyl ester and the corresponding isocrotonic acid ester, in 7.5 ml of dry 1,2-dimethoxyethane, is stirred with 0.43 ml (2.84 mmols) of 1,5-diazabicyclo[5.4.0]undec-5-ene at room temperature under nitrogen. After a reaction time of 40 minutes the solution is cooled to 0° C. and 0.375 ml (6.55 mmols) of acetic acid are added; followed by 0.667 ml (4.8 mmols) of 7.2 N peracetic acid. The solution is stirred for 20 minutes at 0° C. under nitrogen and 0.24 ml of sodium bisulphite solution (20% strength) is then added. 22.5 ml of water are added to the reaction mixture whilst stirring vigorously. Hereupon, a mixture of 7β-phenoxyacetamido-3-methoxy-ceph-3-em-4-carboxylic acid diphenylmethyl ester 1β-oxide and 1α-oxide crystallises out. The precipitate is filtered off, washed with water and dried under a high vacuum.

(iii) 32.9 ml (216 mmols) of 1,5-diazabicyclo[5.4.0]undec-5-ene are added to a suspension of 98.8 g (144 mmols) of 2-[4-(p-toluenesulphonylthio)-3-phenoxyacetamido-2-oxoazetidin-1-yl]-3-methoxy-isocrotonic acid diphenylmethyl ester in 988 ml of 1,2-dimethoxyethane over the course of 2 minutes at room temperature, under a nitrogen atmosphere, whilst stirring. The solution, which is now clear, is stirred for a further 25 minutes at rom temperature and then cooled to 0° C. whilst simultaneously adding 14.9 ml (395 mmols) of formic acid, and after cooling to −20° C. 149 ml of a mixture of 66 ml of hydrogen peroxide (30% strength) and 134 ml of formic acid (432 mmols of $H_2O_2$) are added dropwise. The reaction mixture is then stirred for 15 minutes at 0° C. and 37 g of sodium thiosulphate dissolved in 500 ml of water are then added. About 300 ml of water are added over the course of one hour at 5° C. After stirring for a further 2 to 3 hours at 5° C., the crystalline precipitate, which consists in the main of 7β-phenoxyacetamido-3-methoxy-ceph-3-em-4-carboxylic acid diphenylmethyl ester 1β-oxide is filtered off, washed with cold water (3° C.) and diethyl ether and dried over calcium chloride in a high vacuum.

7 liters of water are added to the filtrate at 5° C., whilst stirring vigorously. The initially oily precipitate, which solidifies on standing overnight, and which consists predominantly of 7β-phenoxyacetamido-3-methoxy-ceph-3-em-4-carboxylic acid diphenylmethyl ester 1α-oxide, is filtered off, washed with ice-cold water and dried over calcium chloride in a high vacuum.

(iv) 34.35 g (50 mmols) of 2-[4-(p-toluenesulphonyl-thio)-3-phenoxyacetamido-2-oxoazetidin-1-yl]-3-methoxy-isocrotonic acid diphenylmethyl ester are suspended in 340 ml of tetrahydrofurane at 20° C. under a nitrogen atmosphere (the bulk of the material dissolves). After rapid addition of 11.4 ml (75 mmols) of 1,5-diazabicyclo[5.4.0]undec-5-ene, the solution is stirred for 15 minutes at 20° C., 1.9 ml (30.2 mmols) of glacial acetic acid are then added and the mixture is concentrated to dryness in vacuo at 30° C. The brown, foamy residue is dissolved in 130 ml of methylene chloride and the solution is washed successively with 60 ml of water, 30 ml of 0.5 N hydrochloric acid, 30 ml of water, 30 ml of 1 M NaHCO₃ solution and 30 ml of water. The aqueous phases are extracted with twice 10 ml of methylene chloride.

The combined methylene chloride phases are cooled to −10° C. without first drying them, and 7.0 ml of peracetic acid/acetic acid (containing ~50 mmols of peracetic acid) are added slowly (the temperature rising to ~+10° C.). After stirring for 15 minutes at 0° C.–5° C., the excess peracetic acid is destroyed with aqueous sodium thiosulphate. The aqeuous phase is separated off and washed with a little methylene chloride. The solution is dried over magnesium sulphate and concentrated in vacuo. The light yellow residue, consisting of a mixture of 7β-phenoxyacetamido-3-methoxyceph-3-em-4-carboxylic acid diphenylmethyl ester 1-oxide and 7β-phenoxyacetamido-3-methoxy-ceph-2-em-4-carboxylic acid diphenylmethyl ester 1-oxide in the ratio of about 2:1, is dissolved in 120 ml of monoglyme at room temperature and 30 ml of water are added, whereupon 7β-phenylacetamido-3-methoxy-ceph-3-em-4-carboxylic acid diphenylmethyl ester 1β-oxide first crystallises out. The thick crystal sludge is first stirred for half an hour and then 150 ml of water are added over the course of about 5 hours at room temperature, whilst stirring, whereupon the corresponding 1α-oxide also crystallises out. After stirring for a total of 17 hours, the mixture is cooled for 1 hour in an icebath and then filtered, and the residue is washed with a little cooled monoglyme/water, 1:1.5. The crystals are dried for 16 hours over P₂O₅ in a high vacuum. 7β-Phenoxyacetamido-3-methoxyceph-3-em-4-carboxylic acid diphenylmethyl ester 1β-oxide, to which some of the corresponding 1α-oxide still adheres, is obtained.

The 1-oxides obtained can be further processed as follows:

(a) A solution of 150 mg (0.275 mmol) of 7β-phenoxyacetamido-3-methoxy-ceph-3-em-4-carboxylic acid diphenylmethyl ester 1β-oxide in 3 ml of methylene chloride and 0.1 ml of dimethylformamide is cooled to 0° C. and 188 mg (1.37 mmols) of phosphorus trichloride are then added. The solution is stirred for 30 minutes at 0° C., diluted with methylene chloride and washed with aqueous sodium bicarbonate solution. The aqueous phase is extracted with methylene chloride and the combined organic phases are dried over sodium sulphate and concentrated in vacuo. The resulting crude 7β-phenoxyacetamido-3-methoxy-ceph-3-em-4-carboxylic acid diphenylmethyl ester is recrystllised from ether; melting point 120° C.

(ai) A suspension of 5.0 g (9.16 mmols) of 7β-phenoxyacetamido-3-methoxy-ceph-3-em-4-carboxylic acid diphenylmethyl ester 1α-oxide in 25 ml of methylene chloride and 1.25 ml of dimethylacetamide is cooled to 0° C. and 1.69 ml (19.3 mmols) of phosphorus trichloride are then added. The solution is stirred for 30 minutes at 0° C., diluted with ethylene acetate and washed with aqueous sodium bicarbonate solution. The aqueous phase is extracted with ethyl acetate and the combined organic phases are dried over sodium sulphate and concentrated in vacuo. The resulting crude 7β-phenoxyacetamido-3-methoxyceph-3-em-4-carboxylic acid diphenylmethyl ester is recrystallised from ether; melting point 120° C.

(b) 0.87 ml of anisole is added to a solution of 2.0 g (3.78 mmols) of 7β-phenoxyacetamido-3-methoxyceph-3-em-4-carboxylic acid diphenylmethyl ester in 5 ml of methylene chloride and the mixture is cooled to 0° C. and left to stand for 1 hour after adding 1.2 ml of trifluoroacetic acid. The reaction mixture is concentrated in vacuo and the residue is crystallised from acetone/ether. 7β-Phenoxyacetamido-3-methoxy-ceph-3-em-4-carboxylic acid of melting point 170° C. (decomposition) is obtained.

The same compound can also be obtained without isolating the ester mentioned under (a): organic (bi) A suspension of 3.0 g (5.5 mmols) of a mixture of 7β-phenoxyacetamido-3-methoxy-ceph-3-em-4-carboxylic acid diphenylmethyl ester 1β-oxide and 1α-oxide in 15 ml of methylene chloride and 0.75 ml of dimethylacetamide is cooled to 0° C. and 0.966 ml (1.11 mmols) of phosphorus trichloride is then added. The solution is stirred at 0° C. for 40 minutes 4.65 ml (61 mmols) of trifluoroacetic acid are then added and stirring is continued for a further 30 minutes at 0° C. The reaction solution is rendered neutral with saturated sodium bicarbonate solution and the organic phase is washed with dilute bicarbonate solution. The combined aqueous phases are washed twice with ethyl acetate and brought to pH 2.6 with phosphoric acid. The 7β-phenoxyacetamido-3-methoxy-ceph-3-em-4-carboxylic acid which has precipitated is filtered off, washed with water and dried under a high vacuum; melting point 170° C. (decomposition).

(bii) A suspension of 53.4 g (97.7 mmols) of 7β-phenoxyacetamido-3-methoxy-ceph-3-em-4-carboxylic acid diphenylmethyl ester 1β-oxide [from Example 5iii] in 320 ml of methylene chloride and 16 ml of dimethylacetamide is cooled to 0° C. and 17.3 ml (19.8 mmols) of phosphorus trichloride are added slowly. After stirring for 20 minutes at 0°–5° C., 80 ml (1.05 mols) of trifluoroacetic acid are added dropwise. The clear solution is stirred for a further 20 minutes at 0°–5° C. and is then diluted with 1,300 ml of ethyl acetate and washed successively with 240 ml of 2 M dipotassium phosphate solution, 100 ml of water and 250 ml of half-saturated aqueous sodium chloride solution. 7β-Phenoxyacetamido-3-methoxy-ceph-3-em-4-carboxylic acid is extracted from the organic phase with 700 ml of saturated aqueous sodium bicarbonate solution and the aqueous portion is washed twice with 400 ml of ethyl acetate. The orgaic phases are extracted twice with a total of 250 ml of a solution composed of 50 ml of saturated aqueous sodium bicarbonate solution, 100 ml of water and 100 ml of saturated aqueous sodium chloride solution. The combined bicarbonate extracts are covered with 1,500 ml of ethyl acetate and the pH value of the solution is adjusted to ~ 2.5 with 20% strength phosphoric acid, while stirring vigorously. The aqueous phase is re-extracted twice with 500 ml of ethyl acetate. The combined organic phases are dried over magnesium sulphate, filtered and concentrated by evaporation in vacuo. The residue, which crystallises, is suspended in 130 ml of ethyl acetate and left to stand overnight at $-10°$ C. The pale yellow crystals of the resulting $7\beta$-phenoxyacetamido-3-methoxy-ceph-3-em-4-carboxylic acid are filtered off, washed with cooled ethyl acetate and dried to constant weight under a high vacuum.

(biii) A solution of 23.9 g of $7\beta$-phenoxyacetamido-3-methoxy-ceph-3-em-4-carboxylic acid diphenylmethyl ester $1\alpha$-oxide [from Example 5iii] in 140 ml of methylene chloride and 7.2 ml of dimethylacetamide is cooled to 0° C. and after slowly adding 7.8 ml of phosphorus trichloride the mixture is stirred for a further 20 minutes at 0°–5° C. 36 ml of trifluoroacetic acid are added dropwise to the reaction solution, and the mixture is then stirred for a further 20 minutes at 0°–5° C. and thereafter worked up as described under Example 5 (biii). $7\beta$-Phenoxyacetamido-3-methoxy-ceph-3-em-4-carboxylic acid is obtained in the form of a light yellow crystalline material.

(c) 0.7 ml (5.7 mmols) of dimethyl-dichloro-silane is added to a suspension of 2.55 g (7 mmols) of $7\beta$-phenoxyacetamido-3-methoxy-ceph-3-em-4-carboxylic acid and 2.9 ml (22.4 mmols) of N,N-dimethylaniline in 11 ml of absolute methylene chloride under nitrogen at 20° C. and the mixture is then stirred for 30 minutes at the same temperature. The resulting clear solution is cooled to $-20°$ C., 1.6 g (7.7 mmols) of solid phosphorus pentachloride are added and the mixture is stirred for 30 minutes. A precooled ($-20°$ C.) mixture of 0.9 ml (7 mmols) of N,N-dimethylaniline and 0.9 ml of n-butanol is added over the course of 2 to 3 minutes at the same temperature, 10 ml of precooled ($-20°$ C.) n-butanol are then added rapidly and the mixture is thereafter stirred for 20 minutes at $-20°$ C. and 10 minutes without cooling. 0.4 ml of water is added at about $-10°$ C., the mixture is stirred for about 10 minutes in an icebath (0° C.), 11 ml of dioxane are then added and after stirring for a further 10 minutes at 0° C. approx. 4.5 ml of tri-n-butylamine are added in portions until samples diluted with water assume a constant pH value of 3.5. After stirring for 1 hour at 0° C., the precipitate is filtered off, washed with dixane and recrystallised from water/dioxane. The resulting $7\beta$-amino-3-methoxy-ceph-3-em-4-carboxylic acid hydrochloride dioxanate has a melting point in excess of 300° C. Thin layer chromatogram: Rf value 0.17 (silica gel; system n-butanol/carbon tetrachloride/methanol/formic acid/water, 30:40:20:5:5).

(ci) 3.6 ml (3.87 g) of dimethyldichlorosilane are added to a suspension of 11.75 g of 93 percent strength (corresponding to 10.93 g of 100% strength) $7\beta$-phenoxyacetamido-3-methoxy-ceph-3-em-4-carboxylic acid and 13.4 ml (12.73 g) of N,N-dimethylaniline in 47 ml of absolute methylene chloride (distilled over $P_2O_5$) at $+20°$ C. under nitrogen, and the mixture is then stirred for 30 minutes at the same temperature. The solution, which is now clear, is cooled to $-18°$ C./$-19°$ C. and 7.8 g of solid phosphorus pentachloride are added, whereupon the internal temperature rises to $-10°$ C. After stirring for 30 minutes in a bath at $-20°$ C., the clear solution is added dropwise, over the course of approx. 7 minutes, to a mixture, cooled to $-20°$ C., of 47 ml of n-butanol (anhydrous, dried over Sikkan) and 4.4 ml (4.18 g) of dimethylaniline. Hereupon, the internal temperature rises to $-8°$ C. The mixture is stirred for a further 30 minutes, initially in the bath at $-20°$ C. and subsequently in an icebath (0° C.), so that a final internal temperature of $-10°$ C. is reached. At this temperature, a mixture of 47 ml of dioxane and 1.6 ml of water is added dropwise (duration approx. 5 minutes). Hereupon, the product slowly crystallises out. After stirring for a further 10 minutes, the mixture, in an icebath, is brought to a pH value of between 2.2 and 2.4, and kept thereat, by adding approx. 9.5 ml of tri-n-butylamine in portions over the course of approx. 1 hour (the first 5 ml being added in the first 5 minutes). Thereafter the product is filtered off and washed in portions with approx. 30 ml of dioxane and then with approx. 15 ml of methylene chloride, thus giving crystalline $7\beta$-amino-3-methoxy-ceph-3-em-4-carboxylic acid hydrochloride dioxanate; melting point above 300° C.; UV spectrum (in 0.1 N sodium bicarbonate): $\lambda_{max}=270$ m$\mu$ ($\epsilon=7,600$); IR spectrum (Nujol): characteristic bands at 5.62; 5.80; 5.88; 6.26; 6.55; 7.03; 7.45; 7.72; 7.96; 8.14; 8.26; 8.45; 8.64; 8.97; 9.29; 10.40 and 11.47 m$\mu$; $[\alpha]_D^{20} = +134° \pm 10°$ (c = 1; 0.5 N sodium bicarbonate solution).

The zwitter-ion of $7\beta$-amino-3-methoxy-ceph-3-em-4-carboxylic acid can be obtained from the resulting hydrochloride dioxanate by adding 2 N sodium hydroxide solution to a 20% strength aqueous solution of the dioxanate until the pH value is 4.1 (isoelectric point); when filtered off and dried, the product has a melting point in excess of 300° C. UV spectrum (in 0.1 N sodium bicarbonate solution) $\lambda_{max}=270$ nm ($\epsilon=7,600$). Thin layer chromatogram: Rf value identical with that of the hydrochloride (silica gel, same system); $[\alpha]_D^{20}$ +232° ±1° (c=1; 0.5 N sodium bicarbonate solution).

(d) 1.65 ml of bis-(trimethylsilyl)-acetamide are added to a suspension of 1 g (2.82 mmols) of $7\beta$-amino-3-methoxy-ceph-3-em-4-carboxylic acid hydrochloride dioxanate in 20 ml of dry methylene chloride at room temperature under a nitrogen atmosphere. After 40 minutes, the clear solution is cooled to 0° C. and 900 mg (4.37 mmols) of solid D-$\alpha$-phenylglycyl chloride hydrochloride are added. Five minutes later, 0.7 ml (10 mmols) of propylene oxide is added. The suspension is then stirred for 1 hours at 0° C. under a nitrogen atmosphere and 0.5 ml of methanol is then added, whereupon $7\beta$-(D-$\alpha$-phenylglycylamino)-3-methoxy-ceph-3-em-4-carboxylic acid hydrochloride precipitates in a crystalline form. The hydrochloride is filtered off and dissolved in 9 ml of water, and the pH of the solution is adjusted to 4.6 with 1 N sodium hydroxide solution. The dihydrate of the inner salt of $7\beta$-(D-$\alpha$-phenylglycylamino)-3-methoxy-ceph-3-em-4-carboxylic acid which precipitates, is filtered off, washed with acetone and diethyl ether and dried; melting point 174°–176° C. (decomposition); $[\alpha]_D^{20} = +132°$ (c=0.714; in 0.1 N hydrochloric acid); thin layer chromatogram (silica gel): Rf value ~0.18 (system: n-butanol/acetic acid/water, 67:10:23). UV spectrum (in 0.1 N aqueous sodium bicarbonate solution) $\lambda_{max}=269$ $\mu$ ($\epsilon=7,000$); IR spectrum (in mineral oil): characteristic bands at 5.72, 5.94, 6.23 and 6.60 μ.

(di) 1.37 ml (5.6 mmols) of N,N-bis-(trimethylsilyl)-acetamide are added to a suspension of 993 mg (4.32 mmols) of 7β-amino-3-methoxy-ceph-3-em-4-carboxylic acid (inner salt) in 10 ml of methylene chloride and the mixture is stirred for 45 minutes at room temperature under a nitrogen atmosphere. The clear solution is cooled to 0° C. and 1.11 g (5.4 mmols) of D-α-phenylglycyl chloride hydrochloride are added. After 5 minutes, 0.4 ml (5.6 mmols) of propylene oxide is added. The suspension is then stirred for 1 hour at 0° C. under a nitrogen atmosphere and thereafter 0.6 ml of methanol is added. 7β-(D-α-Phenylglycylamido)-3-methoxy-ceph-3-em-4-carboxylic acid hydrochloride, which crystallises out, is filtered off and dissolved in 15 ml of water at 0° C., and the pH of the solution is adjusted to about 4 with 5 ml of 1 N sodium hydroxide solution. The solution is warmed to room temperature and its pH is brought to about 4.8 with triethylamine, whereupon 7β-(D-α-phenylglycylamido)-3-methoxy-ceph-3-em-4-carboxylic acid crystallises out in the form of the dihydrate.

EXAMPLE 6

A solution of 0.228 g (1.5 mM) of 1,5-diazabicyclo[5.4.0]undec-5-ene in 10 ml of tetrahydrofurane is added to a solution of 0.697 g (1.0 mM) of an isomer mixture consisting of 2-[4-(benzthiazol-2-yldithio)-3-phenoxyacetamido-2-oxo-azetidin-1-yl]-3-methoxy-crotonic acid diphenylmethyl ester and the corresponding isocrotonic acid diphenylmethyl ester in 4 ml of dry tetrahydrofurane. The mixture is stirred for 40 minutes at room temperature, diluted with 200 ml of benzene and washed successively with dilute hydrochloric acid, sodium bicarbonate solution and water. The organic phase is dried over sodium sulphate and the solvent is removed in vacuo. The resulting crude product is chromatographed on 30 g of silica gel which has been washed with hydrochloric acid. Toluene/ethyl acetate, 7:1, first elutes 2-mercaptobenzthiazole and subsequently 7β-phenoxyacetamido-3-methoxy-ceph-2-em-4-carboxylic acid diphenylmethyl ester. IR spectrum (in $CH_2Cl_2$): 5.60, 5.74, 5.90 and 8.28 μ.

The ester obtained can be converted into the free acid as follows:

(i) A mixture of 53 mg (0.1 mmol) of 7β-phenoxyacetamido-3-methoxy-ceph-2-em-4α-carboxylic acid diphenylmethyl ester, 0.07 ml of trifluoroacetic acid, 0.06 ml of anisole and 0.5 ml of methylene chloride is stirred for 15 hours at 0° C. The mixture is diluted with 5 ml of pentane/diethyl ether, 3:1, and shaken vigorously. The white, amorphous 7β-phenoxyacetamido-3-methoxy-ceph-2-em-4α-carboxylic acid which precipitates is filtered off and washed with pentane/diethyl ether, 3:1. IR spectrum ($CH_2Cl_2$): 5.60, 5.90 and 8.27 μ.

The starting material can be obtained as follows:

(a) 1 equivalent of ozone (diluted with oxygen) is passed into a solution, cooled to −70° C., of 681 mg (1.0 mM) of 2-[4-(benzthiazol-2-yldithio)-3-phenoxyacetamido-2-oxoazetidin-1-yl]-3-methylene-butyric acid diphenylmethyl ester in 30 ml of ethyl acetate. The reaction solution is allowed to warm up, concentrated to 10 ml in vacuo, mixed with 1.0 ml of dimethyl sulphide and stirred for 15 hours at room temperature. Solvent and excess reagent are removed in vacuo and the residue is chromatographed on 30 g of acid-washed silica gel, using toluene/ethyl acetate, 4:1 (15 ml fractions). 2-[4-(Benzthiazol-2-yldithio)-3-phenoxyacetamido-2-oxoazetidin-1-yl]-3-hydroxy-crotonic acid diphenylmethyl ester is obtained as a solid amorphous substance. $[α]_D = 130°$ ±1° ($CHCl_3$; c=0.8) IR spectrum ($CH_2Cl_2$): 2.95, 5.60, 5.92, 6.04 and 8.10 μ.

(b) A distilled solution of diazomethane in ether (containing 1.3 mM of diazomethane) is added to a solution of crude 2-[4-(benzthiazol-2-yldithio)-3-phenoxyacetamido-2-oxo-azetidin-1-yl]-3-hydroxy-crotonic acid diphenylmethyl ester, obtained by ozonisation of 681 mg (1.0 mM) of 2-[4-(benzthiazol-2-yldithio)-3-phenoxyacetamido-2-oxoazetidin-1-yl]-3-methylene-butyric acid diphenylmethyl ester, in 5 ml of methylene chloride at 0° C. The mixture is stirred for one hour at 0° C. and washed with water, and the organic layer is dried over sodium sulphate. The solvents are removed in vacuo and the residue is chromatographed on 35 g of acid-washed silica gel, using toluene/ethyl acetate, 2:1. An isomer mixture consisting of 2-[4-(benzthiazol-2-yldithio)-3-phenoxyacetamido-2-oxoazetidin-1-yl]-3-methoxy-crotonic acid diphenylmethyl ester and the corresponding isocrotonic acid diphenylmethyl ester is obtained. IR spectrum (in $CH_2Cl_2$): 5.60, 5.88, 6.67, 9.15 and 9.92 μ.

EXAMPLE 7

Analogously to Example 4, 200 mg (0.307 mM) of an isomer mixture consisting of 2-[4-(p-toluenesulphonyl-thio)-3-phenoxyacetamido-2-oxoazetidin-1-yl]-3-methoxy-crotonic acid 2,2,2-trichloroethyl ester and the corresponding isocrotonic acid 2,2,2-trichloroethyl ester and 0.09 ml (0.6 mM) of 1,5-diazabicyclo[5.4.0]undec-5-ene, on stirring for 30 minutes at room temperature in 3 ml of 1,2-dimethoxyethane, give an isomer mixture consisting of 7β-phenoxyacetamido-3-methoxy-ceph-2-em-4-carboxylic acid 2,2,2-trichloroethyl ester and 7β-phenoxyacetamido-3-methoxy-ceph-3-em-4-carboxylic acid 2,2,2-trichloroethyl ester (in the ratio of about 1:1). Rf values = 0.36 and 0.18 respectively (silica gel; toluene/ethyl acetate, 3:1).

The starting material can be obtained as follows:

(a) Analogously to Example 1b), 498 mg (1 mM) of 6-phenoxyacetamido-penicillanic acid 2,2,2-trichloroethyl ester and 200.7 mg (1.2 mM) of 2-mercaptobenzthiazole give 2-[4-(benzthiazol-2-yldithio)-3-phenoxyacetamido-2-oxoazetidin-1-yl]-3-methylene-butyric acid 2,2,2-trichloroethyl ester; melting point 144–149° C. (from methylene chloride/pentane), Rf value = 0.5 (silica gel; ether).

(b) Analogously to Example 6a), 647 mg (1 mM) of 2-[4-(benzthiazol-2-yldithio)-3-phenoxyacetamido-2-oxoazetidin-1-yl]-3-methylene-butyric acid 2,2,2-trichloroethyl ester and 1.2 equivalents of ozone, with subsequent splitting of the ozonide with dimethyl sulphide, give 2-[4-(benzthiazol-2-yldithio)-3-phenoxyacetamido-2-oxoazetidin-1-yl]-3-hydroxy-crotonic acid 2,2,2-trichloroethyl ester; melting point 129–130° C. (ether/petroleum ether).

(c) Analogously to Example 6b), 5 g (7.71 mM) of 2-[4-(benzthiazol-2-yldithio)-3-phenoxyacetamido-2-oxoazetidin-1-yl]-3-hydroxy-crotonic acid 2,2,2-trichloroethyl ester and an excess of diazomethane give the isomer mixture consisting of 2-[4-(benzthiazol-2-yldithio)-3-phenoxyacetamido-2-oxoazetidin-1-yl]-3-methoxy-crotonic acid 2,2,2-trichloroethyl ester and the corresponding isocrotonic acid 2,2,2-trichloroethyl ester; melting point 170–174° C. (from methylene chloride/ether).

(d) Analogously to Example 1(c), 1.9 g (2.87 mM) of an isomer mixture consisting of 2-[4-(benzthiazol-2-yldithio)-3-phenoxyacetamido-2-oxoazetidin-1-yl]-3-methoxy-crotonic acid 2,2,2-trichloroethyl ester and the corresponding isocrotonic acid 2,2,2-trichloroethyl ester, on stirring for five hours at room temperature with 0.8 g (4.05 mM) of silver p-toluenesulphinate in 35 ml of acetonitrile/ethyl acetate, 3:4, give an isomer mixture consisting of 2-[4-(p-toluenesulphonylthio)-3-phenoxyacetamido-2-oxoazetidin-1-yl]-3-methoxy-crotonic acid 2,2,2-trichloroethyl ester and the corresponding isocrotonic acid 2,2,2-trichloroethyl ester; melting point 155–158° C. (from ethyl acetate/ether).

EXAMPLE 8

0.02 ml (0.16 mmol) of trimethylchlorosilane is added to a solution of 100 mg (0.146 mmol) of 2-[4-(benzthiazol-2-yldithio)-3-phenoxyacetamido-2-oxoazetidin-1-yl]-3-hydroxy-crotonic acid diphenylmethyl ester in 2 ml of dry methylene chloride at 0° C. 0.0477 ml (0.32 mmol) of 1,5-diazabicyclo[5.4.0]undec-5-ene is added to this solution under nitrogen, whilst stirring, and the mixture is stirred for a further hour at 0° C. After addition of 0.2 ml of acetic acid, the mixture is diluted with methylene chloride. The organic phase is successively washed with dilute sulphuric acid, water and aqueous sodium bicarbonate solution, dried over sodium sulphate and concentrated to dryness in vacuo.

The resulting crude 7$\beta$-phenoxyacetamido-3-hydroxy-ceph-3-em-4-carboxylic acid diphenylmethyl ester is dissolved in methanol and a solution of diazomethane in ether is added at 0° C. After 10 minutes, the solution is carefully concentrated and the residue is dried under a high vacuum. The residue is purified by thick layer chromatography (toluene/ethyl acetate, 3:1, silica gel). After eluting the silica gel of the zone at Rf = 0.17 with ethyl acetate, and concentrating the solution on a rotary evaporator, 7$\beta$-phenoxyacetamido-3-methoxy-ceph-3-em-4-carboxylic acid diphenylmethyl ester is obtained; melting point 120° C. (from ether).

EXAMPLE 9

A solution of 266 mg (0.5 mM) of a crude mixture consisting of 2-[4-(benzthiazol-2-yldithio)-3-phenoxyacetamido-2-oxoazetidin-1-yl ]-3-methoxy-crotonic acid chloride and 2-[4-(benzthiazol-2-yldithio)-3-phenoxyacetamido-2-oxoazetidin-1-yl]-3-methoxy-isocrotonic acid chloride in 5 ml of dry methylene chloride is added dropwise over the course of 15 minutes at 0° C., whilst stirring, to a solution of 0.10 ml of triethylamine in 0.5 ml of dry tert.-butanol and 3 ml of methylene chloride. After a further 15 minutes stirring, the reaction mixture is diluted with methylene chloride, washed with water, with dilute hydrochloric acid and again with water, dried over sodium sulphate and concentrated by evaporation in vacuo. The residue is chromatographed on 10 g of acid-washed silica gel, using toluene/ethyl acetate (4:1) as the running agent. 7$\beta$-Phenoxyacetamido-3-methoxy-ceph-2-em-4-carboxylic acid tert.butyl ester is obtained. IR spectrum (in $CH_2CL_2$): characteristic bands at 5.60, 5.77, 5.90 and 8.29 $\mu$.

The starting material can be obtained as follows:

(a) A mixture of 0.7 ml of trifluoroacetic acid, 0.6 ml of anisole and 2.5 ml of methylene chloride is added slowly to a solution of 698 mg (1 mM) of a mixture consisting of 2-[4-(benzthiazol-2-yldithio)-3-phenoxyacetamido-2-oxoazetidin-1-yl]-3-methoxy-crotonic acid diphenylmethyl ester and 2-[4-(benzthiazol-2-yldithio)-3-phenoxyacetamido-2-oxoazetidin-1-yl]-3-methoxy-isocrotonic acid dihenylmethyl ester in 1.5 ml of methylene chloride at 0° C., while stirring. The reaction mixture is stirred for 3 hours at 0° C. and then shaken with 100 ml of ether/pentane, 1:3, and the precipitate is filtered off. It consists of a mixture of 2-[4-(benzthiazol-2-yldithio)-3-phenoxyacetamido-2-oxoazetidin-1-yl]-3-methoxy-crotonic acid and 2-[4-(benzthiazol-2-yldithio)-3-phenoxyacetamido-2-oxoazetidin-1-yl]-3-methoxy-isocrotonic acid, and is washed with 25 ml of ether/pentane, 1:3, and dried in vacuo. IR spectrum (in $CH_2Cl_2$): characteristic bands at 5.60, 5.80, 5.94, 8.55 and 9.95 $\mu$.

(b) A solution of 532 mg (1.0 mM) of a mixture consisting of 2-[4-(benzthiazol-2-yldithio)-3-phenoxyacetamido-2-oxo-azetidin-1-yl]-3-methoxy-crotonic acid and 2-[4-(benzthiazol-2-yldithio)-3-phenoxyacetamido-2-oxoazetidin-1-yl]-3-methoxyisocrotonic acid in 5 ml of dry dioxane, containing 10% of oxalyl chloride, is stirred for 15 hours at room temperature and then concentrated by evaporation in vacuo. The solid, non-crystalline residue, consisting of a mixture of 2-[4-(benzthiazol-2-yldithio)-3-phenoxyacetamido-2-oxoazetidin-1-yl]-3-methoxy-crotonic acid chloride and 2-[4-(benzthiazol-2-yldithio)-3-phenoxyacetamido-2-oxoazetidin-1-yl]-3-methoxyisocrotonic acid chloride can be converted further without additional purification. IR spectrum (in $CH_2Cl_2$): characteristic bands at 5.58, 5.90 and 9.95 $\mu$.

EXAMPLE 10

A solution of 367 mg (0.5 mM) of a mixture consisting of 2-[4-(p-nitrobenzenesulphonylthio)-3-phenoxyacetamido-2-oxoazetidin-1-yl]-3-methoxy-crotonic acid diphenylmethyl ester and the corresponding isocrotonic acid dihenylmethyl ester, and 152 mg (1.0 mM) of 1,5-diazabicyclo[5.4.0]undec-5-ene in 10 ml of dry tetrahydrofurane is stirred for 40 minutes at room temperature. The reaction mixture is diluted with benzene, washed successively with dilute hydrochloric acid, water and dilute aqueous sodium bicarbonate solution, dried over sodium sulphate and freed from the solvent in vacuo. The residue is chromatographed on acid-washed silica gel, using toluene/ethyl acetate, 7:1, as the running agent, whereby pure 7$\beta$-phenoxyacetamido-3-methoxy-ceph-2-em-4-carboxylic acid diphenylmethyl ester is obtained. Subsequent elution with toluene/ethyl acetate, 2:1, results in the isolation of a mixture which in addition to 7$\beta$-phenoxyacetamido-3-methoxy-ceph-2-em-4-carboxylic acid diphenylmethyl ester also contains 7$\beta$phenoxyacetamido-3-methoxy-ceph-3-em-4-carboxylic acid diphenylmethyl ester.

The starting materials can be prepared as follows:

(a) Analogously to Example 4ai), 348.5mg (0.5 mM) of an isomer mixture consisting of 2-[4-(benzthiazol-2-ylthio)-3-phenoxyacetamido-2-oxoazetidin-1-yl]-3-methoxy-crotonic acid diphenylmethyl ester and the corresponding isocrotonic acid diphenylmethyl ester, and 200 mg (0.68 mM) of silver p-nitrobenzenesulphinate, on stirring for one hour at 60° C. in 10 ml of acetone/water, 9:1, give a mixture consisting of 2-[4-(p-nitrobenzenesulphonylthio)-3-phenoxyacetamido-2-oxoazetidin-1-yl]-3-methoxy-crotonic acid diphenylmethyl ester and the corresponding isocrotonic acid diphenylmethyl ester.

Silver p-nitrobenzenesulphinate is obtained by combining aqueous solutions of equimolar amounts of silver nitrate and sodium p-nitrobenzenesulphinate. The precipitate is filtered off and dried in vacuo for 24 hours at 50–60° C.

EXAMPLE 11

Analogously to Example 10, 351.5 mg (0.5 mM) of an isomer mixture consisting of 2-[4-(p-methoxybenzenesulphonylthio)-3-phenoxyacetamido-2-oxoazetidin-1-yl]-3-methoxy-crotonic acid diphenylmethyl ester and the corresponding isocrotonic acid diphenylmethyl ester, and 152 mg (1 mM) of 1,5-diazabicyclo[5.4.0]undec-5-ene, give a mixture consisting of 7β-phenoxyacetamido-3-methoxy-ceph-2-em-4-carboxylic acid diphenylmethyl ester and 7β-phenoxyacetamido-3-methoxy-ceph-3-em-4-carboxylic acid diphenylmethyl ester, which can be separated into the two isomers by chromatography.

The starting materials can be obtained as follows:

(a) Analogously to Example 4(ai), 697 mg (1 mM) of an isomer mixture consisting of 2-[4-(benzthiazol-2-ylthio)-3-phenoxyacetamido-2-oxoazetidin-1-yl]-3methoxy-crontonic acid diphenylmethyl ester and the corresponding isocrotonic acid diphenylmethyl ester, and 361 mg (1.3 mM) of silver p-methoxybenzenesulphinate, on stirring for one hour at room temperature in 20 ml of acetone/water, 9:1, give a mixture consisting of 2-[4-(p-methoxybenzenesulphonylthio)-3-phenoxyacetamido-2-oxoazetidin-1-yl]-3-methoxy-crotonic acid diphenylmethyl ester and the corresponding isocrotonic acid diphenylmethyl ester. IR spectrum (in $CH_2CL_2$): characteristic bands at 5.60, 5.88, 6.18 and 8.76 μ.

Silver p-methoxybenzenesulphinate is obtained by combining aqueous solutions of equimolar amounts of silver nitrate and sodium p-methoxybenzenesulphinate. The precipitate is filtered off and dried in vacuo for 24 hours at 50–60° C.

EXAMPLE 12

Analogously to Example 10, 336.3 mg (0.5 mM) of an isomer mixture consisting of 2-(4-benzenesulphonylthio-3-phenoxyacetamido-2-oxoazetidin-1-yl)-3-methoxy-crotonic acid diphenylmethyl ester and the corresponding isocrotonic acid diphenylmethyl ester, and 152 mg (1 mM) of 1,5-diazabicyclo-[5.4.0]undec-5-ene, give a mixture consisting of 7β-phenoxyacetamido-3-methoxy-ceph-2-em-4-carboxylic acid diphenylmethyl ester and 7β-phenoxyacetamido-3-methoxy-ceph-3-em-4-carboxylic acid diphenylmethyl ester, which can be separated into the two isomers by chromatography.

The starting materials can be obtained as follows:

(a) Analogously to Example 4ai), 697 mg (1 mM) of an isomer mixture consisting of 2-[4-benzthiazol-2-ylthio)-3-phenoxyacetamido-2-oxoazetidin-1-yl]-3-methoxy-crotonic acid diphenylmethyl ester and the corresponding isocrotonic acid diphenylmethyl ester, and 324 mg (1.3 mM) of silver benzenesulphinate, on stirring for 90 minutes at room temperature in 20 ml of acetone/water, 9:1, give a mixture consisting of 2-(4-benzenesulphonylthio-3-phenoxyacetamido-2-oxoazetidin-1-yl)-3-methoxy-crotonic acid diphenylmethyl ester and the corresponding isocrotonic acid diphenylmethyl ester. IR spectrum (in $CH_2Cl_2$): characteristic bands at 5.60, 5.88 and 8.74 μ.

Silver benzenesulphinate is obtained by combining aqueous solutions of equimolar amounts of silver nitrate and sodium benzenesulphinate. The precipitate is filtered off and dried in vacuo for 24 hours at 50–60° C.

EXAMPLE 13

Analogously to Example 1, an isomer mixture consisting of 7β-phenoxyacetamido-3-methoxy-ceph-3-em-4-carboxylic acid p-nitrobenzyl ester and 7β-phenoxyacetamido-3-methoxy-ceph-2-em-4-carboxylic acid p-nitrobenzyl ester can be obtained from the isomer mixture consisting of 2-[4-(p-toluenesulphonylthio)-3-phenoxyacetamido-2-oxoazetidin-1-yl]-3-methoxy-crotonic acid p-nitrobenzyl ester and the corresponding isocrotonic acid ester, by stirring for 12 to 14 hours at room temperature with tetramethylguanidine in tetrahydrofurane.

EXAMPLE 14

A mixture of 104.5 mg (0.15 mM) of an isomer mixture consisting of 2-[4-(benzthiazol-2-ylthio)-3-phenoxyacetamido-2-oxoazetidin-1-yl]-3-methoxy-crotonic acid diphenylmethyl ester and the corresponding isocrotonic acid diphenylmethyl ester, 35 mg (0.225 mM) of p-toluenesulphinic acid and 80 mg (0.525 mM) of 1,5-diazabicyclo[5.4.0]undec-5-ene in 3 ml of dry tetrahydrofurane is stirred for 40 minutes at room temperature. The mixture is diluted with benzene and washed successively with dilute hydrochloric acid, with dilute aqueous sodium chloride solution, with 0.5 N sodium hydroxide solution and again with dilute aqueous sodium chloride solution. The organic phase is dried over sodium sulphate and freed from the solvent in vacuo. Chromtography of the residue on 3.5 g of acid-washed silica gel, using toluene/ethyl acetate, 7:1, first gives pure 7β-phenoxyacetamido-3-methoxy-ceph-2-em-4α-carboxylic acid diphenylmethyl ester. Toluene/ethyl acetate, 2:1, subsequently elutes 7β-phenoxyacetamido-3-methoxy-ceph-3-em-4-carboxylic acid diphenylmethyl ester.

EXAMPLE 15

A mixture of 141 mg (0.2 mM) of 2-[4-(o-methoxybenzenesulphonylthio)-3-phenoxyacetamido-2-oxoazetidin-1-yl]-3-methoxy-crotonic acid diphenylmethyl ester and 61 mg (0.4 mM) of 1,4-diazabicyclo[5.4.0]undec-5-ene in 4 ml of dry tetrahydrofurane is stirred for 70 minutes at room temperature. Working up analogously to Example 10 gives a crude mixture consisting of 7β-phenoxyacetamido-3-methoxy-ceph-2-em-4α-carboxylic acid diphenylmethyl ester and 7β-phenoxyacetamido-3-methoxy-ceph-3-em-4-carboxylic acid diphenylmethyl ester in the ratio of about 4.4:1, which can be separated into the two isomers by chromatography on silica gel, analogously to Example 10.

mM) two compounds are produced in approximately the same ratio if 141 g (0.2 mM9) of 2-[4-(o-methoxybenzenesulphonylthio)-3-phenoxyacetamido-2-oxoazetidin-1-yl]-3-methoxyisocrotonic acid diphenylmethyl ester are treated analogously.

The two isomeric starting materials can be obtained as follows:

(a) 3.49 g (5 mM) of an isomer mixture consisting of 2-[4-(benzthiazol-2-ylthio)-3-phenoxyacetamido-2-oxoazetidin-1-yl]-3-methoxy-crotonic acid diphenylmethyl ester and the corresponding isocrotonic acid diphenylmethyl ester in the ratio of about 4:1 are stirred with 1.82 g (6.5 mM) of silver o-methoxybenzenesulphinate in 100 ml of acetone/water, 9:1, for 130 minutes at room temperature. The mixture is filtered and the filtrate is concentrated by evaporation in vacuo. The residue is chromatographed on 140 g of acid-washed silica gel, using toluene/ethyl acetate, 1:1. 50 ml fractions are collected; of these, fractions 7 to 13 contain pure 2-[4-(o-methoxybenzenesulphonylthio)-3-phenoxyacetamido-2-oxoazetidin-1-yl]-3-methoxy-isocrotonic acid diphenylmethyl ester, IR spectrum (CH$_2$Cl$_2$): 5.60, 5.90, 8.72 and 9.15 $\mu$, and fraction 25 and the subsequent fractions give pure 2 -[4-(o-methoxybenzenesulphonylthio)-3-phenoxyacetamido-2-oxoazetidin-1-yl]-3-methoxy-crotonic acid diphenylmethyl ester, IR spectrum (CH$_2$Cl$_2$): 5.60, 5.90, 8.20, 8.30, 8.72, and 9.80 $\mu$. Fractions 14 to 24 contain mixtures of the two isomers.

EXAMPLE 16

A mixture of 57 mg (0.1 mM) of crude 2-[4-(o-methoxybenzenesulphonylthio)-3-phenoxyacetamido-2-oxoazetidin-1-yl]-3-methoxy-isocrotonic acid chloride and 43 mg (0.3 mM) of 1,5-diazabicyclo[5.4.0]undec-5ene in 2 ml of dry methylene chloride is stirred for 80 minutes at room temperature. The mixture is diluted with methylene chloride, washed with dilute hydrochloric acid and water, dried over sodium sulphate and freed from the solvent in vacuo. The residue is dissolved in 0.5 ml of methylene chloride, 5 ml of pentane/diethyl ether, 3:1, are added, and the mixture is shaken. The precipitate is filtered off and washed with pentane/diethyl ether, 3:1. It consists of fairly pure 7$\beta$-phenoxyacetamido-3-methoxy-ceph-2-em-4-carboxylic acid.

The starting material can be obtained as follows:

(a) A mixture of 703 mg (1 mM) of pure 2-[4-(o-methoxybenzenesulphonylthio)-3-phenoxyacetamido-2-oxoazetidin-1-yl]-3-methoxy-isocrotonic acid diphenylmethyl ester, 0.7 ml of trifluoroacetic acid and 0.66 ml of anisole in 4 ml of methylene chloride is stirred for 3 hours at 0° C. 50 ml of pentane/diethyl ether, 3:1, are then added to the mixture and the whole is shaken vigorously. The white precipitate of pure 2-[4-(o-methoxybenzenesulphonylthio)-3-phenoxyacetamido-2-oxoazetidin-1-yl]-3-methoxy-isocrotonic acid is filtered off and washed with pentane/diethyl ether, 3:1. IR spectrum (CH$_2$Cl$_2$): 5.60, 5.93, 6.25 and 8.72 $\mu$.

(b) One drop of dimethylformamide in dioxane is added to a soltuion of 54 mg (0.1 mM) of 2-[4-(o-methoxybenzensulphonylthio)-3-phenoxyacetamido-2-oxoazetidin-1-yl]-3-methoxy-isocrotonic acid in 0.5 ml of a 10% strength solution of oxalyl chloride in dioxane, whereupon an evolution of gas occurs immediately. The mixture is stirred for 2 hours at room temperature and the solvent and the excess oxalyl chloride are evaporated off in vacuo. The residue is dried in a high vacuum and gives 2-[4-(o-methoxybenzenesulphonylthio)-3-phenoxyacetamido-2-oxoazetidin-1yl]-3-methoxy-isocrotonic acid chloride in the form of a slightly orange-coloured foam, IR spectrum (CH$_2$Cl$_2$): 5.60, 5.90 and 8.70 $\mu$.

Example 17

A solution of 200 mg (0.254 mM) of 2-[4-(p-toluenesulphonylthio)-3-(D-$\alpha$-tert.-butoxycarbonylamino-$\alpha$-phenylacetylamino)-2-oxoazetidin-1-yl]-3-methoxy-crotonic acid diphenylmethyl ester in 2 ml of dimethylformamide is stirred with 57 $\mu$l (0.38 mM) of 1,5-diazabicyclo[5.4.0]undec-5-ene for 30 minutes at room temperature, ethyl acetate is then added and the mixture is washed with water and 2 N hydrochloric acid until it gives an acid reaction, and with saturated aqueous sodium chloride solution until it gives a neutral reaction. The organic phase is dried over sodium sulphate and concentrated by evaporation in vacuo. The residue is chromatographed on silica gel thick layer plates, using toluene/ethyl acetate, 1:1, as the running agent. 7$\beta$-(D-$\alpha$-tert.butylcarbonylamino-$\alpha$-phenylacetylamino)-3-methoxy-ceph-2-em-4$\alpha$-carboxylic acid diphenylmethyl ester of melting point 166°-168° C. (methylene chloride/pentane); thin layer chromatogram (silica gel; diethyl ether): Rf value $\sim$0.51; UV spectrum (in ethanol): $\lambda_{max}$=257 m$\mu$ ($\epsilon$=3,500); IR spectrum (in methylene chloride): characteristic bands at 2.96, 5.63, 5.74, 5.85 (shoulder), 5.92, 6.16, 6.64 and 6.72 $\mu$; and 7$\beta$-(D-$\alpha$-tert.butylcarbonylamino-$\alpha$-phenylacetylamino)-3-methoxy-ceph-3-em-4-carboxylic acid diphenylmethyl ester of melting point 162°-163° C. (diethyl ether); thin layer chromatogram: Rf value: $\sim$0.33 (silica gel; diethyl ether); UV spectrum (in ethanol) $\lambda_{max}$=265 m$\mu$ ($\epsilon$=6,600); 280 m$\mu$ (shoulder) ($\epsilon$=6,200); IR spectrum (in methylene chloride): 2.92, 5.58, 5.64 (shoulder), 5.82, 6.22 and 6.67 $\mu$ are obtained.

The compounds obtained can be converted further as follows:

(a) A mixture of 8.8 g of 7$\beta$-(D-$\alpha$-tert.butoxycarbonylamino$\alpha$-phenyl-acetylamino)-3-methoxy-3-ceph-em-4-carboxylic acid diphenylmethyl ester. 8.6 ml of anisole and 145 ml of trifluoroacetic acid is stirred for 15 minutes at 0° C., 400 ml of pre-cooled toluene are then added and the mixture is concentrated by evaporation under reduced pressure. The residue is dried under a high vacuum, digested with diethyl ether and filtered off. This gives the trifluoroacetate of 7$\beta$-(D-$\alpha$-phenylglycylamino)-3-methoxy-3-cephem-4-carboxylic acid in the form of a powder. The material is dissolved in 20 ml of water, the solution is washed with twice 25 ml of ethyl acetate and the pH is adjusted to a value of about 5 with a 20% strength solution of triethylamino in methanol, whereupon a colourless precipitate forms. This mixture is stirred for one hour in an icebath, 20 ml of acetone are then added and the whole is left to stand for 16 hours at about 4° C. The colourless precipitate is filtered off, washed with acetone and diethyl ether and dried under reduced pressure. This gives, in the form of a micro-crystalline powder, 7$\beta$-(D-$\alpha$-phenylglycylamino)-3-methoxy-3-cephem-4-carboxylic acid as the inner salt, which furthermore, is present in the form of a hydrate, melting point 174°-176° C. (with decomposition); [$\alpha$]$^{20}_D$=+149° (c = 1.03 in 0.1 N hydrochloric acid); thin layer chromatogram (silica gel; development with iodine): Rf $\sim$0.36 (system: n-butanol/-pyridine/acetic acid/water, 40:24:6:30); ultraviolet absorption spectrum (in 0.1 N aqueous sodium bicarbonate solution); $\lambda_{max}$=267 $\mu$ ($\epsilon$=6,200); infra-red absorption spectrum (in mineral oil): characteristic bands, inter alia, at 5.72 $\mu$, 5.94 $\mu$, 6.23 $\mu$ and 6.60 $\mu$.

(b) A mixture of 0.063 g of 7$\beta$-(D-$\alpha$-tert.butoxycarbonylamino-$\alpha$-phenylacetylamino)-3-methoxy-2-cephem-4$\alpha$-carboxylic acid diphenylmethyl ester, 0.1 ml of anisole and 1.5 ml of trifluoroacetic acid is left to stand for 15 minutes at 0° C. and is then concentrated by evaporation under reduced pressure. The residue is digested with diethyl ether, filtered off and dried. The colourless and pulverent trifluoroacetate of 7$\beta$-(D-$\alpha$-phenylglycylamino)-3-methoxy-2-cephem-4$\alpha$-carboxylic acid, thus obtainable, is dissolved in 0.5 ml of water and the pH of the solution is adjusted to a value of about 5 by dropwise addition of a 10% strength solution of triethylamine in methanol. The mixture is stirred for one hour in an icebath and the colourless precipitate is filtered off and dried in a high vacuum. This gives 7β-(D-α-phenylglycylamino)-3-methoxy-2-cephem-4α-carboxylic acid as the inner salt, thin layer chromatogram (silica gel; development with iodine): Rf~0.44 (system: n-butanol/pyridine/acetic acid/water, 40:24:6:30); ultraviolet absorption spectrum (in 0.1 N aqueous sodium bicarbonate solution): $\lambda_{shoulder}=260$ μ.

(c) A solution of 0.20 g of 3-chloro-perbenzoic acid in 5 ml of methylene chloride is added to a solution, cooled to 0° C. of 0.63 g of 7β-(D-α-tert.-butoxycarbonylaminoα-phenylacetylamino)-3-methoxy-2-cephem-4α-carboxylic acid diphenylmethyl ester in 25 ml of methylene chloride. The mixture is stirred for 30 minutes at 0° C., 50 ml of methylene chloride are added and the whole is washed successively with 25 ml of a saturated aqueous sodium bicarbonate solution and 25 ml of a saturated aqueous sodium chloride solution. The organic phase is dried over sodium sulphate and concentrated by evaporation under reduced pressure. The residue is crystallised from a mixture of methylene chloride and diethyl ether; this gives 7β-(D-α-tert.butoxycarbonylamino-α-phenylacetylamino)-3-methoxy-3-cephem-4-carboxylic acid diphenylmethyl ester 1-oxide in the form of colourless needles, melting point 172°–175° C.; thin layer chromatogram (silica gel): Rf~0.44 (system: ethyl acetate; developement with iodine vapour); ultraviolet absorption spectrum (in ethanol): $\lambda_{max}=277$ mμ (ε=7,200); infra-red absorption spectrum (in methylene chloride): characteristic bands at 2.96 μ, 5.56 μ, 5.71 μ, 5.83 μ, 5.90 μ, 6.27 μ and 6.67 μ.

(d) 2.80 g of phosphorus trichloride are added to a solution, cooled to −10° C., of 1.30 g of 7β-(D-α-tert.-butoxycarbonylamino-α-phenylacetylamino)-3-methoxy-3-cephem-4-carboxylic acid diphenylmethyl ester 1-oxide in 30 ml of dimethylformamide, whilst excluding air. After standing for 15 minutes, the reaction mixture is poured out onto a mixture of ice and an aqueous dipotassium hydrogen phosphate solution; the aqueous mixture is extracted with twice 100 ml of ethyl acetate. The organic extract is washed with a saturated aqueous sodium chloride solution, dried over sodium sulphate and evaporated. The residue is chromatographed on silica gel; amorphous 7β-(D-α-tert.-butoxycarbonylamino-α-phenylacetylamino)-3-methoxy-3-cephem-4-carboxylic acid diphenylmethyl ester is eluted with diethyl ether as a substance which is pure according to thin layer chromatography, Rf~0.39 (system: diethyl ether; development with iodine vapour); $[\alpha]_D = 1° \pm 1°$ (c=0.981 in chloroform); ultraviolet absorption spectrum (in ethanol): $\lambda_{max}=264$ μ (ε= 6,300); infra-red absorption spectrum (in methylene chloride): characteristic bands at 2.94 μ, 5.62 μ, 5.84 μ, 5.88 μ, 6.25 μ and 6.70 μ.

The starting material can be obtained as follows:

(e) 16.5 ml (0.12 mmol) of chloroformic acid isobutyl ester are added to a solution, cooled to −15° C., of 31.2 g (0.12 mmol) of D-N-tert.butoxycarbonyl-phenylglycine and 16.7 ml (0.12 mmol) of triethylamine in 300 ml of tetrahydrofurane and the mixture is stirred for 30 minutes at −10° C. A solution of 21.6 g (0.10 mmol) of 6-amino-penicillanic acid and 15.4 ml (0.11 mmol) of triethylamine in 300 ml of tetrahydrofurane/water, 2:1, is then added. The reaction mixture is stirred for 1 hour at 0° C. and 2 hours at room temperature whilst keeping the pH value constant at approx. 6.9 by adding triethylamine. The reaction mixture is adjusted to pH 2.0 at 5° C. by means of phosphoric acid and is saturated with sodium chloride and extracted with three times 500 ml of ethyl acetate; the organic phase is washed with saturated aqueous sodium chloride solution, dried over sodium sulphate and concentrated by evaporation. The crude N-tert.butoxycarbonyl-ampicillin obtained in the form of a light yellow foam has an Rf value of ~0.65 in a thin layer chromatogram (silica gel; ethyl acetate/n-butanol/pyridine/acetic acid/water, 42:21:21:6:10).

(f) 21.6 ml of 30% strength hydrogen peroxide (0.25 M) are added to a solution of 57.22 g of crude N-tert.butoxycarbonyl-ampicillin in 100 ml of glacial acetic acid over the course of 10 minutes and the mixture is stirred for 2.5 hours at room temperature. The reaction mixture is then poured onto 2 l of ice water and the N-tert.butoxycarbonyl-ampicillin 1-oxide obtained in the form of a voluminous precipitate is filtered off, well washed with water and dried in vacuo. A further quantity of crude N-tert.butylcarbonyl-ampicillin 1-oxide can be obtained by extracting the filtrate with ethyl acetate. Thin layer chromatogram (silica gel; ethyl acetate/n-butanol/pyridine/acetic acid/water, 42:21:21:6:10): Rf value ~0.30.

(g) A solution of 42 g (0.23 M) of diphenyldiazomethane in 130 ml of dioxane is added to a mixture of 67.7 g of crude N-tert.butoxycarbonyl-amipicillin 1-oxide in 380 ml of dioxane and the whole is stirred for 2.5 hours at room temperature. After adding 5 ml of glacial acetic acid, the mixture is concentrated by evaporation in vacuo. The residue is digested with petroleum ether, the petroleum ether ectract is discarded and the residue is crystallized from methylene chloride/ether/hexane. N-tert.Butoxycarbonyl-ampicillin 1-oxide diphenylmethyl ester of melting point 164°–166° C. is obtained; $[\alpha]^{20}_d = +117° \pm 1°$ (c=1,CHCl$_3$); IR spectrum (methylene chloride): characteristic bands at 2.91, 2.94, 5.54, 5.69, 5,82 (shoulder), 5.88, 6.60 and 6.68 μ; thin layer chromatogram: Rf value ~0.23 (silica gel; toluene/ethyl acetate, 3:1).

(h) A mixture of 11.2 g (17.7 mmols) of N-tert.-butoxycarbonyl-ampicillin 1-oxide diphenylmethyl ester and 3.26 g (19.5 mmols) of mercaptobenzthiazole in 170 ml of toluene is boiled for 3 hours in a reflux apparatus equipped with a water separator, and is then concentrated by evaporation. The residue is chromatographed on silica gel, using toluene/ethyl acetate, 3:1, as the eluting agent and gives amorphous 2-[4-(benzthiazol-2-ylthio)-3-(α-tert.butoxycarbonylamino-α-phenylacetylamino)-2-oxoazetidin-1-yl]-3-methylenebutyric acid diphenylmethyl ester, thin layer chromatogram: Rf value ~0.37 (silica gel; toluene/ethyl acetate, 3:1); IR spectrum (methylene chloride): characteristic bands at 2.94, 5.64, 5.76, 5.86 (shoulder), 5.91 and 6.71 μ.

(i) 0.868 g (3.46 mmols) of silver toluenesulphinate is added to a solution of 2.34 g (3.0 mmols) of 2-[4-(benzthiazol-2-ylthio)-3-(α-tert.butoxycarbonylamino-α-phenylacetylamino)-2-oxoazetidin-1-yl]-3-methylene-butyric acid diphenylmethyl ester in 30 ml of acetone/water, 9:1, at 0° C., and the mixture is stirred for 1 hour in an icebath. The precipitate which has separated out is filtered off. The filtrate is taken up in toluene and extracted by shaking with saturated aqueous sodium chloride solution. The organic phase is dried over sodium sulphate and, after evaporation, gives amorphous 2-[4-(p-toluenesulphonylthio)-3-(α-tert.butoxycarbonylamino-α-phenylacetylamino)-2-oxoazetidin-1-yl]-3-methylene-butyric acid diphenylmethyl ester; thin layer chromatogram: Rf value ~0.33 (silica gel; toluene-/ethyl acetate, 3:1); IR spectrum (methylene chloride): characteristic bands at 2.93, 5.57, 5.70, 5.82, 6.21 and 6.65 μ.

(j) An ozone/oxygen stream (0.5 mmol per minute) is passed for 7 minutes into a solution, cooled to −70° C., of 2.30 g (3.0 mmols) of 2-[4-(p-toluenesulphonylthio)-3-(α-tert.butoxycarbonylamino-α-phenylacetylamino)-2-oxoazetidin-1-yl]-3-methylene-butyric acid diphenylmethyl ester in 230 ml of methylene chloride. After adding 1 ml of dimethyl sulphide, the solution is stirred for a further hour without cooling and is then concentrated by evaporation in vacuo. The residue is recrystallised from methylene chloride/ether/hexane and gives 2-[4-(p-toluenesulphonylthio)-3-(α-tert.butoxycarbonylamino-α-phenylacetylamino)-2-oxoazetidin-1-yl]-3-hydroxy-crotonic acid diphenylmethyl ester of melting point 182°–184° C.; UV spectrum (ethanol): $\sim_{max}$=259 mμ ($\epsilon$=13,400); IR spectrum (methylene chloride): characteristic bands at 2.92, 5.59, 5.83, 5.92, 6.03 (shoulder), 6.18 and 6.68 μ; thin layer chromatogram: Rf value ~0.55 (silica gel; toluene/ethyl acetate, 1:1).

(k) A solution of 0.54 g (0.7 mmol) of 2-[4-(p-toluenesulphonylthio)-3-(α-tert.butoxycarbonylamino-α-phenylacetylamino)-2-oxoazetidin-1-yl]-3-hydroxy-crotonic acid diphenylmethyl ester in 20 ml of methylene chloride/methanol, 1:1, is stirred for 15 minutes with an excess of a solution of diazomethane in ether at 0° C. and is then concentrated by evaporation in vacuo. Preparative layer chromatography of the residue on silica gel, using toluene/ethyl acetate, 1:1, as the running agent, and elution of the zone which is visible in UV light gives 2-[4-(p-toluenesulphonylthio)-3-(α-tert.butoxycarbonylamino-α-phenylacetylamino)-2-oxoazetidin-1-yl]-3-methoxy-crotonic acid diphenylmethyl ester, which is recrystallised from methylene chloride/diethyl ether/hexane.

Melting point 204°–206° C.; UV spectrum (ethanol): $\lambda_{max}$=259 mμ ($\epsilon$=16,000); IR spectrum (Nujol): characteristic bands at 2.93, 5.58, 5.80, 5.84, 5.93, 6.24 and 6.57 μ; thin layer chromatogram: Rf value ~0.33 (silica gel; toluene/ethyl acetate, 1:1).

EXAMPLE 18

A mixture of 670 mg (1 mmol) of 2-[4-(p-toluenesulphonylthio)-3-phenylacetamido-2-oxoazetidin-1-yl]-3-methoxy-crotonic acid diphenylmethyl ester, 6.7 ml of 1,2-dimethoxyethane and 0.22 ml of 1,5-diazabicyclo[5.4.0]undec-5-ene is stirred for 25 minutes at room temperature under a nitrogen atmosphere. The reaction mixture is diluted with toluene, washed successively with 2 N hydrochloric acid, saturated aqueous sodium bicarbonate solution and saturated aqueous sodium chloride solution, dried over sodium sulphate and concentrated by evaporation in vacuo. The residue, after preparative thick layer chromatography on silica gel using toluene/ethyl acetate, 1:1, gives 7β-phenylacetamido-3-methoxy-ceph-2-em-4α-carboxylic acid diphenylmethyl ester of melting point 166°–169° C. (from methylene chloride/hexane), UV spectrum (ethanol): $\lambda_{max}$ = 258 mμ ($\epsilon$ = 4,500) IR spectrum (methylene chloride): characteristic bands at 2.93, 5.62, 5.73, 5.93 and 6.66 μ, Rf value ~0.54 (silica gel; system toluene/ethyl acetate, 1:1), and amorphous 7β-phenylacetamido-3-methoxy-ceph-3-em-4-carboxylic acid diphenylmethyl ester, UV spectrum (ethanol): $\lambda_{max}$=258 mμ ($\epsilon$=6,350), 264 mμ ($\epsilon$=6,350), 282 mμ ($\epsilon$= 5,600) (shoulder), IR spectrum (methylene chloride): characteristic bands at 2.94, 5.63, 5.83, 5.94, 6.26 and 6.66 μ, Rf value ~0.37 (silica gel; system toluene-/ethyl acetate, 1:1), in the ratio of 8:1.

The material can be processed further as follows:

7β-Phenylacetamido-3-methoxy-ceph-2-em-4α-carboxylic acid diphenylmethyl ester can be converted, analogously to Example 17c), into 7β-phenylacetamido-3-methoxy-ceph-3-em-4-carboxylic acid diphenylmethyl ester 1-oxide of melting point 152–155° C. (from acetone/diethyl ether), Rf value 0.32 (silica gel; system: ethyl acetate), UV spectrum (in 95% strength ethanol): $\lambda_{max}$=288 mμ ($\epsilon$=3,610) and shoulder $\lambda$=247 mμ; IR spectrum (methylene chloride): characteristic bands at 2.94, 5.59, 5.81, 5.95, 6.22 and 6.61 μ.

A purer product, which consists mainly of 7β-phenylacetamido-3-methoxy-ceph-3-em-4-carboxylic acid diphenylmethyl ester 1β-oxide, can be obtained as follows:

A solution of 6.7 g (10 mmols) of 2-[4-(p-toluenesulphonylthio)-3-phenylacetamido-2-oxoazetidin-1-yl]-3-methoxy-isocrotonic acid diphenylmethyl ester in 67 ml of absolute tetrahydrofuran is stirred with 2.28 (15 mmols) of 1,5-diazabicyclo[5.4.0]undec-5-ene for 15 minutes at 20° C., 0.7 ml of glacial acetic acid is added and the mixture is then concentrated by evaporation in vacuo. The oily, dark residue is dissolved in 30 ml of methylene chloride and the solution is successively extracted by shaking with 15 ml of water, 10 ml of 0.5 N hydrochloric acid, 10 ml of saturated aqueous sodium bicarbonate solution and 10 ml of water. The aqueous phases are re-extracted with 10 ml of methylene chloride and the organic extracts are combined and stirred with 2.24 ml of 40% strength peracetic acid for 15 minutes at 0° C. in an icebath. A solution of 1.50 g (6 mmols) of sodium thiosulphate pentahydrate in 20 ml of water is then added to the reaction mixture, the whole is stirred for 10 minutes and the aqueous phase is separated off. The organic phase is additionally washed with 10 ml of water, dried over sodium sulphate and concentrated by evaporation in vacuo. Crystallisation of the solid residue from methylene chloride/petroleum ether gives 7β-phenylacetamido-3-methoxy-ceph-3-em-4-carboxylic acid diphenylmethyl ester 1β-oxide of melting point 175–176° C.; thin layer chromatogram (silica gel): Rf value ~0.1 (toluene/ethyl acetate, 1:1), UV spectrum (ethanol): $\lambda_{max}$=279 mμ ($\epsilon$=7,300); IR spectrum (methylene chloride): characteristic bands at 2.94; 5.56; 5.78; 5.91; 6.20 and 6.67 μ.

7β-Phenylacetamido-3-methoxy-ceph-3-em-carboxylic acid diphenylmethyl ester can be obtained from the 1-oxides analogously to Example 17(e).

From this ester, crude 7β-phenylacetamido-3-methoxy-ceph-3-em-4-carboxylic acid can be obtained by saponification analogously to Example 17(a) can be purified by chromatography on silica gel (containing 5% of water) using methylene chloride containing 30–50% of acetone, followed by lyophilisation from dioxane; UV spectrum (in 95% strength ethanol): $\lambda_{max}$ = 265 mμ ($\epsilon$ = 5,800); IR spectrum (methylene chloride): characteristic bands at 3.03, 5.60, 5.74, 5.92, 6.24 and 6.67 μ.

The starting material and the intermediate products can be prepared as follows:

(a) 19.4 ml of 40 percent strength peractic acid are added over the course of 40 minutes to a mixture of 37.24 g (0.1 mol) of the potassium salt of pencillin G in 90 ml of water, 7.3 ml of acetone and 150 ml of chloroform whilst stirring at 0° C. After a further 15 minutes, 28 g (0.15 mol) of benzophenone-hydrazone are added in portions at the same temperature, followed by 6.3 ml of 1 percent strength aqueous potassium iodide solution and then followed by a mixture of 32.5 ml of 10 percent strength sulphuric acid and 28 ml of 40 percent strength peracetic acid, added dropwise over the course of 1.5 hours. After completion of the addition, the mixture is stirred for a further 30 minutes at 0° C., warmed to 15° C. and diluted with 400 ml of chloroform. The aqueous phase is separated off and the organic phase is successively washed with 300 ml of 5 percent strength aqueous sodium bisulphite solution, 300 ml of saturated aqueous sodium bicarbonate solution and 300 ml of saturated aqueous sodium chloride solution, dried over sodium sulphate and concentrated by evaporation in vacuo. The evaporation residue is recrystallised from ethyl acetate/petroleum ether and gives 6-phenylacetamidopenicillanic acid diphenylmethyl ester 1β-oxide, melting point 139° C.; thin layer chromatogram (silica gel): Rf value ~0.40 (system toluene/ethyl acetate, 1:1), IR spectrum (methylene chloride): characteristic bands at 2.94, 5.56, 5.70, 5.92 and 6.57 $\mu$.

(b) 1.83 g (11 mmols) of 2-mercaptobenzthiazole are added to a mixture of 5.165 g (10 mmols) of 6-phenylacetamidopenicillanic acid diphenylmethyl ester 1β-oxide in 50 ml of toluene and 0.5 ml of glacial acetic acid and the mixture is boiled for 2 hours in a reflux apparatus provided with a water separator. On cooling, 2-[4-(benzthiazol-2-yldithio)-3-phenylacetamido-2-oxoazetidin-1-yl]-3-methylene-butyric acid diphenylmethyl ester crystallises out spontaneously. After recrystallising it once from methylene chloride/diethyl ether, crystals of melting point 134°–136° C. are obtained; thin layer chromatogram (silica gel): Rf value ~0.52 (system toluene/ethyl acetate, 1:1), UV spectrum (ethanol): $\mu_{max}$=269 m$\mu$ ($\epsilon$=12,700); IR spectrum (methylene chloride): characteristic bands at 2.90, 5.60, 5.72, 5.92 and 6.61 $\mu$.

(c) The product obtained under (b) does not have to be isolated for further conversion. After cooling, the reaction mixture can be diluted directly with 30 ml of toluene, after which it is mixed with 3.95 g (15 mmols) of silver p-toluenesulphinate and stirred for 2 hours at room temperature. The yellow precipitate which has separated out is filtered off through Hyflo and rinsed with toluene. The filtrate is extracted by shaking with saturated aqueous sodium chloride solution, dried over sodium sulphate and concentrated by evaporation in vacuo. The evaporation residue is taken up in toluene and petroleum ether is added. The precipitate is filtered off and recrystallised from ethyl acetate/petroleum ether. The resulting 2-[4-(p-toluenesulphonylthio)-3-phenylacetamido-2-oxoazetidin-1-yl]-3-methylenebutyric acid diphenylmethyl ester has a melting point of 75° C.; thin layer chromatogram (silica gel): Rf value ~0.47 (system toluene/ethyl acetate, 1:1), UV spectrum (ethanol): $\lambda_{max}$=259 m$\mu$ ($\epsilon$=4,300); IR spectrum (methylene chloride): characteristic bands at 2.92, 5.62, 5.74, 5.94 and 6.63 $\mu$.

(d) A solution of 655 mg (1 mM) of 2-[4-(p-toluenesulphonylthio)-3-phenylacetamido-2-oxoazetidin-1-yl]-3-methylenebutyric acid diphenylmethyl ester in 65 ml of methylene chloride is treated with an ozone/oxygen mixture at −65° C. until a slight blue colouration results. After addition of 0.5 ml of dimethyl sulphide, the mixture is allowed to warm up to room temperature and is then concentrated by evaporation in vacuo. The resulting crude 2-[4-(p-toluenesulphonylthio)-3-phenylacetamido-2-oxoazetidin-1-yl]-3-hydroxy-crotonic acid diphenylmethyl ester, Rf value ~0.46 (silica gel; system toluene/ethyl acetate, 1:1), IR spectrum (methylene chloride): characteristic bands at 2.95, 5.60, 5.98, 6.18 and 6.61 $\mu$, can be converted further without additional purification (e) The crude product obtained under (d) is dissolved in 20 ml of methanol and a solution of diazomethane in ether is added at 0° C. until a yellow colouration persists. After evaporating off the solvent in vacuo, the residue is purified by preparative thick layer chromatography on silica gel, using toluene/ethyl acetate, 1:1, as the running agent. 2-[4-(p-Toluenesulphonylthio)-3-phenylacetamido-2-oxoazetidin-1-yl]-3-methoxy-crotonic acid diphenylmethyl ester, Rf value ~0.2 (silica gel; system toluene/ethyl acetate, 1:1), IR spectrum (methylene chloride): characteristic bands at 2.94, 5.61, 5.96, 6.24 and 6.62 $\mu$, is obtained alongside a little 2-[4-(p-toluenesulphonylthio)-3-phenylacetamido-2-oxoazetidin-1-yl]-3-methoxy-isocrotonic acid diphenylmethyl ester.

EXAMPLE 19

5.20 ml (35 mmols) of 1,5-diazabicyclo[5.4.0]undec-5-ene are added to a solution of 6.06 g (10 mmols) of a 3:1 mixture of the isomeric 2-[4-(p-toluenesulphonylthio)-3-phenoxyacetamido-2-oxoazetidin-1-yl]-3-methoxycrotonic acid benzyl ester and 2-[4-(p-toluenesulphonylthio)-3-phenoxyacetamido-2-oxoazetidin-1-yl]-3-methoxy-isocrotonic acid benzyl ester and 2.33 g (15 mmols) of p-toluenesulphinc acid in 200 ml of absolute tetrahydrofurane at room temperature, whilst stirring. The mixture is stirred for a further 40 minutes at room temperature, mixed with 500 ml of methylene chloride and washed successively with 200 ml of 0.5 N hydrochloric acid, 200 ml of water, 200 ml of 0.5 N sodium bicarbonate and 200 ml of water. The methylene chloride phase is dried over sodium sulphate and concentrated by evaporation in vacuo. The residue is chromatographed on 200 g of acid-washed silica gel, using toluene/ethyl acetate, 3:1, and 7β-phenoxyacetamido-3-methoxy-ceph-2-em-4α-carboxylic acid benzyl ester of melting point 148°–151° C. is obtained by adding diethyl ether to the fractions. IR spectrum (methylene chloride): characteristic bands at 5.60, 5.75, 5.90, and 8.25 $\mu$; $[\alpha]_D^{20}$ = +284°±1° (c=1; chloroform).

Toluene/ethyl acetate, 2:1, elutes 7β-phenoxyacetamido-3-methoxy-ceph-3-em-4-carboxylic acid benzyl ester, which can also be precipitated with diethyl ether, and has a melting point of 89°–91° C.; IR spectrum (methylene chloride): characteristic bands at 5.60, 5.85 and 5.90; $[\alpha]_D^{20}$ = +47°±1° (c=1; chloroform).

The ratio of the ceph-2-em compound of the ceph-3-em compund is about 3:1.

The compounds can be further converted as follows:

15 ml of pre-cooled 0.1 N potassium hydroxide solution are added, whilst stirring, to a solution prepared at 0° C., of 454 mg (1 mmol) of an approx. 3:1 mixture of 7β-phenoxyacetamido-3-methoxy-ceph-2-em-4α-carboxylic acid benzyl ester and 7β-phenoxyacetamido-3-methoxy-ceph-3-em-4-carboxylic acid benzyl ester in 30 ml of tetrahydrofurane. The mixture is stirred for a further 5 minutes at 0° C., 100 of ice water and 100 ml of pre-cooled methylene chloride are then added and the whole is stirred vigorously. Addition of a little saturated aqueous sodium chloride solution causes the mixture to separate into two phases. The methylene chloride phase is separated off and the aqueous phase is washed with a further 30 ml of methylene chloride. The aqueous phase is covered with 50 ml of methylene chloride, 10 ml of 2 N hydrochloric acid are added and the mixture is thoroughly shaken. After separating off the organic phase, the aqueous phase is extracted twice more with 30 ml of methylene chloride at a time. The combined methylene chloride extracts are dried over sodium sulphate and concentrated by evaporation in vacuo. The resulting white foam crystallises on addition of chloroform and diethyl ether and gives 7β-phenoxyacetamido-3-methoxy-ceph-2-em-4α-carboxylic acid of melting point 142° C. (decomposition). IR spectrum (KBr): characteristic bands at 5.65, 5.75 and 5.95 μ.

The starting material can be prepared as follows:

(a) 20 ml (14.6 g, 0.145 mol) of triethylamine and 17 ml (24.5 g, 0.143 mol) of benzyl bromide are added to a solution of 36.6 g (0.1 mol) of 6-phenoxyacetamido-penicillanic acid 1β-oxide in 150 ml of dry dimethylformamide whilst cooling with tap water. The mixture is stirred for 20 hours at room temperature and is then poured onto ice water. The precipitate is filtered off, washed with approx. 1,000 ml of water, dried for 2 days in vacuo at 40° C., then taken up in 200 ml of methylene chloride and again dried with sodium sulphate. The white foam which remains after evaporating off the solvent in vacuo is dissolved in 150 ml of ethyl acetate and the solution is left to stand first at room temperature and then at −20° C., whereupon pure 6-phenoxyacetamido-penicillanic acid benzyl ester 1β-oxide crystallises. Melting point 139°–140° C.; IR spectrum (methylene chloride); characteristic bands at 5.55, 5.75 and 5.90 μ; $[\alpha]_D^{20} = +174° \pm 1°$ (c=1, chloroform).

Further quantities of the crystalline benzyl ester 1β-oxide can be obtained from the mother liquor by chromatography on 250 g of acid-washed silica gel, using toluene/ethyl acetate (1 : 1).

(b) 4.56 g (10 mmols) of 6-phenoxyacetamido-penicillanic acid benzyl ester 1β-oxide and 1.84 g (11 mmols) of 2-mercaptobenzthiazole in 100 ml of toluene are heated for 5 hours under reflux (bath temperature 135° C.). The mixture is left to stand, whereupon 2-[4-(benzthiazol-2-yldithio)-3-phenoxyacetamido-2-oxoazetidin-1-yl]-3-methylene-butyric acid benzyl ester crystallises out. The crystals are filtered off, washed with 50 ml of toluene and dried in a high vacuum. Further quantities of the crystalline product can be obtained by chromatography of the mother liquor on 70 g of acid-washed silica gel, using toluene/ethyl acetate (3:1). Melting point of the pure product 150°~153° C.; IR spectrum (methylene chloride): characteristic bands at 5.60, 5.75 and 5.90 μ; $[\alpha]_D^{20} = -112° \pm 1°$ (c=1; chloroform).

(c) An oxygen/ozone mixture is passed through a solution of 6.06 g (10 mmols) of 2-[4-(benzthiazol-2-yldithio)-3-phenoxy-acetamido-2-oxoazetidin-1-yl]-3-methylene-butyric acid benzyl ester in 300 ml of methylene chloride at −20° C. until the starting material has been completely ozonised (as checked by means of thin layer chromatography on silica gel, using toluene/ethyl acetate, 1:1). 50 ml of 10% strength aqueous sodium bisulphite solution are then added to the mixture which is stirred until (after 5 minutes) ozonide is no longer detectable with potassium iodide/starch. 300 ml of water are added to the mixture and the product is partitioned between the two phases produced. The organic phase is dried over sodium sulphate and freed from the solvent. The residue is triturated in 100 ml of ether-pentane (1:1) at 0° C., whereupon 2-[4-(benzthiazol-2-yldithio)-3-phenoxyacetamido-2-oxoazetidin-1-yl]-3-hydroxy-crotonic acid benzyl ester melting point 58°–62° C., crystallises out; IR spectrum (methylene chloride): characteristic bands at 5.60, 5.90 and 6.00 μ; $[\alpha]_D^{20} = -92° \pm 1°$ (c=1, chloroform).

(d) 6.08 g (0.01 mol) of 2-[4-(benzthiazol-2-yldithio)-3-phenoxyacetamido-2-oxoazetidin-1-yl]-3-hydroxy-crotonic acid benzyl ester and 3.50 g (0.013 mol) of silver p-toluenesulphinate are stirred in 200 ml of acetone-water (9:1) for 60 minutes at room temperature. The yellow precipitate formed is filtered off through Cellit, the residue is washed with acetone and the filtrate is concentrated in vacuo to a volume of approx. 20 ml. The product is then partitioned between methylene chloride and dilute aqueous sodium sulphate solution. The organic phase is dried over sodium sulphate and the solvent is evaporated in vacuo. The residue is taken up in 70 ml of ethyl acetate, if necessary with warming, freed from a little insoluble matter by filtration and again concentrated by evaporation. On addition of 100 ml of ether-pentane at 0° C., 2-[4-(p-toluenesulphonylthio)-3-phenoxyacetamido-2-oxoazetidin-1-yl]-3-hydroxy-crotonic acid benzyl ester of melting point 151°–152° C. crystallises out; IR spectrum (methylene chloride): characteristic bands at 5.60, 5.90, 6.00 and 8.75 μ; $[\alpha]_D^{20} = -16° \pm 1°$ (c=1; chloroform).

(e) A solution of diazomethane in ether is added dropwise to a solution of 5.97 g (0.01 mol) of pure 2-[4-(p-toluenesulphonylthio)-3-phenoxyacetamido-2-oxoazetidin-1-yl]-3-hydroxy-crotonic acid benzyl ester in 50 ml of methylene chloride at 0° C., whilst stirring, until the starting material has been completely methylated (checked by thin layer chromatography on silica gel, using toluene/ethyl acetate, 1:1). Excess diazomethane is neutralised by a few drops of glacial acetic acid (but an excess of glacial acetic acid should be avoided) after which the mixture is concentrated by evaporation in vacuo. The yellowish, foam-like residue is crystallised from diethyl ether/pentane (1:1), giving an isomer mixture consisting of 2-[4-(p-toluenesulphonylthio)-3-phenoxyacetamido-2-oxoazetidin-1-yl]-3-methoxy-crotonic acid benzyl ester and 2-[4-(p-toluenesulphonylthio)-3-phenoxyacetamido-2-oxoazetidin-1-yl]-3-methoxy-isocrotonic acid benzyl ester in the ratio of about 3:1.

The two isomers can be separated by repeated chromatography on silica gel, using toluene/ethyl acetate, 1:1. The resulting 2-[4-(p-toluenesulphonylthio)-3-phenoxyacetamido-2-oxoazetidin-1-yl]-3-methoxy-crotonic acid benzyl ester has a melting point of 166°–168° C.; $[\alpha]_D^{20} = -36° \pm -1°$ (c=1; chloroform); IR spectrum (methylene chloride): characteristic bands at 5.60, 5.80, 5.90 and 8.72 μ; NMR spectrum (chloroform): characteristic bands at 2.12 (s); 5.00 (dd); 5.90 (d) ppm; thin layer chromatogram: Rf value~0.10 (silica gel; toluene/ethyl acetate, 1:1). The resulting 2-[4-(p-toluenesulphonylthio)-3-phenoxyacetamido-2-oxoazetidin-1-yl]-3-methoxy-iso-crotonic acid benzyl ester has a melting point of 59°–63° C.; $[\alpha]_D^{20} = -1° \pm 1°$ (c=1; chloroform); IR spectrum (methylene chloride): characteristic bands at 5.60, 5.87 sh. 5.90 and 8.72 μ; NMR spectrum (chloroform): characteristic bands at 3.23 (s), 5.45 (d,d), 5.73 (d) ppm; thin layer chromatogram: Rf value~0.13 (silica gel; toluene/ethyl acetate, 1:1).

EXAMPLE 20

302 mg (2 mmols) of 1,5-diazabicyclo[5.4.0]undec-5-ene are added to a solution of 534 mg (1 mmol) of a mixture consisting of 2-[4-(p-toluenesulphonylthio)-3-phenoxyacetamido-2-oxoazetidin-1-yl)-3-methoxy-isocrotonic acid methyl ester and 2-[4-(p-toluenesulphonylthio)-3-phenoxyacetamido-2-oxoazetidin-1-yl)-3-methoxy-crotonic acid methyl ester in the ratio of about 4:1, in 20 ml of tetrahydrofurane, whilst stirring. The mixture is then stirred for 40 minutes, diluted with 70 ml of methylene chloride and washed successively with dilute hydrochloric acid, with water, with dilute aqueous sodium bicarbonate solution and again with water. The organic phase is dried over sodium sulphate and concentrated by evaporation in vacuo. The residue is chromatographed on 15 g of acid-washed silica gel using toluene/ethyl acetate, 2:1 followed by 1:1, resulting in the elution of, first, pure 7β-phenoxyacetamido-3-methoxy-ceph-2-em-4α-carboxylic acid methyl ester, IR spectrum (in methylene chloride): characteristic bands at 5.60, 5.70, 5.90 and 8.25 $\mu$, followed by pure 7β-phenoxyacetamido-3-methoxy-ceph-3-em-4-carboxylic acid methyl ester, IR spectrum (in methylene chloride): characteristic bands at 5.60, 5.85, 5.90 and 7.10 $\mu$, in the form of colourless foams.

The compounds obtained can be further converted as follows:

15 ml of cooled 0.1 N aqueous potassium hydroxide solution are added, whilst stirring, to a solution, cooled in an ice bath, of 382 mg of 7β-phenoxyacetamido-3-methoxy-ceph-2-em-4α-carboxylic acid methyl ester in 30 ml of tetrahydrofurane. After 5 minutes, 100 ml of water and 70 ml of methylene chloride are added and the mixture is acidified by adding 10 ml of 1 N aqueous hydrochloric acid. The methylene chloride phase is separated off and the aqueous phase is extracted with 30 ml of methylene chloride. The combined organic phases are dried over sodium sulphate and concentrated by evaporation in vacuo. The residue is crystallised from chloroform/diethyl ether and gives 7β-phenoxyacetamido-3-methoxy-ceph-2-em-4α-carboxylic acid of melting point 142° C. (decomposition).

The same compound, of melting point 142° C. (decomposition) is obtained when 7β-phenoxyacetamido-3-methoxy-ceph-3-em-4-carboxylic acid methyl ester is saponified with 0.1 N potassium hydroxide solution, as described earlier.

The starting materials can be prepared as follows:

(a) A solution of 19.25 g (50 mmols) of 6-phenoxyacetamido-penicillanic acid methyl ester 1β-oxide and 9.4 g (55 mmols) of 2-mercaptobenzthiazole in 500 ml of dry toluene is boiled for 8 hours under reflux and then concentrated in vacuo. The residue is dissolved in 400 ml of ethyl acetate whilst warming ($\sim$80° C.) and the solution is treated with 0.2 g of active charcoal and filtered through an electrically heated glass frit. On cooling, 2-[4-(benzthiazol-2-yldithio)-3-phenoxyacetamido-2-oxoazetidin-1-yl]-3-methylene-butyric acid methyl ester of melting point 132°$\sim$134° C. separates out. Further quantities of this compound (melting point 135°$\sim$137° C.) can be obtained from the mother liquors.

(b) An ozone/oxygen mixture is passed through a solution of 20.6 g (40 mmols) of 2-[4-(benzthiazol-2-yldithio)-3-phenoxyacetamido-2-oxoazetidin-1-yl]-3-methylene-butyric acid methyl ester in 400 ml of acetone at −20° C. until no further starting material is detectable by thin layer chromatography (silica gel, toluene/ethyl acetate, 1:1). 40 ml of dimethylsulphide are then added to the mixture and the whole is stirred for 3 days at room temperature until ozone is no longer detectable with potassium iodide/starch. The mixture is concentrated by evaporation in vacuo and the liquid residue is poured onto 400 ml of ice water. The precipitate is filtered off, washed with 200 ml of ice water, dried in vacuo and crystallised from diethyl ether/pentane at 0° C. The resulting 2-[4-(benzthiazol-2-yldithio)-3-phenoxyacetamido-2-oxoazetidin-1-yl]-3-hydroxycrotonic acid methyl ester has a melting point of 127°$\sim$130° C; IR spectrum (in methylene chloride): characteristic bands at 5.60, 5.90, 6.00 and 8.10 $\mu$. Further quantities of the product can be obtained by chromatography of the mother liquors on silica gel, using toluene/ethyl acetate, 3:1.

(c) Sufficient of a solution of diazomethane in ether is added to a solution of 4.85 g (0.01 mol) of 2-[4-(benzthiazol-2-yldithio)-3-phenoxyacetamido-2-oxoazetidin-1-yl]-3-hydroxycrotonic acid methyl ester in 50 ml of methylene chloride at 0° C., whilst stirring, that after periods of stirring of 15 minutes starting material is in each case no longer detectable by thin layer chromatography (silica gel, toluene/ethyl acetate, 1:1). Excess diazomethane is neutralised with a minimum amount of acetic acid and the mixture is concentrated by evaporation in vacuo. The residue consists of a mixture of 2-[4-(benzthiazol-2-yldithio)-3-phenoxyacetamido-2-oxoazetidin-1-yl]-3-methoxy-isocrotonic acid methyl ester and 2-[4-(benzthiazol-2-yldithio)-3-phenoxyacetamido-2-oxoazetidin-1-yl]-3-methoxy-crotonic acid methyl ester in the ratio of about 4:1. IR spectrum (in methylene chloride): characteristic bands at 5.60, 5.85, 5.90, 9.05 and 10.00 $\mu$.

(d) A mixture comprising 5.03 g (0.01 mol) of a mixture of 2-[4-(benzthiazol-2-yldithio)-3-phenoxyacetamido-2-oxoazetidin-1-yl]-3-methoxy-isocrotonic acid methyl ester and the corresponding crotonic acid methyl ester in the ratio of about 4:1, 3.50 g (0.013 mol) of silver p-toluenesulphinate and 200 ml of acetone/water, 9:1, is stirred for 40 minutes at room temperature and then filtered through Cellit. The filter residue is washed with acetone and the combined filtrates are concentrated in vacuo to a volume of about 20 ml. After adding 100 ml of methylene chloride and 100 ml of dilute aqueous sodium sulphate solution, the whole is shaken thoroughly, the aqueous phase is separated off and the methylene chloride phase is dried over sodium sulphate and concentrated by evaporation in vacuo. The residue is purified by trituration with diethyl ether/pentane at 0° C. and is filtered off. A mixture of 2-[4-(p-toluenesulphonylthio)-3-phenoxy-acetamido-2-oxoazetidin-1-yl]-3-methoxy-isocrotonic acid methyl ester and 2-[4-(p-toluenesulphonylthio)-3-phenoxyacetamido-2-oxoazetidin-1-yl]-3-methoxy-crotonic acid methyl ester in the ratio of about 4:1 is obtained in the form of a white powder. IR spectrum (in methylene chloride) characteristic bands at 5.60, 5.85, 5.90 and 8.75 $\mu$.

EXAMPLE 21

A solution of 731 mg (1 mmol) of a 1:1 mixture consisting of 2-[4-(p-toluenesulphonylthio)-3-phenoxyacetamido-2-oxoazetidin-1-yl]-3-benzoxy-crotonic acid p-nitrobenzyl ester and the corresponding isocrotonic acid p-nitrobenzyl ester in a mixture of 0.185 ml (1.2 mmols) of 1,5-diazabicyclo[5.4.0] undec-5-ene in 20 ml of dry tetrahydrofurane is stirred for precisely 35 minutes at room temperature. 50 ml of methylene chloride are added to the mixture and the whole is washed successively with dilute hydrochloric acid, water and dilute aqueous sodium bicarbonate solution. The organic phase is dried over sodium sulphate and concentrated by evaporation in vacuo. The residue is chromatographed on 25 mg of acid-washed silica gel, using toluene/ethyl acetate (3:1). A mixture consisting of the ceph-2-em compound and the ceph-3-em compound in the ratio of about 3:1 is obtained; this mixture can be separated by repeated chromatography into the pure isomers, giving 7β-phenoxyacetamido-3-benzoxy-ceph-2-em-4α-carboxylic acid p-nitrobenzyl ester of melting point 160° C.-162° C. (diethyl ether/pentane); IR spectrum (methylene chloride): characteristic bands at 5.6, 5.7, 5.9 and 7.4 μ, and 7β-phenoxyacetamido-3-benzoxy-ceph-3-em-4-carboxylic acid p-nitrobenzyl ester in the form of a colourless foam, IR spectrum (methylene chloride): characteristic bands at 5.6, 5.8 sh, 5.9, 7.9 and 8.4 μ.

The isomer mixture obtained can be further converted as follows:

The isomer mixture obtained, consisting of 7β-phenoxyacetamido-3-benzoxy-ceph-2-em-4α-carboxylic acid p-nitrobenzyl ester and 7β-phenoxyacetamido-3-benzoxy-ceph-3-em-4-carboxylic acid p-nitrobenzyl ester in the ratio of about 3:1, is dissolved in 8 ml of trifluoroacetic acid and the solution is stirred for 90 minutes at room temperature. The reaction mixture is then concentrated by evaporation in vacuo and residual trifluoroacetic acid is repeatedly driven off with toluene. The residue is chromatographed on 20 g of acid-washed silica gel, using toluene/ethyl acetate (3:1), giving 7β-phenoxyacetamido-3-hydroxy-ceph-3-em-4-carboxylic acid p-nitrobenzyl ester in the form of a colourless foam. IR spectrum (methylene chloride): characteristic bands at 2.95, 3.3, 5.6, 5.75 sh, 5.9, 5.95 sh, 6.55, 7.45, 8.15 and 8.3 μ; NMR spectrum (deuterochloroform): characteristic bands at 3.4 (2H, AB q, J=17 Hz), 4.57 (2H, s), 5.06 (1H, d, J=5 Hz), 5.35 (2H, AB q, J=14 Hz), 5.7 (1H, dd, J=5, 10 Hz), 6.8–8.4 (10H, c), 11.4 (1H, br.s.) ppm.

The starting material can be prepared as follows:

30 ml of the solution prepared "in situ" (from N-benzyl-N-nitrotoluenesulphonamide) of 1.2 g (approx. 10 mmols) of phenyldiazomethane in ether is added, at room temperature, to a solution of 1.282 g (2 mmols) of 2-[4-(p-toluenesulfonylthio)-3-phenoxyacetamido-2-oxoazetidin-1-yl]-3-hydroxycrotonic acid p-nitrobenzyl ester in 4 ml of distilled dioxane. The mixture is boiled for 6 hours under reflux at 45° C. bath temperature, diluted with 100 ml of methylene chloride and then washed with 100 ml of water. The organic phase is dried over sodium sulphate, concentrated by evaporation in vacuo and dried in a high vacuum. The resulting yellow oil is chromatographed on 100 g of acid-washed silica gel, using toluene/ethyl acetate, 3:1 and 2:1, as the running agents. An isomer mixture consisting of 2-[4-(p-toluenesulphonylthio)-3-phenoxyacetamido-2-oxoazetidin-1-yl]-3-benzoxy-crotonic acid p-nitrobenzyl ester and 2-[4-(p-toluenesulphonylthio)-3-phenoxyacetamido-2-oxoazetidin-1-yl]-3-benzoxy-isocrotonic acid p-nitrobenzyl ester in the ratio of about 1:1 is obtained; this can be separated into the individual isomers by repeated chromatography, as described earlier. IR spectrum of the faster-running crotonic acid derivative (methylene chloride): characteristic bands at 5.6, 5.80, 5.90 and 8.75 μ; NMR spectrum (deuterochloroform): characteristic bands at 2.2 (s), 5.05 (dd), 5.93 (d) ppm; thin layer chromatogram: Rf value ~0.3 (silica gel; toluene/ethyl acetate, 2:1); IR spectrum of the slower-running isocrotonic acid derivative (methylene chloride): characteristic bands at 5.6, 5.85 sh, 5.90 and 8.75 μ; NMR spectrum (deuterochloroform): characteristic bands at 2.5 (s), 5.41 (dd), 5.77 (d) ppm; thin layer chromatogram: Rf value~0.25 (silica gel; toluene/ethyl acetate, 2:1).

EXAMPLE 22

405 mg (0.5 mmol) of an isomer mixture consisting of 2-[4-(p-toluenesulphonylthio)-3-phenoxyacetamido-2-oxoazetidin-1-yl)[-3-diphenylmethoxy-crotonic acid p-nitrobenzyl ester and the corresponding isomeric isocrotonic acid ester are dissolved in 8 ml of dry detrahydrofurane containing 0.9 ml (0.6 mmol) of 1,5-diazabicyclo[5.4.0]undec-1-ene and the solution is stirred for precisely 45 minutes at room temperature. The yellow reaction mixture is then diluted with 25 ml of methylene chloride and washed with 0.5 N hydrochloric acid, water and dilute aqueous sodium bicarbonate solution. The organic phase is dried over sodium sulphate and concentrated by evaporation.

An isomer mixture consisting of 7β-phenoxyacetamido-3-diphenylmethoxy-ceph-2-em-4α-carboxylic acid p-nitrobenzyl ester and 7β-phenoxyacetamido-3-diphenylmethoxy-ceph-3-em-4-carboxylic acid p-nitrobenzyl ester is obtained; IR spectrum (methylene chloride): characteristic bands at 5.60, 5.70, 5.90, 6.55 and 7.40 μ.

The resulting isomer mixture of the two compounds can be further converted as follows:

A solution of 340 mg of the resulting isomer mixture, consisting of 7β-phenoxyacetamido-3-diphenylmethoxy-ceph-2-em-4α-carboxylic acid p-nitrobenzyl ester and 7β-phenoxyacetamido-3-diphenylmethoxy-ceph-3-em-4-carboxylic acid p-nitrobenzyl ester, in a mixture of 0.5 m. of trifluoroacetic acid and 9.5 ml of methylene chloride is stirred for 40 minutes at room temperature. The mixture is concentrated by evaporation in vacuo, toluene is added to the residue, and the mixture is again concentrated by evaporation. The resulting residue (which still contains trifluoroacetic acid) is chromatographed on 15 g of acid-washed silica gel, using toluene-/ethyl acetate (3:1), whereby 7β-phenoxyacetamido-3-hydroxy-ceph-3-em-4-carboxylic acid p-nitrobenzyl ester is obtained; IR spectrum (methylene chloride): characteristic bands at 2.95, 3.3, 5,6, 5.75 sh, 5.9, 5.95 sh, 6.55, 7.45, 8.15 and 8.3 μ; NMR spectrum (deuterochloroform): characteristic bands at 3.4 (2H, AB q, ]=17 Hz), 4.57 (2H, s), 5.06 (1H, d,]=5 Hz), 5.35 (2Y, AB q,]=14 Hz), 5.7 (1H, dd,]=5, 10 Hz), 6.8–8.4 (10 H, c), 11.4 (1H, br. s.) ppm.

The starting material can be obtained as follows:

A solution of 350 mg (1.75 mmols) of diphenyldiazomethane in 0.3 ml of dioxane is added to a solution of 641 mg (1 mmol) of 2-[4-(p-toluenesulphonylthio)-3-phenoxyacetamido-2-oxoazetidin-1-yl]-3-hydroxy-crotonic acid p-nitrobenzyl ester in 0.5 ml of distilled dioxane and the reaction mixture is warmed to 50° C. for 36 hours, without stirring. The mixture is concentrated by evaporation in vacuo, the dioxane which remains is driven off by adding toluene and again concentrating by evaporation, and the residue is chromatographed on 20 g of acid-washed silica gel, using toluene/ethyl acetate (7:1) and (3:1).

An isomer mixture consisting of 2-[4-(p-toluenesulphonylthio)-3-phenoxyacetamido-2-oxoazetidin-1-yl]-3-di-phenylmethoxy-crotonic acid p-nitrobenzyl ester and 2-[4-(p-toluenesulphonylthio)-3-phenoxyacetamido-2- oxoazetidin-1-yl]-3-diphenylmethoxy-isocrotonic acid p-nitrobenzyl ester is obtained, IR spectrum (methylene chloride): characteristic bands at 5.6, 5.85 sh, 5.9, 6.25, 6.55, 7.43 and 8.75 μ.

EXAMPLE 23

800 mg (5.25 mmols) of 1,5-diazabicyclo[5.4.0]undec-5-ene are added to a solution of 933 mg (1.5 mmols) of an isomer mixture consisting of 2-[4-benzthiazol-2-yldithio)-3-phenoxyacetamido-2-oxoazetidin-1-yl]-3-benzoxy-crotonic acid methyl ester and the corresponding isocrotonic acid methyl ester, in the ratio of about 1:1, and 350 mg (2.25 mmols) of p-toluenesulphinic acid in 30 ml of dry tetrahydrofurane, and the reaction mixture is stirred for precisely 40 minutes at room temperature. It is then diluted with 100 ml of benzene and washed with dilute aqueous hydrochloric acid, with water, with dilute aqueous sodium hydroxide solution and again with water. The benzene phase is dried over sodium sulphate and concentrated by evaporation in vacuo. Chromatography using toluene/ethyl acetate (5:1) on silica gel gives an isomer mixture consisting of 7β-phenoxyacetamido-3-benzoxy-ceph-3-em-4-carboxylic acid methyl ester and 7β-phenoxyacetamido-3-benzoxy-ceph-2-em-4-carboxylic acid methyl ester: IR spectrum (methylene chloride): characteristic bands at 5.60, 5.72, 5.85 sh and 5.90 μ.

The starting material can be prepared as follows:

960 mg (approx. 8 mmols) of freshly distilled phenyldiazomethane are added to a solution of 483 mg (1 mmol) of 2-[4-benzthiazol-2-yldithio)-3-phenoxyacetamido-2-oxoazetidin-1-yl]-3-hydroxy-crotonic acid methyl ester in 1.5 ml of methylene chloride/diethyl ether and the reaction mixture is stirred for 20 hours at 0° C., then diluted with methylene chloride and washed with water. The organic phase is dried over sodium sulphate and concentrated by evaporation in vacuo. The residue is dried in a high vacuum and then chromatographed on 10 g of acid-washed silica gel, using toluene/ethyl acetate (2:1), giving an isomer mixture consisting of 2-[4-(benzthiazol-2-yldithio)-3-phenoxyacetamido-2-oxoazetidin-1-yl]-3-benzoxycrotonic acid methyl ester and the corresponding isocrotonic acid methyl ester in the ratio of about 1:1; IR spectrum (methylene chloride): characteristic bands at 5.6, 5.85 sh, 5.9 and 9.9 μ.

EXAMPLE 24

Analogously to Example 5 d, reaction of 1.16 g (3 mmols) of 7β-amino-3-methoxy-ceph-3-em-4-carboxylic acid hydrochloride dioxanate, obtainable according to the invention, with 1.5 ml (6.2 mmols) of bis-(trimethylsilyl)-acetamide and subsequently with (a) 765 mg (3.6 mmols) of D-α-amino-(2-thienyl)-acetyl chloride hydrochloride give 7β-[D-α-amino-α(2-thienyl)-acetylamino]-3-methoxy-3-cephem-4-carboxylic acid in the form of the inner salt, melting point 140° C. (with decomposition); thin layer chromatogram (silica gel; identification with iodine): Rf~0.22 (system: n-butanol/acetic acid;water, 67:10:23) and Rf~0.53 (system: isopropanol/formic acid/water, 77:4:19); ultraviolet absorption spectrum: $\lambda_{max}=235$ mμ (ε = 11,400) and $\lambda_{shoulder}=272$ mμ (ε=6,100) in 0.1 N hydrochloric acid, and $\mu_{max}=238$ mμ (ε=11,800) and $\mu_{shoulder}=267$ mμ (ε=6,500) in 0.1 N aqueous sodium bicarbonate solution.

If stage (a) is replaced by reaction with (b) 940 mg (4.5 mmols) of D-α-amino-(1,4-cyclohexadienyl)acetyl chloride hydrochloride, 7β-[D-α-amino-α-(1,4-cyclohexadienyl)-acetylamino]-3-methoxy-3-cephem-4-carboxylic acid is obtained in the form of the inner salt, melting point 170° C. (with decomposition); thin layer chromatogram (silica gel; identification with iodine): Rf~0.19 (system: n-butanol/acetic acid/water, 67:10:23) and Rf~0.58 (system: isopropanol/formic acid/water, 77:4:19); ultraviolet absorption spectrum: $\mu_{max}=267$ mμ (ε=6,300) in 0.1 N hydrochloric acid, and 82 $_{max}=268$ mμ (ε=6,600) in 0.1 N aqueous sodium bicarbonate solution, $[\alpha]_D^{20}=+88°\pm1°$ (c=1.06; 0.1 N hydrochloric acid).

If stage (a) is replaced by reaction with (c) 800 mg (3.6 mmols) of D-α-amino-4-hydroxyphenylacetyl chloride hydrochloride, 7β-[D-α-amino-α-(4-hydroxyphenyl)-acetylamino]-3-methoxy-3-cephem-4-carboxylic acid is obtained in the form of the inner salt, melting point =243°-244.5° C. (with sintering starting from 231° C. onwards) (with decomposition); thin layer chromatogram (silica gel; identification with iodine): Rf~0.24 (system: n-butanol/acetic acid/water, 67:10:23) and Rf~0.57 system: isopropanol/formic acid/water, 77:4:19); ultraviolet absorption spectrum: $\mu_{max}=228$ mμ (ε=12,000) and 271 mμ (ε=6,900) in 0.1 N hydrochloric acid, and $\mu_{max}$ 227 mμ (ε=10,500) and $\lambda_{shoulder}=262$ mμ (ε=8,000) in 0.1 N aqueous sodium bicarbonate solution, $[\alpha]_D^{20}=+165°\pm1°$ (c=1.3; 0.1 N hydrochloric acid).

EXAMPLE 25

The following compounds can be prepared analogously from suitable intermediate products obtainable in accordance with the invention: 7β-amino-3-methoxy-3-cephem-4-carboxylic acid diphenylmethyl ester or salts thereof, 3-n-butoxy-7β-phenylacetylamino-3-cephem-4-carboxylic acid diphenylmethyl ester, 3-n-butoxy-7β-(D-α-tert.-butoxycarbonylamino-α-phenylacetylamino)-3-cephem-4-carboxylic acid diphenylmethyl ester, 3-n-butoxy-7β-(D-α-phenylglycylamino)-3-cephem-4-carboxylic acid or salts thereof, 3-methoxy-7β-phenylacetylamino-3-cephem-4-carboxylic acid methyl ester, 3-ethoxy-7β-(D-α-tert.-butoxycarboxylamino-α-phenylacetylamino)-3-cephem-4-carboxylic acid diphenylmethyl ester, 3-ethoxy-7β-(D-α-phenylglycylamino)-3-cephem-4-carboxylic acid or salts thereof, 3-benzoxy-7β-(D-α-tert.-butoxycarbonylamino-α-phenylacetylamino)-3-cephem-4-carboxylic acid diphenylmethyl ester, 3-benzoxy-7β-(D-α-phenylglycylamino)-3-cephem-4-carboxylic acid or salts thereof, 7β-(5-benzoylamino-5-diphenylmethoxycarbonylvalerylamino)-3-methoxy-3-cephem-4-carboxylic acid diphenylmethyl ester, 7β-(D-α-tert.-butoxycarbonylamino-α-phenylacetylamino)-3-methoxy-3-cephem-4-carboxylic acid or salts thereof, 7β-[D-α-tert.-butoxycarbonylamino-α-(2-thienyl)-acetylamino]-3-methoxy-3-cephem-4-carboxylic acid diphenylmethyl ester, 7β-[D-α-tert.-butoxycarbonylamino-α-1,4-cyclohexadienyl)-acetylamino]-3-methoxy-3-cephem-4-carboxylic acid diphenylmethyl ester, 7β-[D-α-amino-α-(1-cyclohexen-1-yl)-acetylamino]-3-methoxy-3-cephem-4-carboxylic acid or salts thereof, 7β-[D-α-tert.-butoxycarbonylamino-α-(4-hydroxyphenyl)-acetylamino]-3-methoxy-3-cephem-4-carboxylic acid diphenylmethyl ester, 7β-[D-α-tert.-butoxycarbonylamino-α-(4-isothiazolyl)-acetylamino]-3-methoxy-3-cephem-4carboxylic acid diphenylmethyl ester, 7β-(D-α-tert.-butoxycarbonylamino-α- phenylacetylamino)-3-methoxycarbonyloxy-3-cephem-4-carboxylic acid diphenylmethyl ester, as well as the corresponding ceph-2-em compounds and the isomer mixtures consisting of the ceph-3-em compounds and the ceph-2-em compounds, and also the 1-oxides of the corresponding ceph-3-em compounds

What we claim is:

1. Process for the manufacture of a 7$\beta$-amino-3-cephem-3-ol-4-carboxylic acid compound of the formula

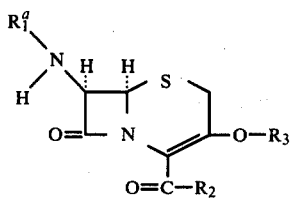

wherein $R_1{}^a$ represents an acyl group of the formula

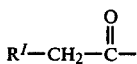

wherein $R^1$ represents lower alkyl, halogeno-lower alkyl, phenyloxy-lower alkyl, hydroxyphenyloxy-lower alkyl, protected hydroxyphenyloxy-lower alkyl, halogeno-phenyloxy-lower alkyl, or lower alkyl substituted by amino and carboxyl, wherein amino is free or protected and carboxyl is free or protected, or $R^I$ represents lower alkenyl, phenyl, hydroxyphenyl, protected hydroxyphenyl, halogenophenyl, hydroxy-halogenophenyl, protected hydroxy-halogeno-phenyl, amino-lower alkyl-phenyl, protected amino-lower alkyl-phenyl, phenyloxyphenyl, or $R^I$ represents pyridyl, thienyl, furyl, imidazolyl or tetrazolyl, or these heterocyclic groups substituted by lower alkyl, amino, protected amino, aminomethyl or protected aminomethyl, or $R^I$ represents lower alkoxy, phenyloxy, hydroxyphenyloxy, lower alkylthio, lower alkenylthio, phenylthio, pyridylthio, 2-imidazolylthio, 1,2,4-triazol-3-ylthio, 1,3,4-triazol-2-ylthio, 1,2,4-thiadiazol-3-ylthio, 1,3,4-thiadiazol-2-ylthio, or 5-tetrazolylthio, and these heterocyclylthio groups, substituted by lower alkyl, or $R^I$ represents halogeno, lower alkoxycarbonyl, cyano, carbamoyl, N-lower alkyl-carbamoyl, N-phenylcarbamoyl, lower alkanoyl, benzoyl, or azido, or $R_1{}^a$ represents an acyl group of the formula

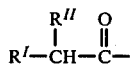

wherein $R^I$ represents lower alkyl, phenyl, hydroxyphenyl, protected hydroxyphenyl, halogenophenyl, hydroxy-halogenophenyl, protected hydroxyhalogeno-phenyl, furyl, thienyl, or isothiazolyl, or 1,4-cyclohexadienyl, and $R^{II}$ represents amino, protected amino, azido, carboxyl, protected carboxyl, cyano, sulpho, hydroxyl, protected hydroxyl, O-lower alkyl-phosphono, O,O'-di-lower alkyl-phosphono or halogeno, $R_2$ represents hydroxyl, or a group $R_2{}^A$ which is halogen or which together with the carbonyl grouping —C(=O)— forms an esterified protected carboxyl group, and $R_3$ represents hydrogen, lower alkyl, phenyl-lower alkyl, diphenyl-lower alkyl or tri-lower alkyl silyl, the corresponding 2-cephem compound of the formula

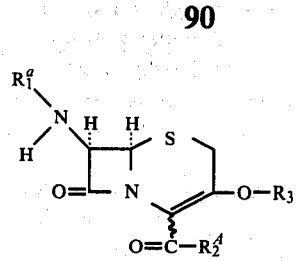

wherein $R_1{}^a$, $R_2{}^A$ and $R_3$ have the abovementioned meanings, or a mixture of a compound of the formula IA and IB, or salts of such compounds with salt-forming groups, characterised in that a compound of the formula

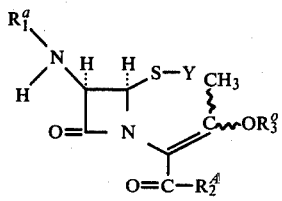

wherein $R_1{}^a$, and $R_2{}^A$ have the meanings mentioned under formula IA, $R_3°$ represents lower alkyl phenyl-lower alkyl, diphenyllower alkyl or tri-lower alkyl silyl, and Y represents a leaving group of the formula —S-$R_4$, wherein $R_4$ is 1-methyl-imidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 2-quinolyl, 1-methyl-benzimidazol-2-yl, benzthiazol-2-yl or benzoxazol-2-yl, or Y represents a leaving group of the formula —$SO_2$-$R_5$, wherein $R_5$ represents phenyl, or phenyl substituted by lower alkyl, lower alkoxy, halogen, phenyl, phenyloxy, or nitro, is treated in an inert solvent at temperatures of between room temperature and 50° C. with a diazabicycloalkene, a tetra-lower alkylguanidine or a trilower alkylamine.

2. Process according to claim 1, characterised in that $R_1{}^a$ represents phenylacetyl, phenyloxyacetyl or D-$\alpha$-tert.-butyloxycarbonylamino-$\alpha$-phenylacetyl.

3. Process according to claim 1, characterised in that $R_2{}^A$ represents benzyloxy, p-nitrobenzyloxy, diphenylmethoxy, lower alkoxy, 2-halogeno-lower alkoxy, or halogen.

4. Process according to claim 1, characterised in that $R_3$ denotes lower alkyl, benzyl, diphenylmethyl or trimethylsilyl.

5. Process according to claim 1, characterised in that $R_4$ is benzthiazol-2-yl.

6. Process according to claim 1, characterised in that $R_4$ is benzoxazol-2-yl.

7. Process according to claim 1, characterised in that Y denotes a —$SO_2$-$R_5$ group, wherein $R_5$ is phenyl, p-tolyl, o- or p-methoxyphenyl or p-nitrophenyl.

8. Process according to claim 1, characterised in that 1,5-diazabicyclo[4.3.0]non-5-ene or 1,5-diazabicyclo[5.4.0]undec-5-ene, is used as the base.

9. Process according to claim 1, characterised in that tetramethylguanidine or tri-ethylamine is used as the base.

10. Process according to claim 1, characterised in that 7$\beta$-phenoxyacetamido-3-methoxy-3-cephem-4-carboxylic acid p-nitrobenzyl ester, 7$\beta$-phenoxyacetamido-3-methoxy-2-cephem-4-carboxylic acid p-nitrobenzyl ester, or a mixture thereof is manufactured.

11. Process according to claim 1, characterised in that 7β-phenoxyacetamido-3-methoxy-3-cephem-4-carboxylic acid diphenylmethyl ester, 7β-phenoxyacetamido-3-methoxy-2-cephem-4-carboxylic acid diphenylmethyl ester or a mixture thereof, is manufactured.

12. Process according to claim 1, characterised in that 7β-phenoxyacetamido-3-methoxy-3-cephem-4-carboxylic acid 2,2,2-trichloroethyl ester, 7β-phenoxyacetamido-3-methoxy-2-cephem-4-carboxylic acid 2,2,2-trichloroethyl ester, or a mixture thereof is manufactured.

13. Process according to claim 1, characterised in that 3-methoxy-7β-phenylacetylamino-3-cephem-4-carboxylic acid diphenylmethyl ester, 3-methoxy-7β-phenylacetylamino-2-cephem-4-carboxylic acid diphenylmethyl ester or a mixture thereof is manufactured.

14. Process according to claim 1, characterised in that 3-methoxy-7β-(D-α-tert.-butoxycarbonylamino-α-phenylacetylamino)-3-cephem-4-carboxylic acid diphenylmethyl ester, 3-methoxy-7β-(D-α-tert.-butoxycarbonylamino-α-phenylacetyl)-2-cephem-4-carboxylic acid diphenylmethylester or a mixture thereof is manufactured.

15. Process according to claim 1, characterised in that 7α-phenoxyacetamido-3-benzyloxy-3-cephem-4-carboxylic acid p-nitrobenzyl ester, 7β-phenoxyacetamido-3-benzyloxy-2-cephem-4-carboxylic acid p-nitrobenzyl ester, or a mixture thereof is manufactured.

16. Process according to claim 1 characterised in that 7β-phenoxyacetamido-3-diphenylmethoxy-3-cephem-4-carboxylic acid p-nitrobenzyl ester, 7β-phenoxyacetamido-3-diphenylmethoxy-2-cephem-4-carboxylic acid p-nitrobenzylester, or a mixture thereof is manufactured.

* * * * *